United States Patent
Jones et al.

(10) Patent No.: US 8,607,787 B2
(45) Date of Patent: *Dec. 17, 2013

(54) DOSE DELIVERY DEVICE FOR INHALATION

(71) Applicants: Andrew Jones, Rosindale, MA (US); Richard L. Miller, Needham, MA (US)

(72) Inventors: Andrew Jones, Rosindale, MA (US); Richard L. Miller, Needham, MA (US)

(73) Assignee: Manta Devices, LLC, Roslindale, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/647,881

(22) Filed: Oct. 9, 2012

(65) Prior Publication Data

US 2013/0032144 A1    Feb. 7, 2013

Related U.S. Application Data

(63) Continuation of application No. 12/168,445, filed on Jul. 7, 2008, now Pat. No. 8,291,901.

(60) Provisional application No. 60/948,331, filed on Jul. 6, 2007, provisional application No. 60/971,812, filed on Sep. 12, 2007.

(51) Int. Cl.
*A61M 15/00* (2006.01)
*B65D 83/06* (2006.01)

(52) U.S. Cl.
USPC .............. 128/203.15; 128/200.14; 128/203.21

(58) Field of Classification Search
USPC ............. 128/200.14, 200.17, 200.21, 200.22, 128/203.12, 203.15, 203.19, 203.21
See application file for complete search history.

(56) References Cited

U.S. PATENT DOCUMENTS

| | | | |
|---|---|---|---|
| 2,307,986 A | 1/1943 | Bolte et al. | |
| 2,860,638 A | 11/1958 | Bartolomeo | |

(Continued)

FOREIGN PATENT DOCUMENTS

| | | |
|---|---|---|
| DE | 4400083 A1 | 7/1995 |
| EP | 0407276 | 1/1991 |

(Continued)

OTHER PUBLICATIONS

Partial International Search Report from related International Application No. PCT/US2008/008303 dated Dec. 4, 2008.

(Continued)

*Primary Examiner* — Jackie Ho
*Assistant Examiner* — Kathryn E Ditmer
(74) *Attorney, Agent, or Firm* — Wolf, Greenfield & Sacks, P.C.

(57) ABSTRACT

Methods and devices for delivering a dose, such as a medicament, for inhalation. A dose may be stored by a delivery device and dispersed and delivered in a metered fashion to a subject, such as by the subject inhaling via a mouthpiece of the delivery device. One or more chambers of the device may have a toroidal shape and may be arranged to be selectively opened for fluid communication with a flow path of the delivery device, such as by sliding the chamber relative to a portion of the flow path. The flow path may include a restriction that permits air to bypass the chamber, and/or the chamber may be arranged so that fluid entering the chamber interacts with fluid exiting the chamber so as to enhance dispersion of the dose.

34 Claims, 43 Drawing Sheets

(56) References Cited

U.S. PATENT DOCUMENTS

| | | | |
|---|---|---|---|
| 2,974,787 A | 3/1961 | Cooper | |
| 3,888,253 A | 6/1975 | Watt et al. | |
| 2,893,392 A | 6/1976 | Gerstel et al. | |
| 4,249,526 A | 2/1981 | Dean et al. | |
| 4,338,931 A | 7/1982 | Cavazza | |
| 4,601,896 A | 7/1986 | Nugent | |
| 4,841,964 A * | 6/1989 | Hurka et al. | 128/203.15 |
| 5,035,237 A | 7/1991 | Newell et al. | |
| 5,167,242 A | 12/1992 | Turner et al. | |
| 5,239,993 A | 8/1993 | Evans | |
| 5,320,714 A | 6/1994 | Brendel | |
| 5,388,572 A | 2/1995 | Mulhauser et al. | |
| 5,400,808 A | 3/1995 | Turner et al. | |
| 5,476,093 A | 12/1995 | Lankinen | |
| 5,501,236 A | 3/1996 | Hill et al. | |
| 5,562,918 A | 10/1996 | Stimpson | |
| 5,596,982 A | 1/1997 | Blaha-Schnabel | |
| 5,622,166 A | 4/1997 | Eisele et al. | |
| 5,647,349 A | 7/1997 | Ohki et al. | |
| 5,669,378 A | 9/1997 | Pera et al. | |
| 5,673,793 A | 10/1997 | Seidler | |
| 5,687,710 A * | 11/1997 | Ambrosio et al. | 128/203.15 |
| 5,775,320 A | 7/1998 | Patton et al. | |
| 5,893,452 A | 4/1999 | De Nervo | |
| 5,921,237 A | 7/1999 | Eisele et al. | |
| 5,947,117 A | 9/1999 | Herold et al. | |
| 5,954,204 A | 9/1999 | Grabowski | |
| 6,029,663 A | 2/2000 | Eisele et al. | |
| 6,089,228 A | 7/2000 | Smith et al. | |
| 6,209,538 B1 | 4/2001 | Casper et al. | |
| 6,230,707 B1 | 5/2001 | Horlin | |
| 6,234,169 B1 | 5/2001 | Bulbrook et al. | |
| 6,328,034 B1 | 12/2001 | Eisele et al. | |
| 6,347,629 B1 | 2/2002 | Braithwaite | |
| 6,401,712 B1 | 6/2002 | Von Schuckmann | |
| 6,427,688 B1 | 8/2002 | Ligotke et al. | |
| 6,443,152 B1 | 9/2002 | Lockhart et al. | |
| 6,443,307 B1 | 9/2002 | Burridge | |
| 6,550,477 B1 | 4/2003 | Casper et al. | |
| 6,595,203 B1 | 7/2003 | Bird | |
| 6,595,210 B2 | 7/2003 | Ohki et al. | |
| 6,655,381 B2 | 12/2003 | Keane et al. | |
| 6,681,768 B2 | 1/2004 | Haaije de Boer et al. | |
| 6,748,947 B2 | 6/2004 | Keane et al. | |
| 6,810,872 B1 | 11/2004 | Ohki et al. | |
| 6,871,646 B2 | 3/2005 | Keane et al. | |
| 6,932,082 B2 | 8/2005 | Stein | |
| 6,941,947 B2 | 9/2005 | Young et al. | |
| 6,971,384 B2 * | 12/2005 | Gieschen et al. | 128/203.15 |
| 7,025,056 B2 | 4/2006 | Eason et al. | |
| 7,025,057 B2 | 4/2006 | Chawla | |
| 7,143,765 B2 | 12/2006 | Asking et al. | |
| 7,401,713 B2 | 7/2008 | Ede et al. | |
| 7,617,822 B2 | 11/2009 | De Boer et al. | |
| 8,109,267 B2 | 2/2012 | Villax et al. | |
| 2001/0020472 A1 * | 9/2001 | Horlin | 128/203.15 |
| 2001/0027790 A1 | 10/2001 | Gieschen et al. | |
| 2001/0029948 A1 | 10/2001 | Ingle et al. | |
| 2002/0006316 A1 | 1/2002 | Schuler et al. | |
| 2002/0020408 A1 | 2/2002 | Knauer | |
| 2002/0092523 A1 | 7/2002 | Connelly et al. | |
| 2002/0170560 A1 | 11/2002 | Young et al. | |
| 2003/0034271 A1 | 2/2003 | Burridge | |
| 2003/0192532 A1 * | 10/2003 | Hopkins | 128/200.14 |
| 2004/0107963 A1 | 6/2004 | Finlay et al. | |
| 2004/0118399 A1 * | 6/2004 | Young et al. | 128/203.15 |
| 2004/0182387 A1 * | 9/2004 | Steiner et al. | 128/203.15 |
| 2004/0206350 A1 | 10/2004 | Alston et al. | |
| 2004/0211419 A1 | 10/2004 | Eason et al. | |
| 2004/0236282 A1 | 11/2004 | Braithwaite | |
| 2005/0022813 A1 | 2/2005 | Alston | |
| 2005/0188988 A1 * | 9/2005 | Poole et al. | 128/203.15 |
| 2006/0005833 A1 | 1/2006 | Gieschen et al. | |
| 2006/0108877 A1 | 5/2006 | Tegel | |
| 2006/0169278 A1 | 8/2006 | Djupesland et al. | |
| 2007/0023381 A1 | 2/2007 | Cerveny | |
| 2007/0074721 A1 | 4/2007 | Harmer et al. | |
| 2007/0151562 A1 | 7/2007 | Jones et al. | |
| 2008/0251072 A1 | 10/2008 | Lulla et al. | |
| 2008/0314384 A1 | 12/2008 | Harris et al. | |
| 2009/0250057 A1 | 10/2009 | Wachtel | |
| 2009/0308392 A1 | 12/2009 | Smutney et al. | |
| 2009/0321295 A1 | 12/2009 | Ede et al. | |

FOREIGN PATENT DOCUMENTS

| | | |
|---|---|---|
| EP | 1844809 A1 | 10/2007 |
| GB | 1211168 A | 11/1967 |
| GB | 2179260 A | 3/1987 |
| GB | 2375310 A | 11/2002 |
| GB | 2405798 A | 3/2005 |
| GB | 2420982 A | 6/2006 |
| JP | 08-103499 A | 4/1996 |
| WO | WO 90/07351 A1 | 7/1990 |
| WO | WO 9204928 A2 * | 4/1992 |
| WO | WO 96/09085 | 3/1996 |
| WO | WO 99/06092 A1 | 2/1999 |
| WO | WO 01/05675 A1 | 1/2001 |
| WO | WO 01/26720 A1 | 4/2001 |
| WO | WO 01/56640 A1 | 9/2001 |
| WO | WO 01/85097 | 11/2001 |
| WO | WO 02/098495 A1 | 12/2002 |
| WO | WO 03/000326 A1 | 1/2003 |
| WO | WO 03/015857 A1 | 2/2003 |
| WO | WO 2004/103446 A1 | 12/2004 |
| WO | WO 2005/002654 A3 | 1/2005 |
| WO | WO 2005/025656 A1 | 3/2005 |
| WO | WO 2005/030305 A1 | 4/2005 |
| WO | WO 2006/066910 A1 | 6/2006 |
| WO | WO 2007/007110 A1 | 1/2007 |
| WO | WO 2009/092650 | 7/2009 |

OTHER PUBLICATIONS

International Preliminary Report on Patentability from related International Application No. PCT/US2010/000090 dated Jul. 19, 2011.

* cited by examiner

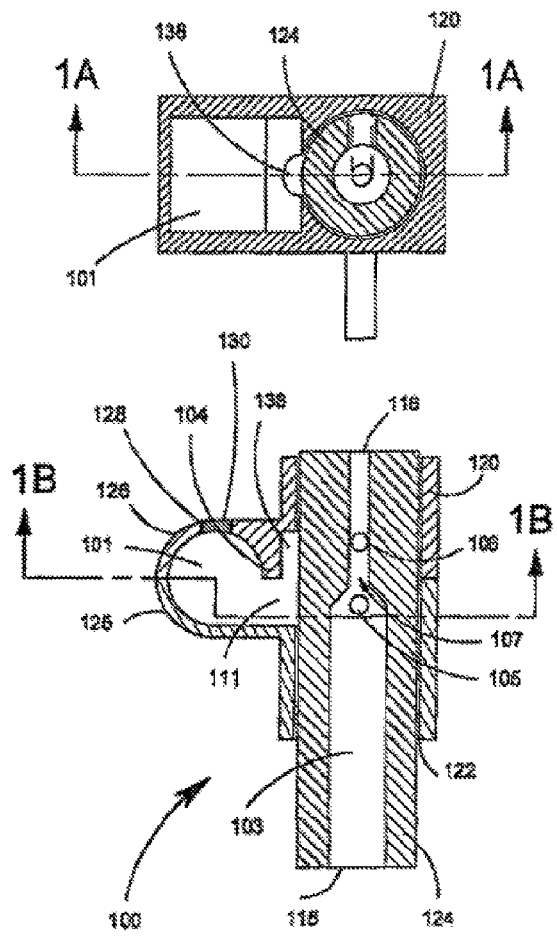
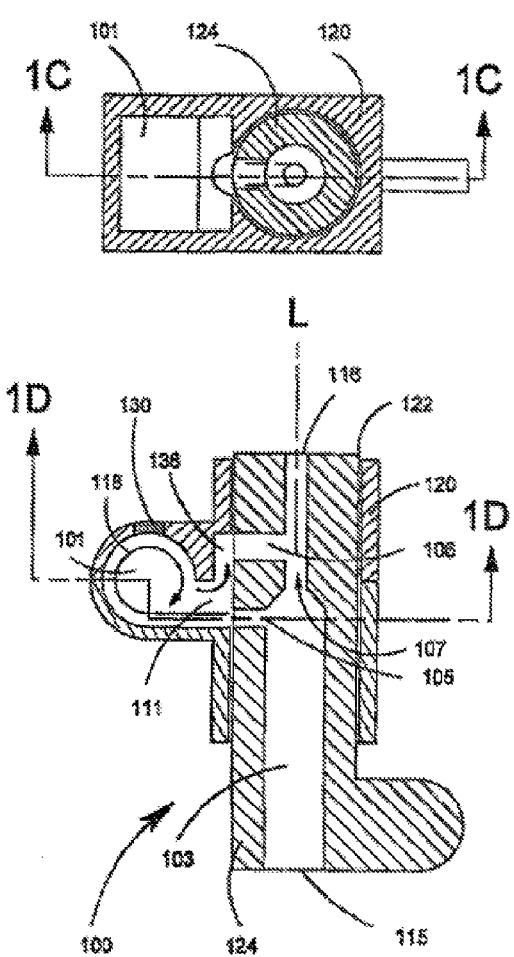
Figure 1A
Figure 1C

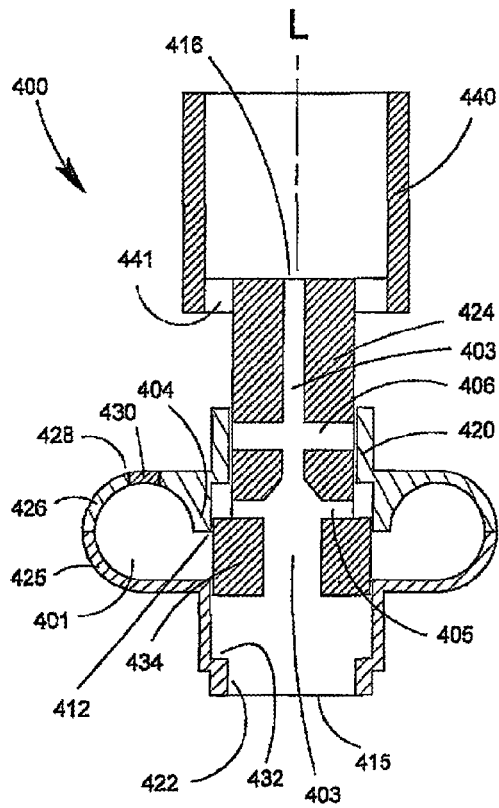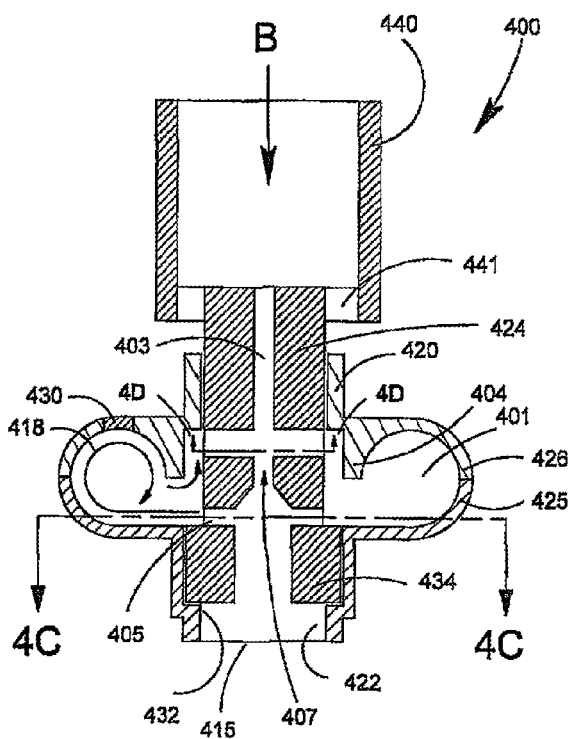
Figure 4A
Figure 4B
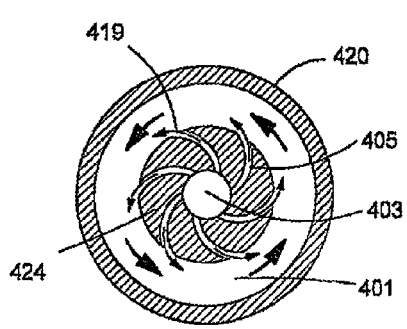
Figure 4C
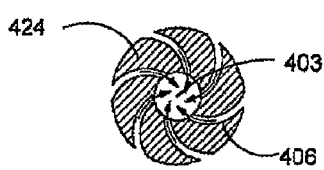
Figure 4D
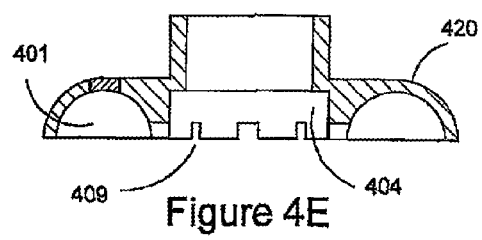
Figure 4E

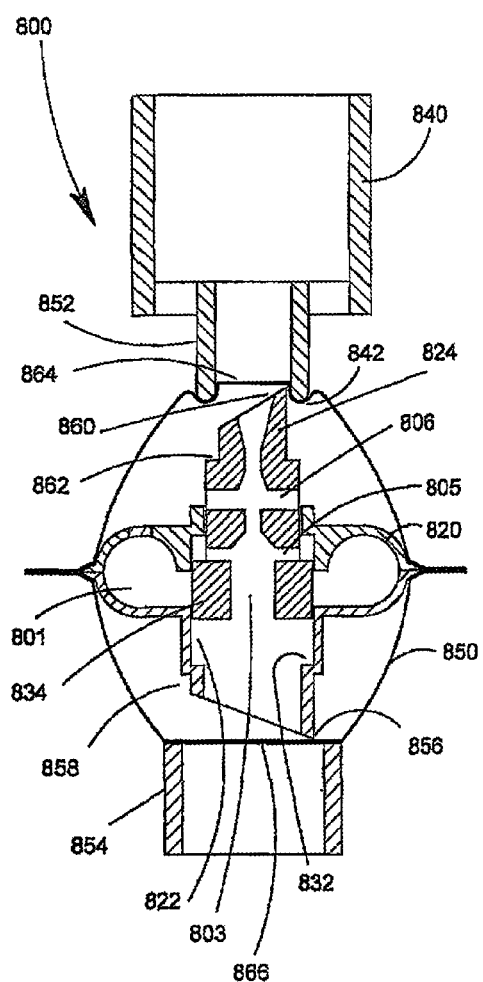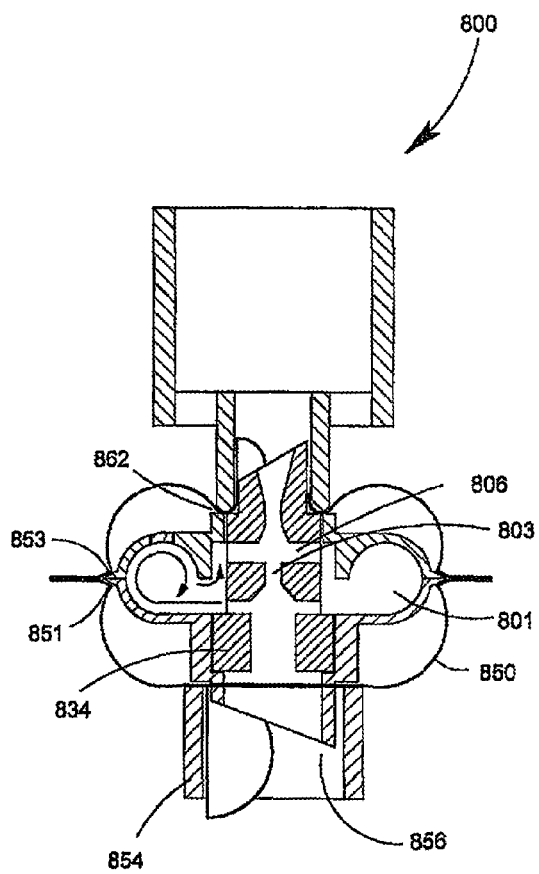
Figure 8A
Figure 8B

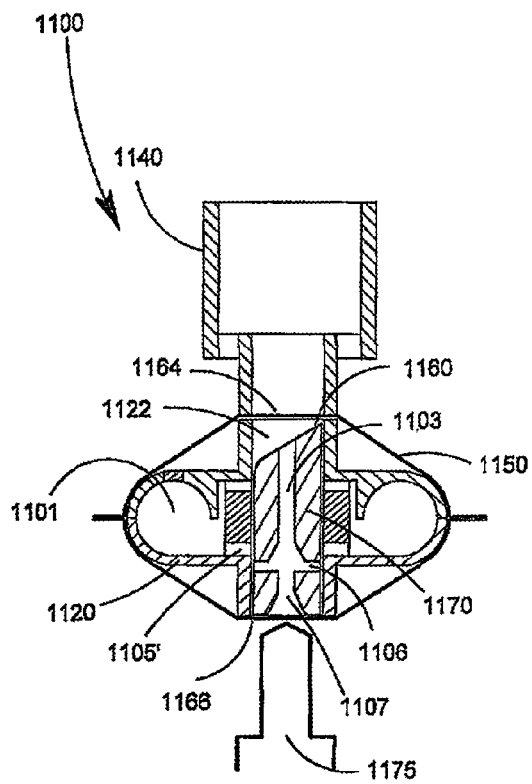
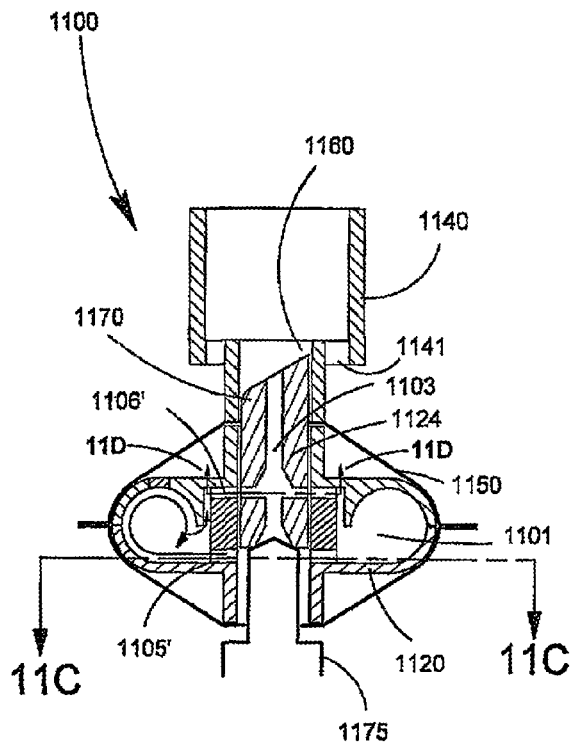
Figure 11A
Figure 11B
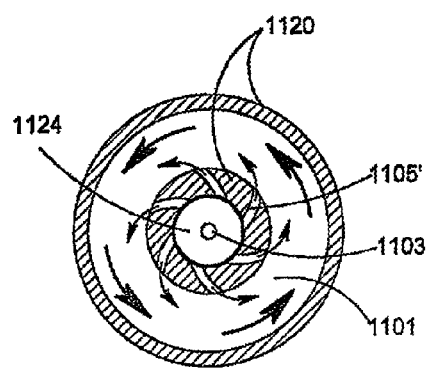
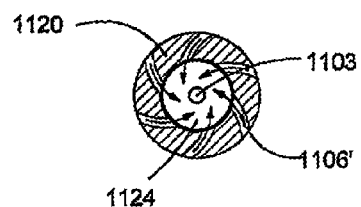
Figure 11C
Figure 11D

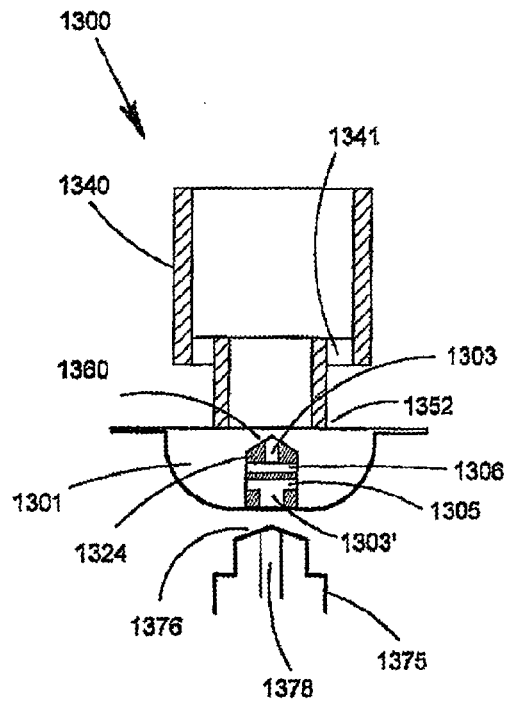
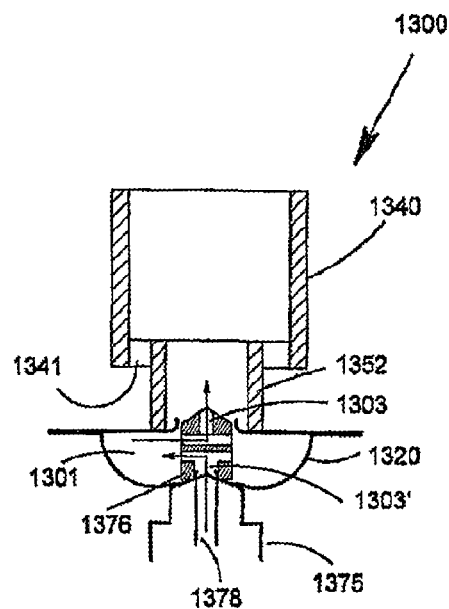
Figure 13A          Figure 13B
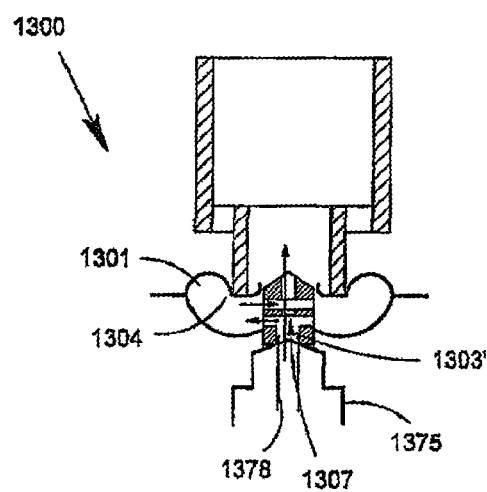
Figure 13C

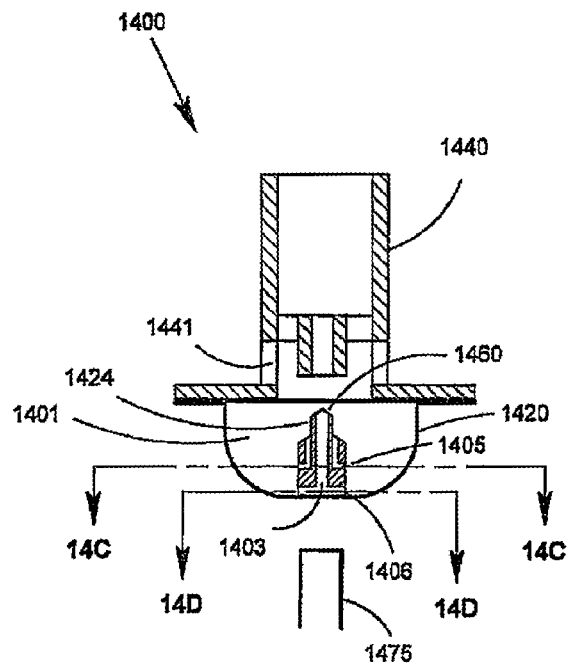
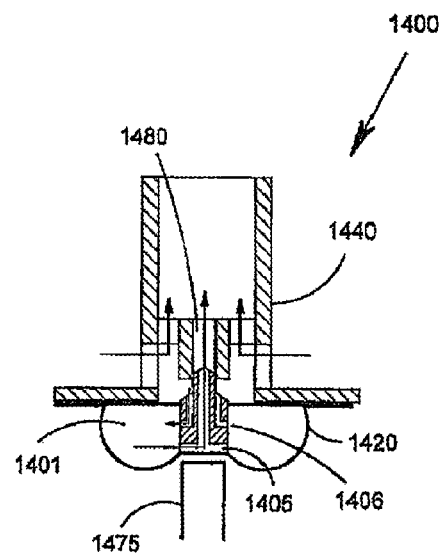
Figure 14A     Figure 14B
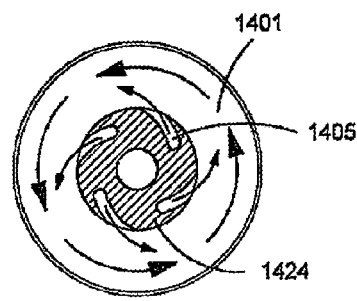
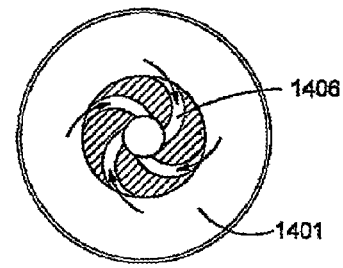
Figure 14C     Figure 14D

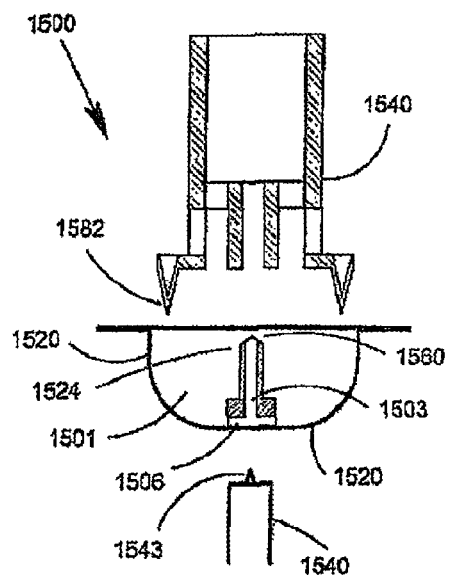
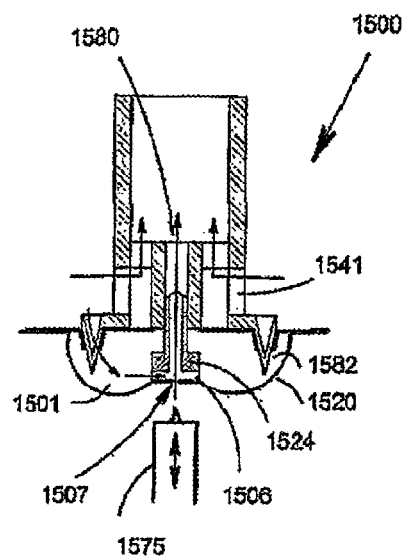
Figure 15A    Figure 15B
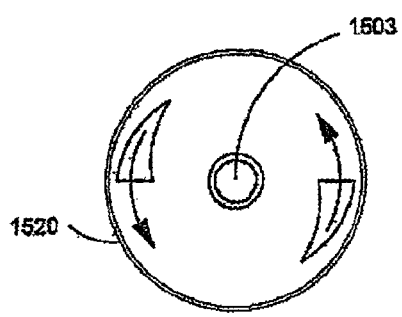
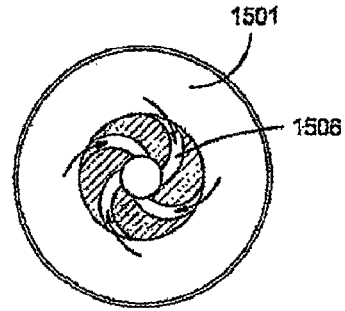
Figure 15C    Figure 15D
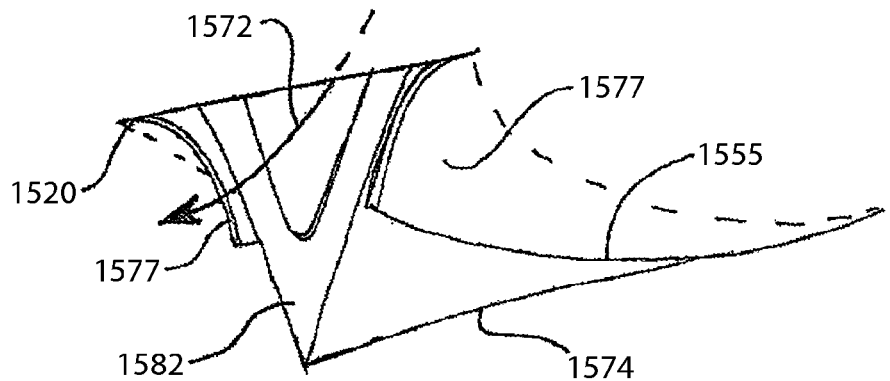
Figure 15E

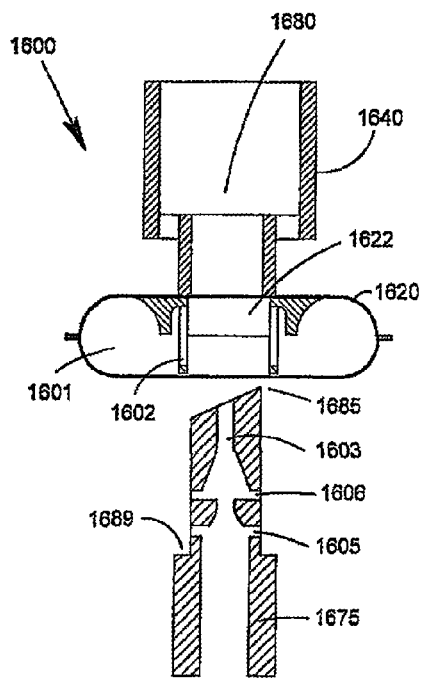
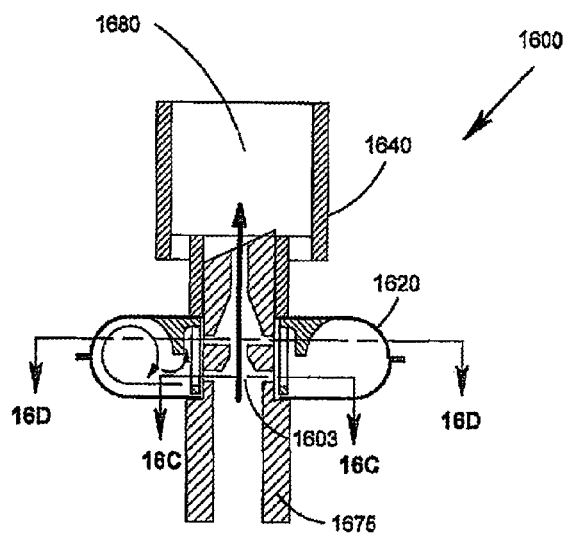
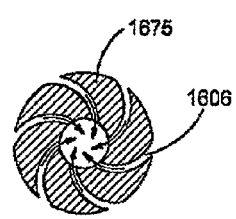
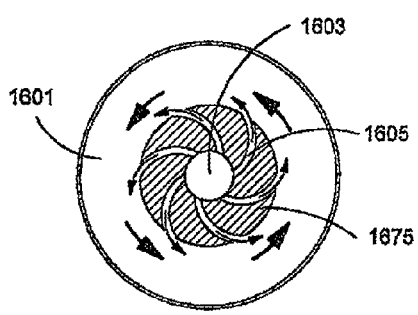
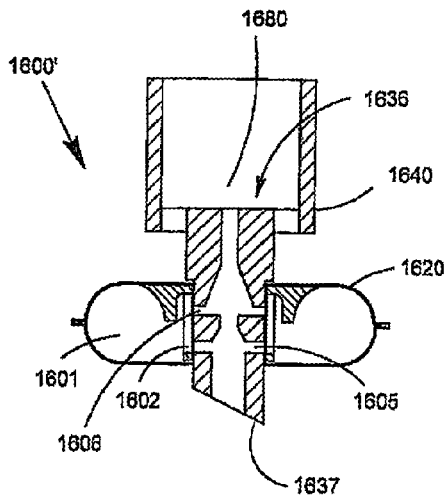
Figure 16A
Figure 16B
Figure 16D
Figure 16C
Figure 16E

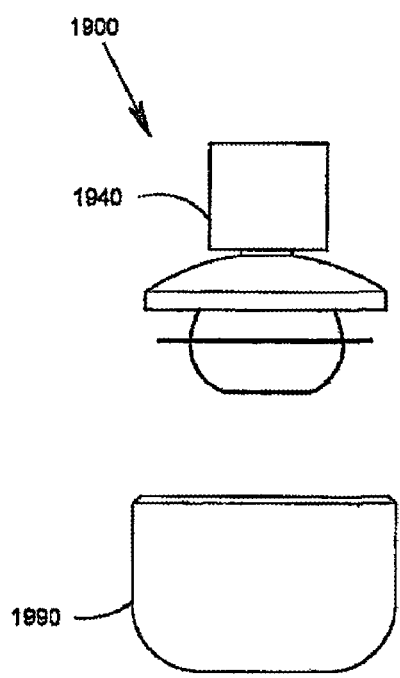
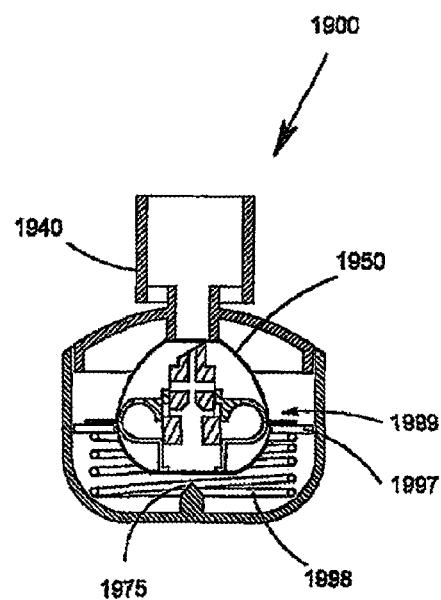
Figure 19A
Figure 19B (2X scale)

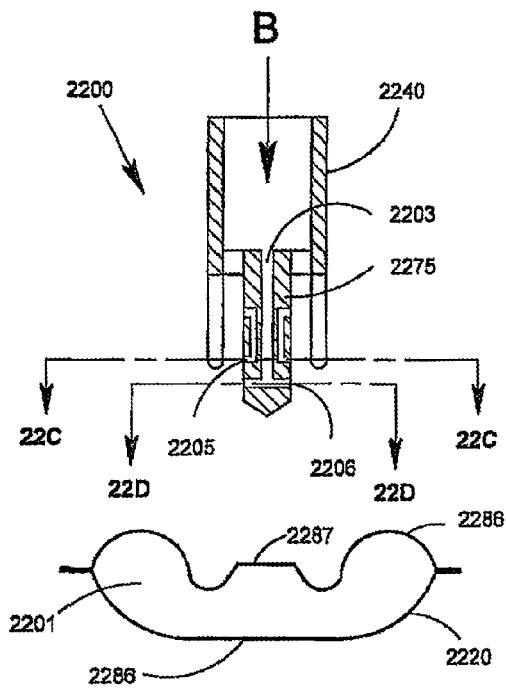
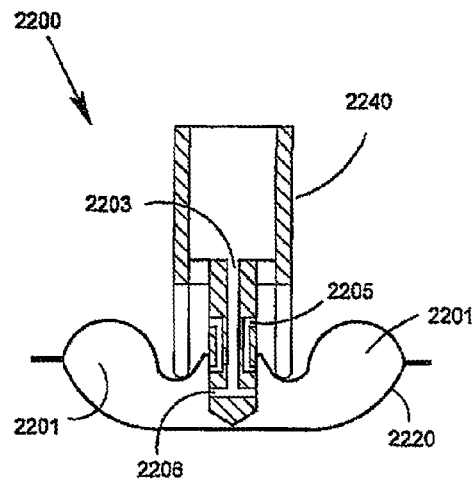
Figure 22B
Figure 22A
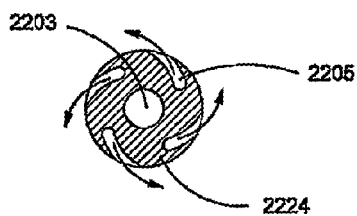
Figure 22C
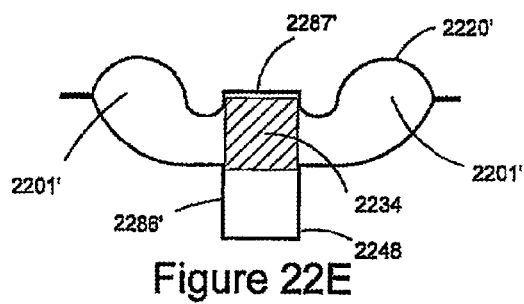
Figure 22E
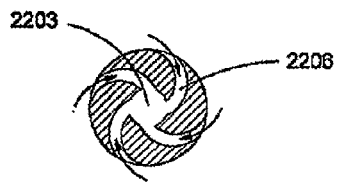
Figure 22D
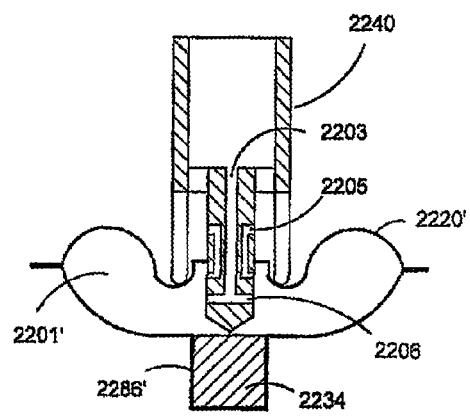
Figure 22F

DOSE DELIVERY DEVICE FOR INHALATION

This application is a continuation of U.S. patent application Ser. No. 12/168,445, filed Jul. 7, 2008 which claims the benefit of U.S. Provisional Application No. 60/948,331, filed Jul. 6, 2007 and U.S. Provisional Application No. 60/971,812, filed Sep. 12, 2007, each of which is hereby incorporated by reference in its entirety.

RELATED ART

Medicament in the form of dry powder may be delivered directly into the lungs, such as by inhalation. Administering medicament in this manner may prove less invasive than other drug delivery techniques, such as hypodermic injections. Direct inhalation of medicament may also allow smaller doses of medicament to be used to achieve the similar results as the same drug taken orally. Inhalation may also help avoid undesirable side effects associated with administering drugs orally or by injection.

SUMMARY

Aspects of the invention relate to devices, systems, and methods that are used to deliver a drug/medicament (such as a liquid and/or a powder). The devices, systems and methods may include features that allow the drug to be protected (e.g., from contamination and/or degradation) prior to use, and to be delivered in a precise and accurate manner. For example, in some embodiments, the drug is isolated to a selected volume/dose chamber and prevented from moving out of the selected volume prior to use. As a result, the initial location of the drug dose is known, and the dose may be delivered predictably from the same starting point.

In certain aspects of the invention, the drug may be dispersed, fluidized, and/or metered from its initial location. The drug may be delivered as fine particles, mitigating, for example, the occurrence of large clump(s), which may reduce therapeutic effectiveness of the drug. A satisfactory combination of dispersion, fluidization and metering may also enhance drug delivery, for example, by allowing substantially all of the drug dose to be delivered, which may increase safety and lower cost and waste.

Aspects of the invention relate to a device that may be configured to store and deliver one or more doses of an inhalable powder, typically including a medicament. The device may include one or more dispersion engines that each has a dose chamber in which the medicament may be stored, and a passageway, through which the medicament may be delivered. To administer medication in this aspect of the device, fluid communication is opened between the dose chamber and the passageway. Air is drawn through the passageway and the dose chamber, passively, actively, or via a combination of passive and active air flow. Air that passes through the dose chamber entrains the powder and is combined with air that passes through the passageway to provide metered delivery of the powder to the subject.

Aspects of the invention relate to a device for storing and delivering medicament. The device comprises an air path and a chamber configured for storing and delivering a medicament. The chamber may have a substantially curved interior surface and an opening that provides fluid communication with the air path. The at least one opening may include an inlet admitting air from the air path and an outlet for medicament entrained air to exit into the air path. A section of the curved interior surface may be configured to redirect at least a portion of the inlet flow toward the inlet flow of air. So configured, some of the redirected flow of air may exit the chamber through the outlet and into the air path while other portions of the redirected flow of air recirculates about the chamber.

Other aspects of the invention relate to a device for storing and delivering medicament. The device comprises a chamber configured for storing and delivering medicament that has an air inlet and an air outlet and an interior surface that includes a curved section, an inlet section, and an outlet section. The inlet section is configured to lie parallel to air that is received in the air inlet and to provide the air to the curved section for circulation about the chamber and deliver from the chamber along the outlet section. The device also comprises an air pathway in fluid communication with the chamber through the air inlet and the air outlet. Fluid communication is selectively openable and closable between the air pathway and the air inlet and the air outlet. A restriction is positioned in the air pathway between the air inlet and the air outlet.

Another aspect of the invention relates to a device for storing and delivering medicament that comprises an air path and a substantially torus-shaped chamber configured for storing and delivering medicament. An air inlet and an air outlet are positioned along a central portion of the torus-shaped chamber and provide fluid communication with the air path. The torus-shaped chamber includes a curved interior surface that receives air from the air inlet substantially along a tangent of the curved surface and that delivers air to the air outlet along a tangent of the curved surface.

Yet another aspect of the invention relates to a device for storing and delivering medicament. The device comprises an air path and a substantially torus-shaped chamber configured for storing and delivering a medicament. The chamber has a substantially curved interior surface and an opening that provides fluid communication with the air path. A first section of the curved interior surface is configured to receive air to the chamber from an inlet flow of air. A second section of the curved interior surface is configured to receive the inlet flow of air and to redirect at least a portion of the inlet flow toward the first section of the curved interior surface and through the inlet flow of air. A first portion of the redirected flow of air exits the chamber to the air path and a second portion of the redirected flow of air reenters the inlet flow of air.

Another aspect of the invention relates to a device for storing and delivering multiple doses of powdered medicament. The device comprises a plurality of dispersion engines that each includes a dose chamber and a passageway. Each dispersion engine has a first position where the dose chamber is in fluid communication with the passageway for delivery of a dose from the dose chamber. Each dispersion engine also has a second position where the dose chamber is out of fluid communication with the passageway for storing the dose within the chamber. The device also comprises an outlet that may be moved sequentially into registration with the passageway of each of the plurality of dispersion engines.

Another aspect of the invention relates to a device for storing and delivering multiple doses of powdered medicament. The device comprises a passageway and a plurality of dispersion engines that each includes a dose chamber that may be moved sequentially into registration with the passageway. Moving the passageway or dose chamber into registration opens fluid communication at an opening between the passageway and a dose chamber that is in registration with the passageway. The opening is configured to provide a flow pathway for air that enters and that leaves the dose chamber that is in registration. The dispersion engine that is in registration with the passageway includes an interior wall that is configured to direct air toward a flow of air that is entering the dose chamber.

In some embodiments, the devices, systems and methods may be free of secondary packaging to facilitate rapid and easy delivery of the drug when the drug needs to be delivered as fast as possible under a stressful circumstance, such as in an emergency situation.

Embodiments described herein may be configured for passive or active applications, or a combination of passive and active fluid administration. For example, each of the embodiments described herein may include use of a compressed fluid to assist in dispersing the drug.

The devices and systems described herein may be integrated into a wide variety of delivery configurations including, for example, a single-dose and multi-dose applications, in either active, passive, or active/passive applications. In addition, the devices, systems and methods may be applied to combination dose configurations and therapies.

The devices, systems and methods described herein may be used to deliver materials, other than a drug/medicament, to the body. The materials may be delivered through the mouth or nose and into the oral cavity and/or to the lungs. Materials that are intended to be delivered into the oral cavity include, for example, nutritional compositions (such as sugars, candy, food, vitamins, and quick energy supplements in liquid and/or powder (e.g., nanoparticles) form) and non-nutritional compositions (such as flavorants (e.g., esters)). Other materials that may be delivered into the oral cavity include those used for oral hygiene and dental treatment (e.g., breath fresheners, fluoride treatments, teeth whiteners, antibacterial compositions, mouthwashes). Drugs and related compositions (such as anesthetics, therapeutic markers) may also be delivered into the oral cavity. Materials that the may be inhaled into the lungs include, for example, drugs (e.g., for treating asthma, bronchitis, pneumonia) and therapeutic markers (such as dyes, scanning agents, radio labeling or tagging agents, UV labeling agents, contrasts agents in liquid and/or powder (e.g., nanoparticles) form). In this respect, it is to be appreciated that any of the above materials may be used in the devices, systems, and methods described herein in place of drug(s)/medicaments. It is also to be appreciated that the terms "drug" and "medicament" are used interchangeable herein, and include any of the foregoing compositions and any others, whether in powder, liquid or other form, that may be delivered to a human or animal for therapeutic, diagnostic, or other effect. In certain aspects, the delivery device is configured for use with other entranceways into a human or animal body, whether naturally formed or created otherwise, and with aspects of the human or animal body other than the respiratory system. Although the embodiments described incorporate air as the fluid for delivering the medicament, other fluids are contemplated as should be apparent to one of skill in the art.

The following terms are used throughout this application and have the following definitions.

The term "active" refers to the use of one or more external mechanisms and/or forces in addition to the patient's respiration.

The term "passive" refers to the use of the patient's respiration.

Other aspects, features and advantages will be apparent from the description of the following embodiments and from the claims.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 1A is a cross-sectional schematic diagram of an embodiment of a drug delivery device in a closed position; FIG. 1B is a cross-sectional diagram of the device shown in FIG. 1A, taken along line 1B-1B; FIG. 1C is a cross-sectional schematic diagram of the device shown in FIG. 1A in an opened position; FIG. 1D is a cross-sectional diagram of the device shown in FIG. 1C, taken along line 1D-1D; FIG. 1H is a cross-sectional schematic diagram of an embodiment of a drug delivery device in a closed position; FIG. 1I is a cross-sectional schematic diagram of an embodiment of a drug delivery device in an opened position.

FIG. 4A is a cross-sectional schematic diagram of an embodiment of a drug delivery device in a closed position; FIG. 4B is a cross-sectional schematic diagram of the device shown in FIG. 4A in an opened position; FIG. 4C is a cross-section of the device shown in FIG. 4B, taken along line 4C-4C; FIG. 4D is a cross-section of the device shown in FIG. 4B, taken along line 4D-4D; and FIG. 4E is a partial cross-sectional schematic diagram of an embodiment of a drug delivery device.

FIG. 8A is a cross-sectional schematic diagram of an embodiment of a drug delivery device in a closed position; and FIG. 8B is a cross-sectional schematic diagram of the device shown in FIG. 8A in an opened position.

FIG. 11A is a cross-sectional schematic diagram of an embodiment of a drug delivery device in a closed position; FIG. 11B is a cross-sectional schematic diagram of the device shown in FIG. 11A in an opened position; FIG. 11C is a cross-section of the device shown in FIG. 11B, taken along line 11C-11C; FIG. 11D is a cross-section of the device shown in FIG. 11B, taken along line 11D-11D.

FIG. 13A is a cross-sectional schematic diagram of an embodiment of a drug delivery device in a closed position; FIG. 13B is a cross-sectional schematic diagram of the device shown in FIG. 13A in an opened position; and FIG. 13C is a cross-sectional schematic diagram of an embodiment of a drug delivery device in an opened position.

FIG. 14A is a cross-sectional schematic diagram of an embodiment of a drug delivery device in a closed position; FIG. 14B is a cross-sectional schematic diagram of the device shown in FIG. 14A in an opened position; FIG. 14C is a cross-section of the device shown in FIG. 14B, taken along line 14C-14C; and FIG. 14D is a cross-section of the device shown in FIG. 14B, taken along line 14D-14D.

FIG. 15A is a cross-sectional schematic diagram of an embodiment of a drug delivery device in a closed position; FIG. 15B is a cross-sectional schematic diagram of the device shown in FIG. 15A in an opened position; FIG. 15C is a plan view of a housing shown in FIG. 15A after the housing has been punctured and puncturing elements have been removed (for clarity); FIG. 15D is a cross-section of the device shown in FIG. 15B, taken along line 15D-15D; and FIG. 15E is a perspective illustration of a puncturing element puncturing a housing.

FIG. 16A is a cross-sectional schematic diagram of an embodiment of a drug delivery device in a closed position; FIG. 16B is a cross-sectional schematic diagram of the device shown in FIG. 16A in an opened position; FIG. 16C is a cross-section of the device shown in FIG. 16B, taken along line 16C-16C; FIG. 16D is a cross-section of the device shown in FIG. 16B, taken along line 16D-16D; and FIG. 16E is a cross-sectional schematic diagram of an embodiment of a drug delivery device in an opened position.

FIG. 19A is a perspective view of two sub-assemblies of an embodiment of a drug delivery device in a closed position; FIG. 19B is a cross-sectional schematic diagram of the device shown in FIG. 19A in a closed position.

FIG. 22A is a cross-sectional schematic diagram of an embodiment of a drug delivery device in a closed position; FIG. 22B is a cross-sectional schematic diagram of the device shown in FIG. 22A in an opened position; FIG. 22C is a cross-section of the device shown in FIG. 22A, taken along line 22C-22C; FIG. 22D is a cross-section of the device shown in FIG. 22A, taken along line 22D-22D; FIG. 22E is a cross-sectional schematic diagram of an embodiment of a housing; and FIG. 22F is a cross-sectional schematic diagram of an embodiment of the drug delivery device shown in FIG. 22A used with the housing shown in FIG. 22E.

DETAILED DESCRIPTION

Figure 1E:
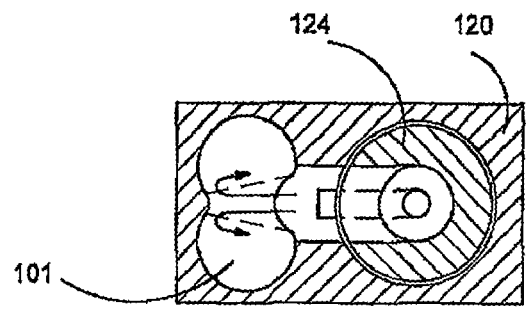
FIG. 1E is a cross-sectional diagram similar to FIG. 1D of an embodiment of a drug delivery device.
Figure 1F:
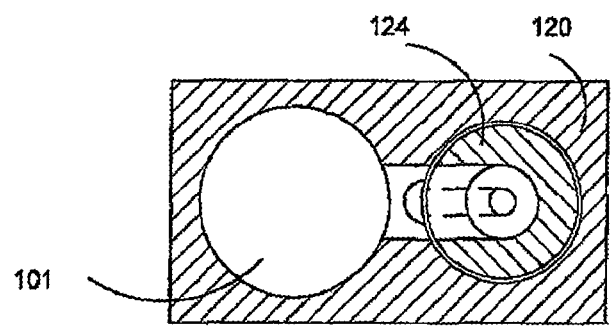
FIG. 1F is a cross-sectional diagram similar to FIG. 1D of an embodiment of a drug delivery device.
Figure 1G:
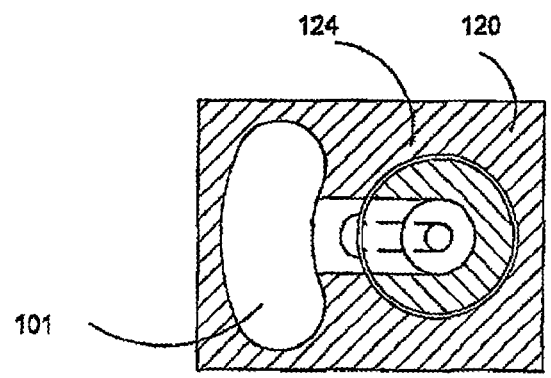
FIG. 1G is cross-sectional diagram similar to FIG. 1D of an embodiment of a drug delivery device.

The devices of the present invention include one or more chambers for storing and delivering medicament. The chamber may be placed in fluid communication with an air pathway to ready the medicament for delivery to a subject. Air is drawn or pushed through the air pathway, a portion of which enters the chamber to entrain and subsequently deliver the medicament to a subject.

According to some aspects, multiple dose chambers may be incorporated into "dispersion engines" within an inhalation device. Each dispersion engine may also include a passageway that may selectively be placed in fluid communication with the corresponding dose chamber to provide a pathway for delivery of the dose to a subject. Such devices are referred to herein as "multi-dose" devices. Alternately, multi-dose devices may include a common passageway that may be selectively placed into fluid communication with each of a plurality of dose chambers to provide a pathway for delivery of multiple doses to a subject.

According to other aspects, a dose chamber may be selectively opened and/or closed. Keeping medicament partitioned in an area of the device prior to delivery, such as in the dose chamber and passageway, in the chamber, and/or in a portion of the chamber, may provide a consistent starting place for medicament during the delivery process. Providing a consistent starting place, in turn, may lead to a more consistent metered delivery of medicament to a subject. Additionally, retaining medicament in a selectively openable/closable portion of the device may also prevent the medicament from being degraded, such as by exposure to light, moisture, contaminants, and the like.

According to other aspects, the passageway may be configured to mix air that passes through a dose chamber with air that enters the passageway from elsewhere. This may help to further disperse any medicament flowing from the chamber and/or to provide for a metered delivery of medicament to the subject. In these embodiments, a restriction may be positioned in the passageway, upstream of an outlet from the chamber to the passageway, such that flow is urged to the passageway both from the dose chamber and through the restriction.

According to other aspects, chambers may include an obstacle or other feature to direct air that has been entrained with medicament back toward air that is entering the chamber. A portion of the air and entrained particles of medicament, typically larger particles, may pass into the air that is entering the chamber and then be re-circulated through the chamber. Another portion of the air, typically including smaller particles of medicament, may exit the chamber to the passageway for delivery to the subject. Directing air back toward air that is entering the chamber, in this regard, may help meter the flow of medicament from the chamber and/or prevent larger agglomerated particles from being dispensed before being broken down into smaller particles.

According to other aspects, a dose chamber may lack an obstacle but have a curved construction that provides a natural shape for air to flow throughout the dose chamber to reduce pockets or dead spots where medicament tends to collect in dose chambers having cornered, angular or other non-curved geometry. As air flows through the dose chamber, medicament is spread across the internal surface of the chamber. As the air circulates, the medicament is entrained from the surface and delivered to the air passageway with minimal residual medicament left behind in the dose chamber after actuation of the inhaler.

FIGS. 1A, 1B, 1C and 1D show a drug delivery device 100, with FIG. 1A showing the device in a closed position and FIG. 1C showing the device in an opened position. Drug delivery device 100 includes a housing 120 having a passageway 122, and a first member 124 rotatably located within the passageway.

In addition to passageway 122, housing 100 includes a first chamber 101 that is capable of being in fluid communication with the passageway via an opening 111. First chamber 101 is used to contain one or more drugs and has a geometry configured to meter and to prevent the drug (e.g., a powder and/or a liquid) from leaving device 100 as large clump(s) and to help fluidize the drug (e.g., by re-circulating the drug in the first chamber). As shown, chamber 101 is defined in part by an obstacle 104 configured to slow the egress of the drug from first chamber 101. Fluid flow entering first chamber 101 from an inlet channel 105 of first member 124 entrains the drug, carries it along the shape of the first chamber, and causes it to re-circulate in the first chamber (path 118).

As shown FIGS. 1A and 1C, the cross-section of first chamber 101 is a curved shape that directs fluid flow along its boundary wall back to opening 111 (which is the point of entry of the fluid flow). It is believed that the at least partially curved shape (e.g., generally round, oval, racetrack or elliptical) forces the drug against the boundary wall by centrifugal force, thereby causing de-agglomeration and dispersion. In other embodiments, the longitudinal cross-sectional shape may vary including, for example, race track (FIG. 1E), circular (FIG. 1F), and elliptical, circumferential (FIG. 1F). The width of first chamber 101 may be equal to or wider than inlet channel 105.

Furthermore, the geometry of first chamber 101 creates a volume 138 that is separated from re-circulating fluid path 118 in the first chamber by obstacle 104, that is in close proximity to an outlet channel 106 of first member 124, and provides a fluid path between the first chamber and the outlet channel. During use, volume 138 works with first chamber 101 and obstacle 104 as part of a larger space (including volume 138, first chamber 101 and obstacle 104) that provides drug dispersion and metering, e.g., so that the drug is not delivered as large clump(s). However, as described below, in some embodiments (e.g., devices 200, 400, 800), the volume (e.g., volume 138, 238) is initially isolated from a first chamber so that the drug remains in the first chamber. Isolating the drug to a known location (namely, the first chamber) provides a known starting point so that all of the drug may be delivered accurately and predictably. When the first chamber is unsealed (if applicable), the first chamber works with the obstacle and the volume (if applicable) to disperse and to meter the drug. Furthermore, as described in other embodiments below, volume 138 may have different cross sectional shapes and/or vary in area to control delivery of the drug from first chamber 101 to outlet channel 106.

In other embodiments, a drug delivery device does not include volume 138. For example, the device does not include obstacle 104, and first chamber 101 fluidly communicates with outlet channel 105 via a wide opening 111.

As shown, housing 120 includes two parts 125, 126 that join to define passageway 122 and first chamber 101, and an opening 128 in fluid communication with first chamber 101.

Opening 128 may be used to load first chamber 101 with a drug and may be subsequently covered with a plug 130. Other approaches may be employed to place a medicament in the first chamber as should be apparent to one of skill in the art. Housing 100 may include (e.g., is formed of) a moisture impervious material (such as plastic) to prevent contamination and/or degradation of the drug. In other embodiments, housing 100 includes more than two parts or only one unitary part.

First member 124 may be configured to be received by passageway 122 and to selectively provide fluid communication between first chamber 101 and the first fluid path 103. First member 124 may be shaped and sized so that there is a tight seal between the outer surface of the first member and the surface of passageway 122, while still allowing the first member to be rotated about its longitudinal axis L. First member 124 includes a first fluid path 103 having an inlet 115 and an outlet 116, inlet channel 105 in fluid communication with the first fluid path, and outlet channel 106 in fluid communication with the first fluid path.

As shown, first fluid path 103 has a variable diameter/width along its length, but in other embodiments, the first fluid path has a constant diameter/width along its length. Referring to FIG. 1C, for example, near inlet 115, the diameter/width of first fluid path 103 may be larger than the diameter/width near outlet 116. Without being bound by theory, the resistance along first fluid path 103 is generally determined by its shape, including the cross-sectional area and length. Having variable diameters/widths allows air flow resistance along first fluid path 103 to be controlled and allows a first restriction 107 (a length along the first fluid path with a reduced diameter/width) to be located downstream of inlet fluid channel 105 and around the junction of outlet fluid channel 106. As a result, the cross-sectional area of first restriction 107 may be smaller than the cross-sectional area of inlet channel 105, which may result in a larger proportion of the total mass flow exiting first fluid path 103 and diverting into first chamber 101. Changing these ratios may increase or decrease the mass flow rate through first chamber 101 and affect the velocity of the fluid flow into the first chamber from inlet channel 105. Higher fluid flow into first chamber 101 may result in more turbulence, shear and mechanical interaction of the drug and produce greater de-agglomeration and dispersion. The flow of fluid into first chamber 101 may also affect how much of the drug is removed from the first chamber and how quickly the drug leaves the first chamber. Furthermore, locating outlet channel 106 within the length of first restriction 107 may create a Venturi effect at the outlet (downstream) of the outlet channel, thereby helping to pull fluid out of first chamber 101 along the outlet channel. In some embodiments, first fluid path 103 increases in cross-sectional area upstream of outlet channel 106 to reduce resistance along the first fluid path and to increase (e.g., optimize) Venturi effects.

Moreover, the percentage of fluid flow through first chamber 101 may be controlled by varying the cross-sectional areas of inlet channel 105, outlet channel 106 and/or first restriction 107. For example, varying the cross-sectional areas of inlet channel 105 and outlet channel 106 may change the fluid velocity along each channel. High velocity fluid flow may be turbulent and may be beneficial for fluidizing and dispersing the drug in first chamber 101 and outlet channel 106.

As indicated above, inlet and outlet channels 105, 106 are capable of being in fluid communication with first chamber 101, depending on the rotational position of first member 124 relative to the first chamber. Referring to FIGS. 1A and 1B, in a closed position, inlet and outlet channels 105, 106 are blocked by housing 120, and there is no fluid communication between first chamber 101 and first fluid path 103. In an opened position, shown in FIGS. 1C and 1D, inlet and outlet channels 105, 106 are at least partially unblocked and in fluid communication with opening 111. As a result, first chamber 101 and first fluid path 103 are in fluid communication.

Device 100 may be provided in the closed position (FIGS. 1A and 1B). Rotating first member 124 and/or housing 120 relative to each other unblocks at least portions of inlet and outlet channels 105, 106 (e.g., FIGS. 1C and 1D). placing first chamber 101 and first fluid path 103 in fluid communication via channels 105, 106. The user then inhales through outlet 116 (e.g., passive) or flow may be provided actively or by a combination of passive and active flow (neither shown in FIGS. 1A-1D). As air is drawn from outlet 116, air moves from inlet 115 to the outlet. Air also flows through inlet channel 105, into and through first chamber 101, through outlet channel 106, into first fluid path 103, and through outlet 116. As the air moves through first chamber 101, the air re-circulates (path 118) within the first chamber, disperses the stored drug, and entrains the drug into the air stream. The drug is dispersed primarily through shear, vibration and turbulence. Drug carried by the re-circulating fluid stream is dispersed by contact with the wall of first chamber 101. In addition, the entrained drug moving from re-circulating fluid path 118 toward outlet channel 106 crosses air flowing from inlet channel 105 into first chamber 101, further dispersing the drug by shear and turbulence. Over time, the dispersed and entrained drug moves through outlet channel 106 and through outlet 116, where the drug is inhaled by the user. In some embodiments, outlet channel 106 has a radially curved air path (as viewed along axis L) that causes the entrained drug to contact the wall of the outlet channel. Alternatively or additionally, to disperse the drug further, the geometry of inlet channel 105 may be modified to direct incoming air to selected portions of first chamber 101. For example, air may be directed substantially tangentially to the wall of first chamber 101, towards outlet channel 106, away from the outlet channel, or in a curved path similar to re-circulating fluid path 118.

In other embodiments, device 100 may be configured to keep the drug isolated in first chamber 101. Preventing the drug from moving out of first chamber 101 prior to use (e.g., due to movement during shipping) may optimize the amount of drug to be dispersed, fluidized and/or metered from the first chamber. FIG. 1H shows a device 100' in a closed position, and FIG. 1I shows the device in an opened position. Device 100' is similar to device 100 but further includes a protrusion 134 on first member 124 configured to seal opening 111 and to separate first chamber 101 from volume 138. Protrusion 134 may be disengaged from obstruction 104 and opening 111 by rotating first member 124 relative to housing 120, thereby allowing first chamber 101 to fluidly communicate with volume 138 and first path 103. The drug may be delivered to the user as described above.

In some embodiments, device 100 does not include a first restriction 107. In other embodiments, first fluid path 103 does not extend continuously along longitudinal axis L. When the user inhales through outlet 116, air flows through inlet 115, through a first portion of a first fluid path, through inlet channel 105, into first chamber 101 (where it re-circulates and eventually leaves), through outlet channel 106, through a second portion of the first fluid path not directly in fluid communication with the first portion, and out the outlet. In other words, air cannot flow directly from inlet 115 to outlet 116, but the air must flow through first chamber 101.

Figure 1J:
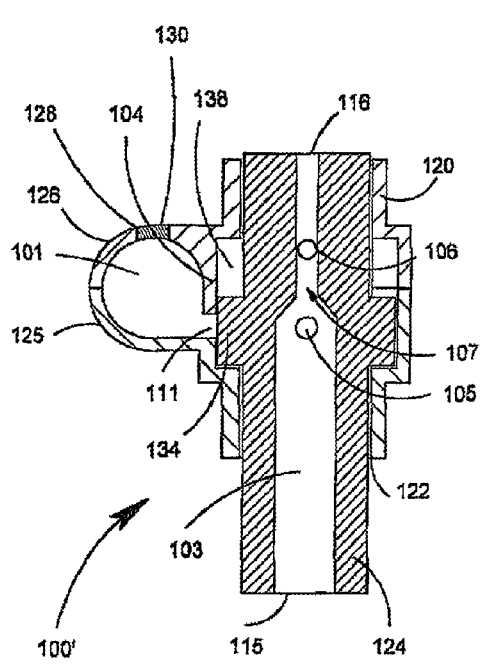
FIG. 1J is a cross-sectional diagram similar to FIG. 1D of an embodiment of a drug delivery device.
Figure 1J:
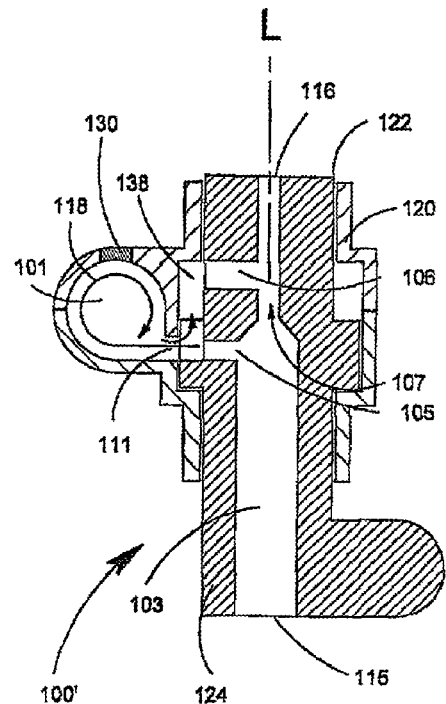
Figure 1J:
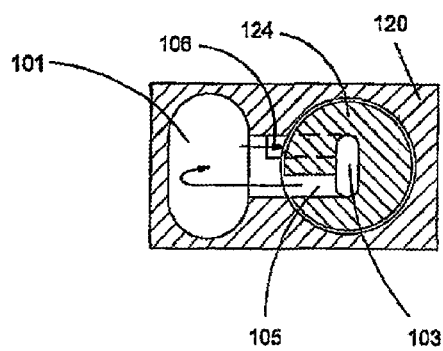

Similarly, other features of a device may be modified. For example, FIG. 1J shows modifications to first fluid path 103, inlet channel 105 and outlet channel 106. The cross section of first fluid path 103 may be circular or non-circular (e.g., racetrack (as shown), oval, elliptical, irregularly curved, irregularly or regularly polygonal having three, four, five, six, seven or eight more sides). As viewed down longitudinal axis L, inlet and outlet channels 105, 106 may overlap with each other (as shown), partially overlap, or not overlap at all.

Figure 2A:
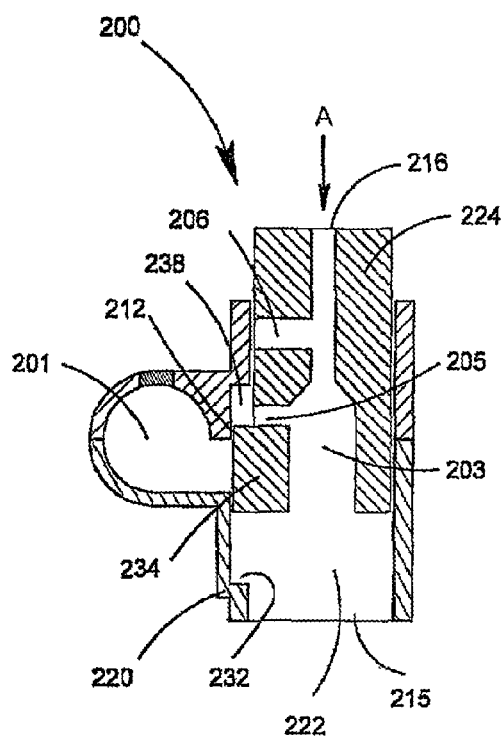
FIG. 2A is a cross-sectional schematic diagram of an embodiment of a drug delivery device in a closed position.
Figure 2B:
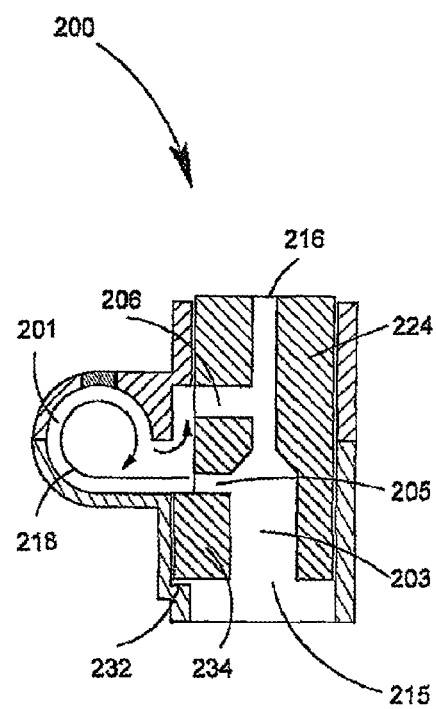
FIG. 2B is a cross-sectional schematic diagram of the device shown in FIG. 2A in an opened position.

While first member 124 and housing 120 are configured to rotate relative to each other, in other embodiments, the first member and the housing are configured to translate relative to each other. FIGS. 2A and 2B show a drug delivery device 200 that includes similar structural features as device 100 shown in FIG. 1A. (Similar structural features are labeled with the same reference numerals from FIGS. 1A and 1B, but the first "1" is replaced with a "2".) FIG. 2A shows device 200 in a closed position, and FIG. 2B shows the device in an opened position. Drug delivery device 200 includes a housing 220 having a passageway 222, and a first member 224 located and capable of translating within the passageway. Housing 220 is similar to housing 120 but further includes a stop 232 configured to restrict translation of first member 224 at a predetermined location. First member 224 is similar to first member 124 but further includes a protrusion 234 that provides a tight seal 212 between the outer surface of the protrusion and the surface of passageway 222 to prevent contamination of the drug in first chamber 201 (FIG. 2A). Protrusion 234 also promotes retaining the drug to first chamber 201 and may prevent the drug from moving to volume 238 (e.g., during transport). As a result, the dispersion, fluidization, and/or metering of drug from first chamber 201 may be optimized. Like inlet and outlet channels 105, 106, inlet and outlet channels 205, 206 are not in fluid communication with first chamber 201 when device 200 is in the closed position.

Device 200 may be provided in the closed position (FIG. 2A). The device may be put in the opened position by translating first member 224 and/or housing 220 relative to each other (e.g., by pushing the first member into the housing (arrow A)). The translation removes seal 212 between protrusion 234 and passageway 222 in the vicinity of first chamber 201 and puts at least portions of inlet and outlet channels 205, 206 in fluid communication with first chamber 201 (e.g., FIG. 2B). As a result, first chamber 201 and first fluid path 203 are in fluid communication via channels 205, 206. Inlet and outlet channels 205, 206 are unblocked when first member 224 contacts stop 232, which may prevent first member 224 from translating any further along direction A. The user then inhales through outlet 216. As air is drawn from outlet 216, air moves from inlet 215 to the outlet. Air also flows through inlet channel 205, into and through first chamber 201, through outlet channel 206, into first fluid path 203, and through outlet 216. As the air moves through first chamber 201, the air re-circulates (path 218) within the first chamber, disperses the stored drug, and entrains the drug into the air stream. The drug may be dispersed primarily through shear, vibration and turbulence. Drug carried by the re-circulating fluid stream may be dispersed by contact with the wall of first chamber 201. In addition, the entrained drug moving from re-circulating fluid path 218 toward outlet channel 206 crosses air flowing from inlet channel 205 into first chamber 201, further dispersing the drug by shear and turbulence. Over time, the dispersed and entrained drug moves through outlet channel 206 and through outlet 216, where the drug may be inhaled by the user. In some embodiments, outlet channel 206 has a radially curved air path that causes the entrained drug to contact the wall of the outlet channel. Inlet channel 205 may be modified like inlet channel 105 to direct incoming air to selected portions of first chamber 201.

In other embodiments, housing 220 does not include stop 232. For example, first member 224 may be translated by a plunger having a stop (see, e.g., FIG. 16A) that moves the first member to a point where first chamber 201 and first fluid path 203 are in fluid communication via channels 205, 206, and no further.

Figure 3:
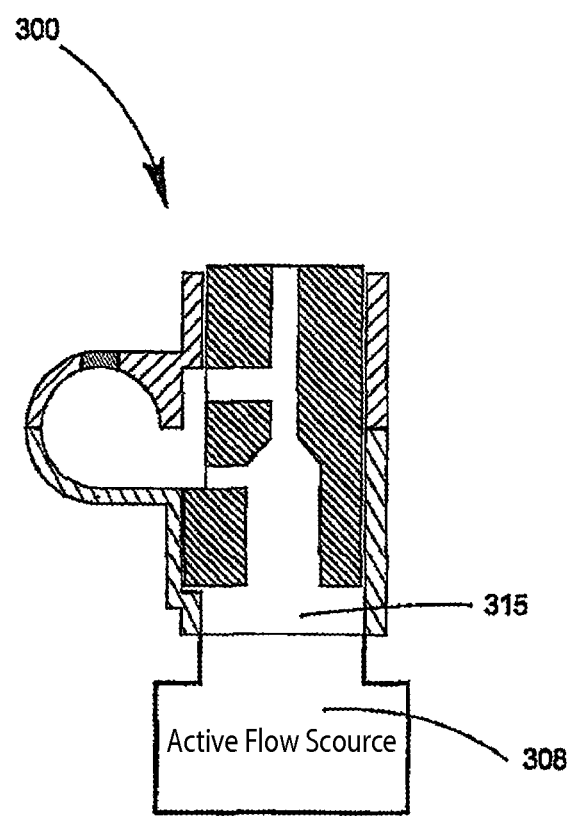
FIG. 3 is a cross-sectional schematic diagram of the device shown in FIG. 2B including an active flow source to assist in drug dispersion.
Figure 5A:
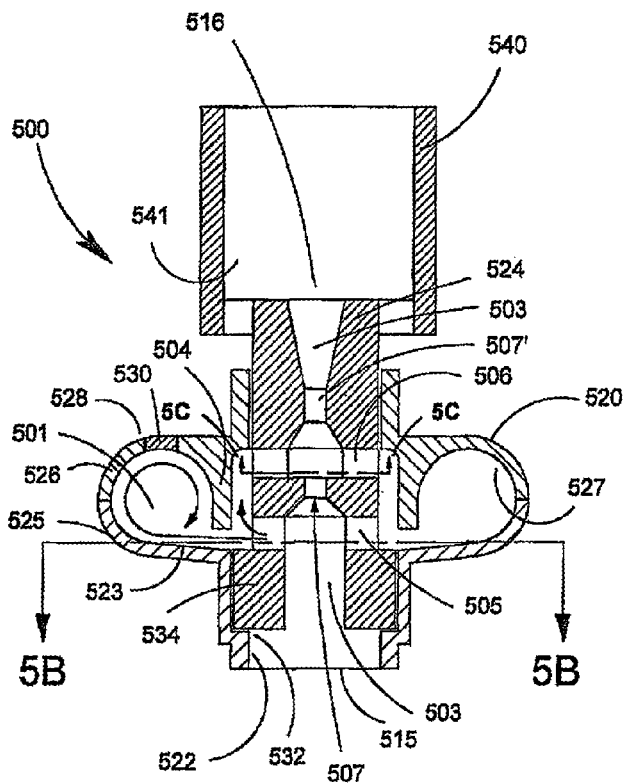
FIG. 5A is a cross-sectional schematic diagram of an embodiment of a drug delivery device in an opened position.
Figure 5B:
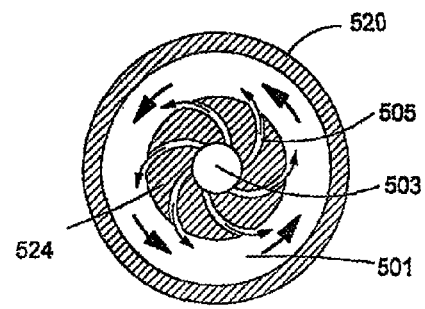
FIG. 5B is a cross-section of the device shown in FIG. 5A, taken along line 5B-5B.
Figure 5C:
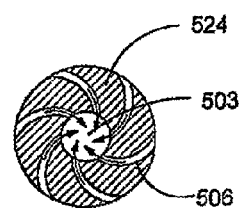
FIG. 5C is a cross-section of the device shown in FIG. 5A, taken along line 5C-5C.
Figure 5D:
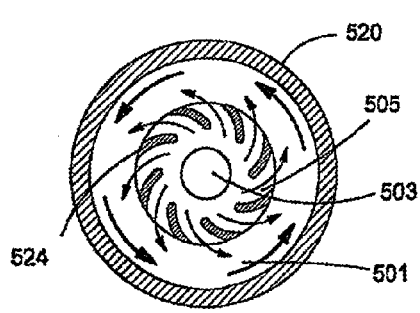
FIG. 5D is a cross-section similar to FIG. 5B of an embodiment of a drug delivery device.
Figure 5E:
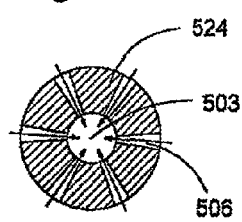
FIG. 5E is a cross-section similar to FIG. 5C of an embodiment of a drug delivery device.
Figure 5F:
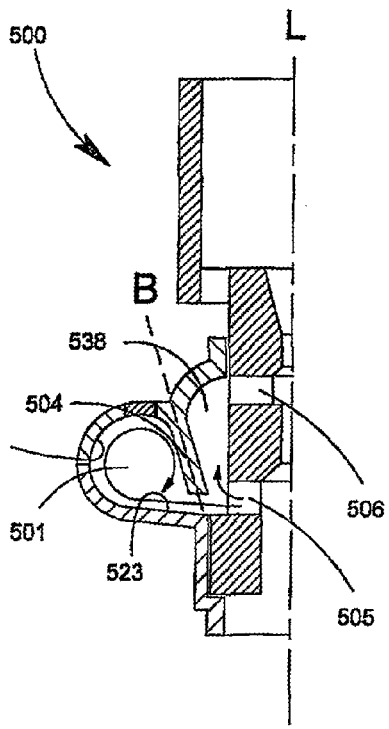
FIG. 5F is a partial a cross-sectional schematic diagram of an embodiment of a drug delivery device.

FIG. 3 shows a drug delivery device 300 similar to drug delivery device 200 shown in FIGS. 2A and 2B and further including an active fluid flow source 308. (Similar structural features are labeled with the same reference numerals from FIGS. 2A and 2B, but the first "2" is replaced with a "3". Similar numbering schemes are used below for other embodiments.) Active fluid flow source 308 is configured to engage with inlet 315 and to assist in dispersion during drug delivery. Examples of source 308 include a compressed fluid (e.g., air) and a gas mover (e.g., a fan, a bellows, a squeeze bulb, and/or a pump). In some embodiments, the active device includes a propellant that does not cause environmental damage. Active fluid flow source 308 may be incorporated in drug delivery device 100 (shown in FIGS. 1A and 1B) and any other devices described herein.

In some embodiments, a first chamber described above (FIGS. 1A-1J, 2A-2B and 3) may extend around a perimeter of a first member. For example, like embodiments described below, a device may include a first chamber having a continuous volume (such as a torus) extending around a perimeter of a first member. A device may also include multiple, discontinuous first chambers arranged around a perimeter of a first member. In other embodiments, a drug delivery device may have other configurations for a housing and a first member. As an example, referring to FIGS. 4A and 4B, a drug delivery device 400 includes a housing 420 having an annular first chamber 401 and a passageway 422, and a first member 424 configured to be received by the passageway. First member 424 and housing 420 may translate relative to each other along the longitudinal axis of passageway 422. FIG. 4A shows device 400 in the closed position, and FIG. 4B shows the device in the opened position.

Housing 420 shares similar features with housing 220 (FIGS. 2A and 2B). As shown, housing 400 includes two moisture impervious parts 425, 426 that join to define passageway 422 and annular first chamber 401, and an opening 428 in fluid communication with the first chamber. First chamber 401 may be loaded with a drug through opening 428, which may be subsequently covered with a plug 430. Similar to housing 220, housing 420 includes a stop 432 at a predetermined location and configured to restrict translation of first member 424 relative to the housing.

As shown, first chamber 401 may be toroidal in shape and lies in a plane transverse (as shown, perpendicular) to the longitudinal axis (L') of first member 424. Like first chamber 101, first chamber 401 has a metering geometry configured to prevent the drug from leaving device 400 as large clump(s) and to help fluidize the drug. For example, the metering geometry has an obstacle 404 configured to slow the egress of the drug from first chamber 401. First chamber 401 may be configured as first chamber 101 described above. Furthermore, while first chamber 401 is shown as a continuous torus, in other embodiments, device 400 includes multiple (e.g., two, three, four, five, or six or more) discontinuous first chambers arranged (e.g., circumferentially) around first member 424. These discontinuous first chambers may fluidly communicate with each other via channels of first member 424.

First member 424 is similar to first member 224. For example, first member 424 includes a protrusion 434 that provides a tight seal 412 between the outer surface of the protrusion and the surface of passageway 422 to prevent contamination of the drug and to prevent the drug from leaving first chamber 401 (FIG. 4A). Referring to FIGS. 4C and 4D, first member 424 further includes multiple (as shown, six) inlet and outlet channels 405, 406 capable of being in fluid communication with first fluid path 403 and first chamber 401. When device 400 is in the closed position (FIG. 4A), first chamber 401 may be tightly blocked by protrusion 434 and does not fluidly communicate with inlet and outlet channels 405, 406 or first fluid path 403. When device 400 is in the opened position (FIG. 4B), inlet and outlet channels 405, 406 are in fluid communication with first fluid path 403 and first chamber 401. Having multiple fluid channels helps evenly distribute the drug from first chamber 401 into first fluid path 403. As shown, inlet and outlet channels 405, 406 extend generally in a radial array around first fluid path 403. Referring to FIGS. 4B and 4C, inlet fluid path 405 may direct fluid flow to create a circumferential flow 419 direction in addition to a re-circulating cross-sectional flow pattern 418 (FIG. 4B), thereby helping to fluidize the drug contained within first chamber 401. Furthermore inlet channels 405 may be shaped to optimize the circumferential fluid flow. Inlet and outlet channels 405, 406 may have a straight shape, a curved shape, or combinations of shapes. The percentage of fluid flow through first chamber 401 may be controlled by varying the cross sectional areas of inlet channel 405, outlet channel 406 and/or first restriction 407. In embodiments in which device 400 includes multiple discontinuous first chambers, inlet and outlet channels 405, 406 are constructed and arranged to fluidly communicate with the first chambers when the device is in the opened position.

Still referring to FIGS. 4A and 4B, device 400 further includes a mouthpiece 440 connected (e.g., unitarily formed with) first member 424. As shown, mouthpiece 440 includes fluid bypasses 441 that allow fluid (e.g., fresh air) to flow around the drug exiting first member 424. The bypasses may be formed unitarily in the mouthpiece, according to some embodiments. The air flowing through bypasses 441 may prevent the drug from sticking to mouthpiece 440 and may enhance delivery of the drug into the lungs. Varying the cross sectional area of bypasses 441 may change the flow characteristics through first fluid path 403. The cross sectional shape of bypasses 441 may take many shapes and be varied to concentrate the volumetric fluid flow to a specific area.

In use, device 400 may be provided in the closed position (FIG. 4A). The device may be put in the opened position by translating first member 424 and/or housing 420 relative to each other (e.g., by pushing the first member into the housing (arrow B)). The translation removes seal 412 between protrusion 434 and passageway 422 in the vicinity of first chamber 401 and puts at least portions of inlet and outlet channels 405, 406 in fluid communication with first chamber 401 (e.g., FIG. 4B). As a result, first chamber 401 and first fluid path 403 are in fluid communication via channels 405, 406. Inlet and outlet channels 405, 406 are unblocked when protrusion 434 contacts stop 432, which may prevent first member 424 from translating any further along direction B. The user then inhales through outlet 416. As air is drawn from outlet 416, air moves from inlet 415 to the outlet. Air also flows through inlet channels 405, into and through first chamber 401 by capillary action (FIG. 4C), through outlet channels 406, into first fluid path 403 (FIG. 4D), and through outlet 416. As the air moves through first chamber 401, the air re-circulates within the first chamber, disperses the stored drug, and entrains the drug into the air stream. The drug may be dispersed primarily through shear, vibration and turbulence. Drug carried by the re-circulating fluid stream may be dispersed by contact with the wall of first chamber 401. In addition, the entrained drug moving from a re-circulating fluid path 418 toward outlet channels 406 crosses air flowing from inlet channels 405 into first chamber 401, further dispersing the drug by shear and turbulence. Over time, the dispersed and entrained drug moves through outlet channels 406, through outlet 416, and through mouthpiece 440 where the drug may be inhaled by the user. In other embodiments, the user inhales while putting device 400 into its opened position. Such a simultaneous inhalation and opening operation may be applied with all embodiments described herein.

In other embodiments, referring to FIG. 4E, obstacle 404 includes one or more features 409 (such as slots, indentations, grooves, openings, and/or holes) that help meter the drug and prevent large particles of the drug from exiting the first chamber.

FIGS. 5A, 5B, 5C, 5D, 5E and 5F show exemplary modifications to device 400 that enhance dispersion and metering of the drug. FIGS. 5A, 5B and 5C show a device 500 similar to device 400 in which analogous features are numbered analogously. Device 500 includes a surface 523 of a first chamber 501 that slopes relative to a direction of inlet channels 505 so that fluid flow may be directed from the inlet channels, toward the drug, and toward a far wall 527 of the first chamber. Sloping the surface of first chamber 501 may prevent the drug from sticking to a flat surface (i.e., coplanar with the direction of inlet channels 505) and enhances complete delivery of the drug. In some embodiments, the slope of the surface of first chamber 501 may be approximately 1 degree to approximately 30 degrees from the direction of inlet channels 505. Surface 523 may be flat (e.g., having a generally constant slope) or curved. Device 500 further includes a first fluid path 503 that varies in cross-sectional diameter to control the fluid flow resistance through the first fluid path. As shown, first fluid path 503 includes a first restriction 507 intermediate inlet channels 505 and outlet channels 506, a second restriction 507' intermediate the outlet channels and outlet 516, and an enlarged diameter outlet end (e.g., a cone having an angel of approximately one degree to approximately 30 degrees).

Inlet and outlet channels 505, 506 may also be modified to control fluid flow into and out of first chamber 501. As shown in FIGS. 5B and 5C, inlet and outlet channels 505, 506 may be radially curved in the same direction. In other embodiments, channels 505, 506 may be radially curved in different directions, or some channels may curve in the same direction while other channels curve in different directions. FIG. 5D shows an embodiment in which more material has been removed from first member 524 to create inlet channels 505 having a fan-like configuration. A similar modification may be performed for outlet channels 506. FIG. 5E shows an embodiment in which outlet channels 506 are radially straight. The width of channels may be constant or varied (e.g., decreasing from first chamber 501 to first fluid path 503 (as shown in FIG. 5E) or increasing from the first chamber to the first fluid path). A similar modification may be performed for inlet channels 505.

FIG. 5F shows a modification to volume 538 designed to slow the egress of the drug into outlet channels 506. As shown, volume 538 enlarges in cross-sectional area as it extends from inlet channels 505 to outlet channels 506. In other embodiments, the cross-section area of volume 538 may be substantially constant (e.g., as shown in FIG. 5A). Volume 538 may be discrete channels (e.g., in embodiments having multiple unconnected first chambers located around a first member) or a circumferential ring extending around the first member and having different cross sections. Volume 538 acts to disperse the drug further, for example, by centrifugal force that keeps large drug particles tumbling against the wall of the volume where they break into smaller particles that may be carried by the fluid flow. As shown, obstacle 504 may be configured to divert at least some air coming from inlet channel 505 into volume 538. This diverted air helps to increase turbulence in volume 538 to dislodge and to disperse any drug that may be in the volume. Obstacle 504 may have a longitudinal axis B that may be substantially parallel or acute to the longitudinal axis L of device 500.

Figure 6A:
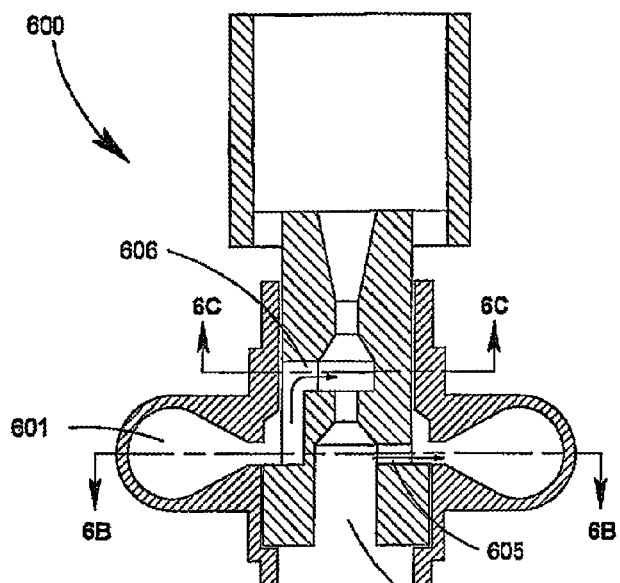
FIG. 6A is a cross-sectional schematic diagram of an embodiment of a drug delivery device in an opened position.
Figure 6D:
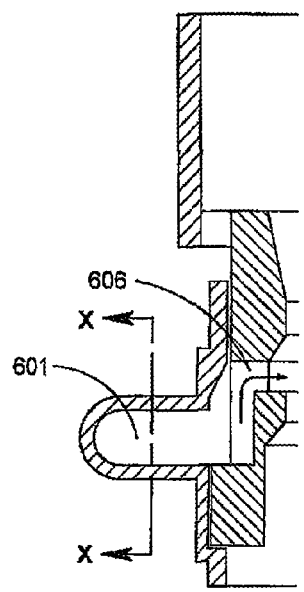
FIG. 6D is a partial cross-sectional schematic diagram of an embodiment of a drug delivery device.
Figure 6B:
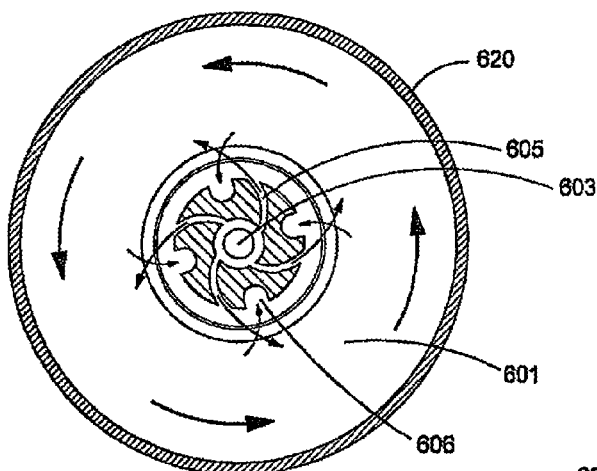
FIG. 6B is a cross-section of the device shown in FIG. 6A, taken along line 6B-6B.
Figure 6E:
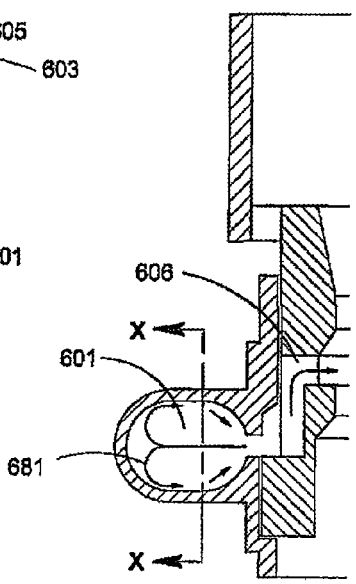
FIG. 6E is a cross-sectional schematic diagram of an embodiment of a drug delivery device.
Figure 6C:
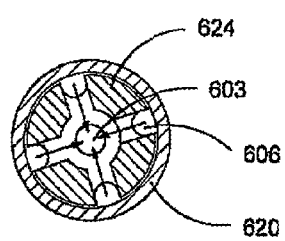
FIG. 6C is a cross-section of the device shown in FIG. 6A, taken along line 6C-6C.

FIGS. 6A, 6B, and 6C show a drug delivery device 600 designed to get the drug to collect on the outside wall (i.e., the radially far wall as viewed down the longitudinal axis of the device) of a first chamber 601. As fluid flows through inlet channels 605 and into first chamber 601, the fluid moves in a circular motion around a first fluid path 603, peels off the exposed surface layer of the drug and allows the drug to move toward outlet channels 606 while generally crossing incoming fluid from the inlet channels. As shown, first chamber 601 has a tear-drop cross section that enlarges from inlet and outlet channels 605, 606 to a radially far wall and in which opposing wall portions diverge. The cross section of first chamber 601 perpendicular to the tear-drop cross section may be circular or non-circular. In other embodiments, referring to FIG. 6D, first chamber 601 includes opposing parallel walls and a curved, closed radially far end. First chamber 601 may also include opposing parallel walls, a curved, closed radially far end, and a curved, opened radially near end (as shown in FIG. 6E). In the embodiments shown in FIGS. 6A and 6E, air incoming from inlet channel 605 may be introduced along a line of symmetry into first chamber 601 to disperse and to circulate (path 681) the drug in the first chamber substantially symmetrically. Still referring to FIGS. 6D and 6E, the cross section taken along line X-X may be circular or non-circular.

Figure 7A:
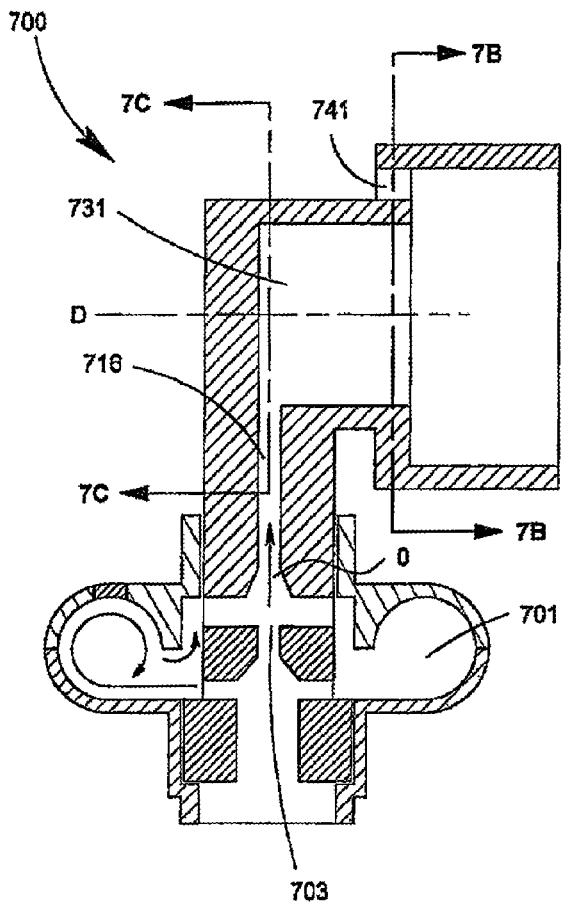
FIG. 7A is a cross-sectional schematic diagram of an embodiment of a drug delivery device in opened position.
Figure 7B:
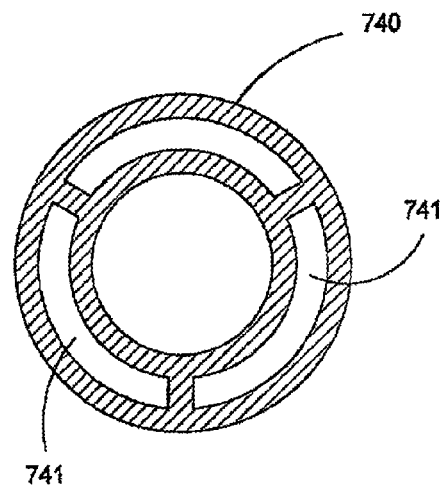
FIG. 7B is a cross-section of the device shown in FIG. 7A, taken along line 7B-7B.
Figure 7C:
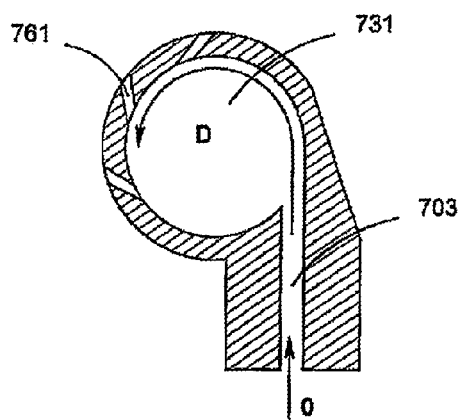
FIG. 7C is a cross-section of the device shown in FIG. 7A, taken along line 7C-7C.

In other embodiments, fluid flow exiting an outlet enters volumes having different configurations. FIGS. 7A, 7B, and 7C show a device 700 similar to device 400 (FIG. 4A), except that fluid flow exiting an outlet 716 flows into a second dispersion chamber 731 configured to disperse the drug further (since first chamber 701 is effectively a first dispersion chamber). Second dispersion chamber 731 has a longitudinal axis D that is transverse to (as shown, perpendicular to) the direction of fluid flow leaving outlet 716 (direction 0), as shown, axis D is perpendicular to direction O. More specifically, referring to FIG. 7C, fluid flow exiting a first fluid path 703 enters second dispersion chamber 731 tangentially to a cross section of the second chamber to re-circulate and to further disperse a drug in the dispersion chamber. As shown, the cross section of second dispersion chamber 731 may be generally circular, but in other embodiments, the cross section may be non-circular (e.g., oval, elliptical, and polygonal).

During use, as the drug is entrained in first fluid path 703, the drug travels toward second dispersion chamber 731 and mouthpiece 740. When the drug enters second dispersion chamber 731, it strikes and moves along the walls of the second dispersion chamber and disperses further before exiting the second dispersion chamber. As shown, mouthpiece 740 may include unitarily formed bypasses 741 that allow fluid to flow around the drug exiting second dispersion chamber 731. Varying the cross sectional area of bypasses 741 may change the flow characteristics through first fluid path 703 and second dispersion chamber 731. The cross-sectional shape(s) of bypasses 741 may take many shapes and be varied to concentrate the volumetric fluid flow to a selected area. Second dispersion chamber 731 may have walls that are parallel to its longitudinal axis (FIG. 7A). or, as shown in FIG. 7D, the walls may converge downstream along the longitudinal axis and create enhanced dispersion before the drug exits the dispersion chamber by increasing contact with the walls of the dispersion chamber.

In other embodiments, referring to FIG. 7C, dispersion chamber 731 includes air inlets or vents 761, similar to bypasses 741, that provide air to further disperse the drug as it travels through the dispersion chamber and to enhance delivery of the drug to the lungs.

In some embodiments, a drug delivery device, such as the embodiments described above, may be enclosed in a second chamber, and the device may be configured to open the second chamber internally. FIGS. 8A and 8B show a device 800 having similar features to device 400 (FIGS. 4A and 4B), with FIG. 8A showing the device in the closed position and FIG. 8B showing the device in the opened position. Device 800 includes a housing 820, a first member 824 received by the housing, a second chamber 850 that encloses the housing and the first member, a mouthpiece 840 that engages a recess 842 of the second chamber via an outlet ring 852, and a base 854 that engages a second portion of the second chamber (as shown, opposing the first portion). In some embodiments, second chamber 850 includes an additional recess configured to engage base 854.

Housing 820 and first member 824 are similar to housing 420 and first member 424 (FIG. 4A), respectively, but further include features for internally opening second chamber 850. Similar to housing 420, housing 820 includes a toroidal first chamber 801 for storing a drug, a passageway 822 for receiving first member 824, and a stop 832, but housing 820 further includes a cutting edge 856 configured to puncture second chamber 850, and a shoulder 858 configured to engage base 854. Like first member 424, first member 824 includes inlet and outlet channels 805, 806, a first fluid path 803, and a protrusion 834, but first member 824 further includes a cutting edge 860 configured to puncture second chamber 850, and a shoulder 862 configured to engage outlet ring 852 (described below). Housing 820 and first member 824 are configured to translate relative to each other, like housing 420 and first member 424.

Second chamber 850 may be configured to provide the drug in first chamber 801 with additional protection and to be punctured by housing 820 and first member 824 during use. Referring also to FIGS. 23A and 23B, second chamber 850 may be generally shaped to provide device 800 with strength and structural integrity, while also being able to deform (e.g., crushed in an axial direction B) in a predictable and controllable manner during use (FIG. 23B). As shown, second chamber 850 includes a first curved portion 857 and a second curve portion 859 that forms a circular groove around a generally flat portion 879. The groove may engage with outlet ring 852. In other embodiments, referring to FIG. 23C, a second chamber 850' does not include a flat portion. In some embodiments, second chamber 850 includes two layers of a moisture impervious material, such as a plastic coated foil. The layers of material may be pre-formed to create second chamber 850 when they are attached together. As shown, the layers have a formed step 864 with a recess 842 (e.g., a circular groove or a series of grooves in a pattern corresponding to outlet ring 852) that interfaces with outlet ring 852, and a formed step 866 that interfaces with base 854. Second chamber 850 further includes a stabilizing feature 851 that locates and stabilizes housing 820 at a selected position inside the second chamber. Stabilizing feature 851 also keeps cutting edges 856, 860 from contacting or puncturing second chamber 850 until the second chamber may be deformed during use. As shown, stabilizing feature 851 (such as an annular ring, one or more ribs, or a tab) may be formed by the layers of second chamber 850 and interfaces with a corresponding feature 853 (such as a protruding tab) of housing 820. In other embodiments, stabilizing feature 851 and/or feature 853 are separate components that attach to second chamber 850 and housing 820, respectively. Outlet ring 852 and/or base 854 may be attached or unattached to second chamber 850.

Device 800 may be provided to the user in the closed position (FIG. 8A). Protrusion 834 provides a tight annular seal between first member 824 and passageway 822, and may prevent fluid communication into first chamber 801, which stores a drug. The drug may be further protected (e.g., from moisture and/or air) by second chamber 850.

To use device 800, pressure is applied to base 854 and mouthpiece 840 in opposite directions to move the base and the mouthpiece toward each other. The applied pressure may be transferred to formed steps 864, 866 of second chamber 850 and causes the second chamber to move toward cutting edges 856, 860, which puncture the second chamber. Portions of second chamber 850 that are punctured remain attached to the second chamber and deform in a controlled manner (e.g., like a bellows) such that the punctured portions do not block fluid flow path 803. As a result, first fluid path 803 of first member 824 is opened to fluid communication to mouthpiece 840 and base 854. Second chamber 850 continues to deform to allow relative movement of base 854 and mouthpiece 840.

As base 854 and mouthpiece 840 continue to move toward each other, outlet ring 852 eventually contacts shoulder 862, and the base eventually contacts shoulder 858. Continued movement of base 854 and mouthpiece 840 toward each other causes first member 824 and housing 820 to translate relative to each other, and eventually to place inlet and outlet channels 805, 806 and first fluid path 803 in full fluid communication with first chamber 801, generally as described above for device 400. Device 800 is now in the opened position (FIG. 8B). In other embodiments, depending on the applied forces and friction, second chamber 850 is punctured after inlet and outlet channels 805, 806 and first fluid path 803 are placed in full fluid communication with first chamber 801.

The user then inhales through mouthpiece 840, and the drug in first chamber 801 is delivered through the mouthpiece as described above for device 400. In some embodiments, as shown in FIGS. 8A and 8B, mouthpiece 840 includes a unitarily formed fluid bypass 841 that allows fluid to flow around the drug exiting first member 824, as described above for bypass 441.

Figure 9A:
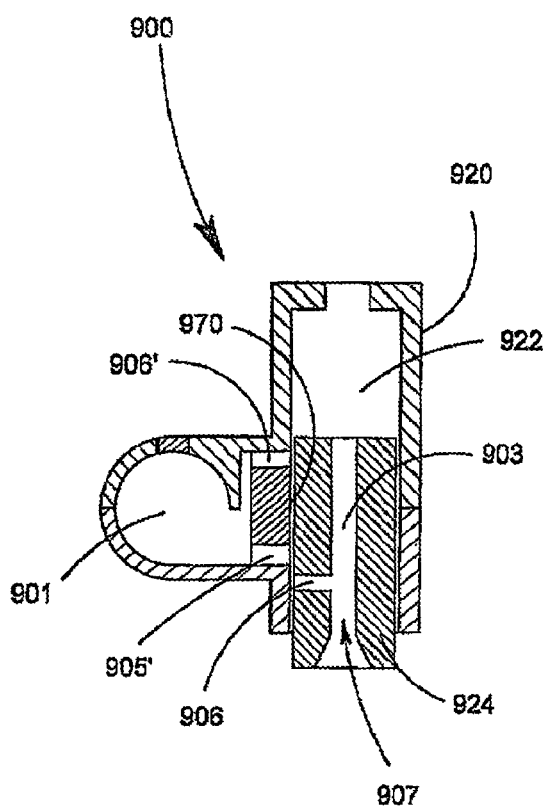
FIG. 9A is a cross-sectional schematic diagram of an embodiment of a drug delivery device in a closed position.
Figure 9B:
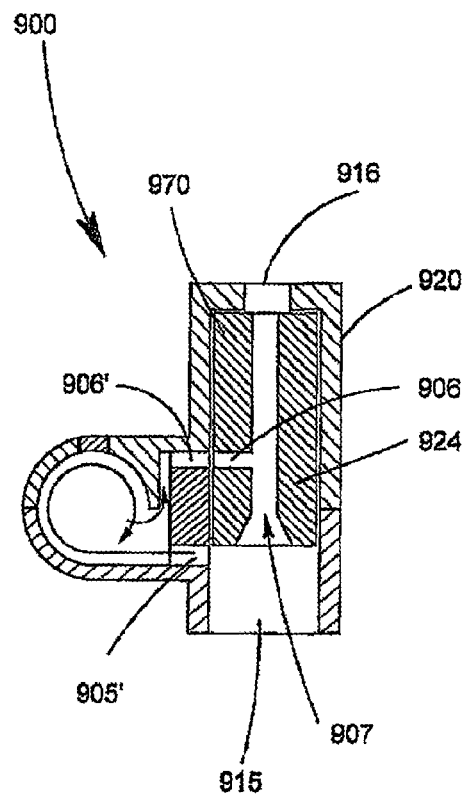
FIG. 9B is a cross-sectional schematic diagram of the device shown in FIG. 9A in an opened position.

While the embodiments described above are shown as having a housing including one opening to a first chamber (which stores a drug), in other embodiments, the housing includes multiple openings to the first chamber. FIGS. 9A and 9B show a drug delivery device 900 having a housing including multiple openings to a first chamber. FIG. 9A shows device 900 in the closed position, and FIG. 9B shows the device in the opened position.

As shown, device 900 includes a housing 920 having similar features as housing 220 (FIG. 2A) and including additional features. Housing 920 includes a passageway 922 that receives a first member 924, and a first chamber 901 that stores a drug. Housing 920 further includes an inlet channel 905' and an outlet channel 906', which are unitarily formed with the housing.

Device 900 further includes a first member 924 configured to be received in passageway 922 of housing 920. First member 924 has a solid portion 970 capable of tightly sealing inlet and outlet channels 905', 906', while allowing first member 924 and housing 920 to translate relative to each other during use. First member 924 includes a first fluid path 903 and an outlet channel 906 capable of aligning with outlet channel 906' to provide fluid communication between first chamber 901 and first fluid path 903. As shown, first fluid path 903 has a restriction 907 along the length of the first fluid path.

In use, device 900 may be provided to the user in the closed position (FIG. 9A), and the user translates first member 924 and/or housing 920 relative to each other to unseal inlet and outlet channels 905', 906' and to place first chamber 901 in fluid communication with first fluid path 903 (FIG. 9B). The user then inhales through an outlet 916. As fluid moves from an inlet 915 towards outlet 916, fluid also flows into first chamber 901 and entrains the drug into the fluid stream. The entrained drug may be delivered through outlet 916 as described for device 200. The percentage of fluid flow into and through first chamber 901 may be controlled by varying the cross sectional areas of inlet channel 905', outlet channel 906' and/or first restriction 907.

Figure 10:
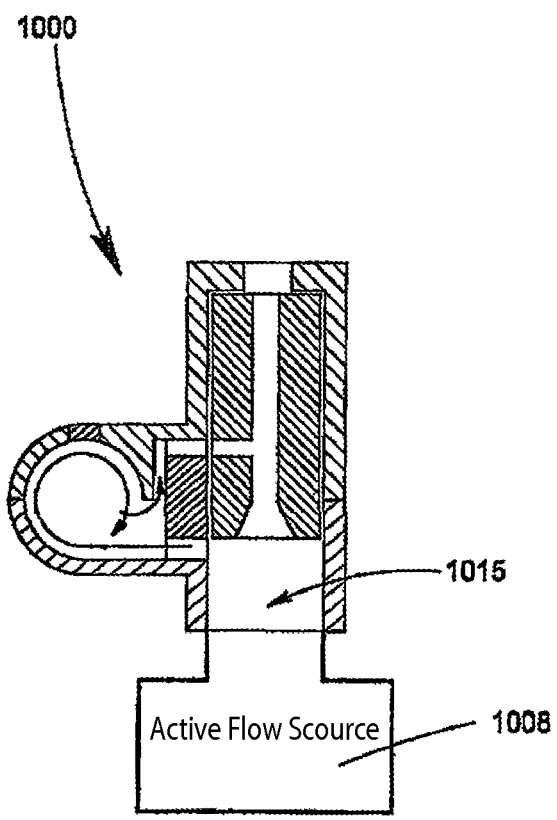
FIG. 10 is a cross-sectional schematic diagram of the device shown in FIG. 9B including an active flow source to assist in drug dispersion.

FIG. 10 shows a drug delivery device 1000 similar to drug delivery device 900 shown in FIGS. 9A and 9B and further including an active fluid flow source 1008. Active fluid flow source 1008 may be configured to engage with inlet 1015 and to assist in dispersion during drug delivery. Examples of source 1008 are provided above.

Device 900 may be modified to include a toroidal first chamber for drug storage, and to be enclosed in a second chamber. FIG. 11A shows a drug delivery device 1100 in a closed position, and FIG. 11B shows the device in an opened position. As shown, device 1100 includes a housing 1120, a first member 1124 received by the housing, a second chamber 1150 that encloses the housing and the first member, a mouthpiece 1140, and a plunger 1175 having a cutting tip. In some embodiments, plunger 1175 includes an open-ended passageway to provide fluid communication into housing 1120.

Housing 1120 is similar to housing 920. Housing 1120 includes a toroidal first chamber 1101 (e.g., FIGS. 4A and 8A), a passageway 1122 that receives first member 1124, and multiple sets of curved inlet channels 1105' and outlet channels 1106' that fluidly communicate with first chamber 1101. Curved inlet and outlet channels 1105', 1106' are unitarily formed with housing 1120, as shown, but may comprises separate components in other embodiments. Rather than having one continuous toroidal first chamber 1101, as shown, in other embodiments, device 1100 includes multiple discontinuous first chambers arranged around a first member 1124 that are capable of fluidly communicating with a first fluid path 1103 via multiple sets of unitarily formed inlet and outlet channels.

First member 1124 is similar to first member 924 (FIG. 9A) and configured to be received in passageway 1122 of housing 1120. First member 1124 has a solid portion 1170 capable of tightly sealing inlet and outlet channels 1105', 1106', while allowing first member 1124 and housing 1120 to translate relative to each other during use. First member 1124 includes first fluid path 1103 and outlet channels 1106 capable of aligning with outlet channels 1106' to provide fluid communication between first chamber 1101 and first fluid path 1103. First fluid path 1103 has a restriction 1107 from a first width/diameter to a second, smaller width/diameter along the length of the first fluid path. At a downstream end, first member 1124 also includes a cutting edge 1160 configured to puncture second chamber 1150.

Second chamber 1150 may be configured to provide the drug in first chamber 1101 with additional protection and to be punctured by cutting edge 1160 of first member 1124 during use. In some embodiments, second chamber 1150 includes two layers of a moisture impervious material, such as a plastic coated foil. The layers of material may be preformed to create second chamber 1150 when they are attached together. Furthermore, the layers have a formed step 1164 that interfaces with mouthpiece 1140, and a formed step 1166 that interfaces with plunger 1175.

Mouthpiece 1140 may be configured to engage with an outlet end of housing 1120, and plunger 1175 may be configured to engage with an inlet end of first member 1124, as described below. As shown, mouthpiece 1140 includes unitarily formed fluid bypasses 1141 that allow fluid to flow around the drug flowing through the mouthpiece. Varying the cross sectional area of bypasses 1141 may change the flow characteristics through first fluid path 1103. The cross sectional shape of bypasses 1141 may take many shapes and be varied to concentrate the volumetric fluid flow to a specific area.

Device 1100 may be provided in a closed position (FIG. 11A). The drug in first chamber 1101 may be protected (e.g., from moisture and/or air) by solid portion 1170 of first member 1124, which tightly seals inlet and outlet channels 1105', 1106' and may prevent movement of the drug out of the first chamber. The drug may be also protected by second chamber 1150.

In use, mouthpiece 1140 engages outlet end of housing 1120, plunger 1175 engages an inlet end of first member 1124, and the mouthpiece and the plunger are moved toward each other in opposing directions. As plunger 1175 moves toward first member 1124 and into second chamber 1150, the plunger punctures formed step 1166 and translates the first member relative to housing 1120, thereby removing the tight seal blocking inlet and outlet channels 1105', 1106'. Eventually cutting edge 1160 of first member 1124 punctures step 1164, and outlet channels 1106 of the first member align with outlet channels 1106' of housing 1120. Plunger 1175 is then withdrawn from housing 1120, or if the plunger includes an air passageway, the plunger may be kept in place. Device 1100 is in an opened position (FIG. 11B) in which first chamber 1101 is in fluid communication with first fluid path 1103, and the drug is ready to be delivered. Referring also to FIGS. 11C and 11D, the user then inhales through mouthpiece 1140, fluid enters first chamber 1101 through inlet channels 1105' to entrain the drug, the drug then exits the first chamber through outlet channels 1106', and the drug is delivered, for example, as described above for device 400 and device 900.

Figure 11E:
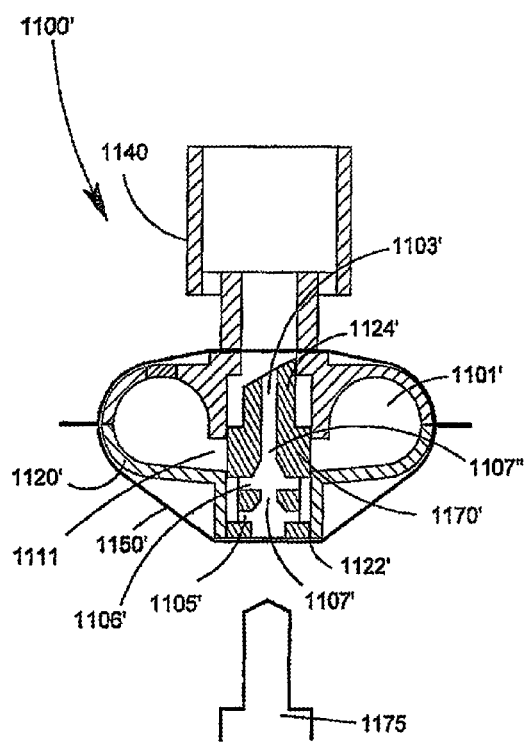
FIG. 11E is a cross-sectional schematic diagram of an embodiment of a drug delivery device in a closed position.
Figure 11F:
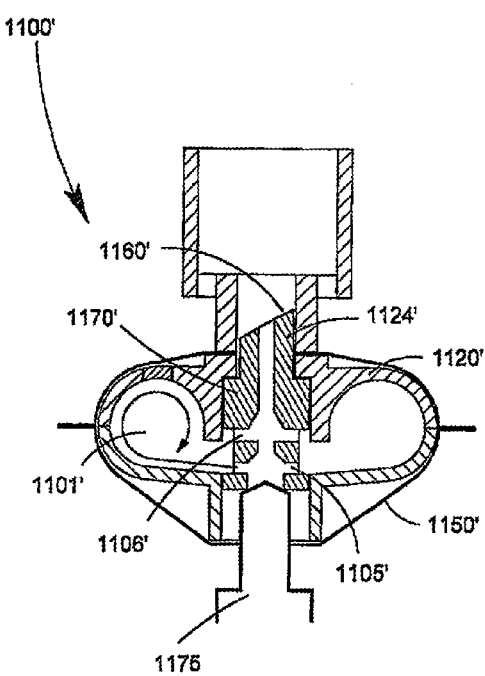
FIG. 11F is a cross-sectional schematic diagram of the device shown in FIG. 11E in an opened position.

In other embodiments, the inlet and outlet channels of device 1100 are features of a first member. FIG. 11E shows a drug delivery device 1100' in a closed position, and FIG. 11F shows the device in an opened position. As shown, device 1100' includes a housing 1120', a first member 1124' received by the housing, a second chamber 1150' that encloses the housing and the first member, a mouthpiece 1140, and a plunger 1175 having a cutting tip. In some embodiments, plunger 1175 includes an open-ended passageway to provide fluid communication into housing 1120'. Device 1100' has a low profile and may be particularly useful, for example, for multi-dose drug delivery systems.

Housing 1120' is similar to housing 1120, but housing 1120' does not include inlet or outlet channels. Housing 1120' includes a toroidal first chamber 1101', and a passageway 1122' that receives first member 1124'. Rather than having one continuous toroidal first chamber 1101', as shown, in other embodiments, device 1100' includes multiple discontinuous first chambers arranged around a first member 1124' that are capable of fluidly communicating with a first fluid path 1103 via multiple sets of unitarily formed inlet and outlet channels.

First member 1124' configured to be received in passageway 1122' of housing 1120'. First member 1124' has a solid portion 1170' capable of tightly sealing opening 1111 of first chamber 1101', while allowing first member 1124' and housing 1120' to translate relative to each other during use. First member 1124 includes first fluid path 1103', inlet channels 1105', and outlet channels 1106'. Inlet and outlet channels 1105', 1106' are capable of aligning with opening 1111 to provide fluid communication between first chamber 1101' and first fluid path 1103'. First fluid path 1103' has two restrictions 1107', 1107" from upstream width/diameter to a smaller downstream width/diameter along the length of the first fluid path. At a downstream end, first member 1124' also includes a cutting edge 1160' configured to puncture second chamber 1150'.

Second chamber 1150' may be configured to provide the drug in first chamber 1101' with additional protection and to be punctured by cutting edge 1160' of first member 1124' during use. In some embodiments, second chamber 1150' includes two layers of a moisture impervious material, such as a plastic coated foil. The layers of material may be preformed to create second chamber 1150' when they are attached together.

Device 1100' may be provided in a closed position (FIG. 11E). The drug in first chamber 1101' may be protected (e.g., from moisture and/or air) by solid portion 1170' of first member 1124', which tightly seals opening 1111 and may prevent movement of the drug out of the first chamber. The drug may be also protected by second chamber 1150'.

In use, mouthpiece 1140' engages outlet end of housing 1120', plunger 1175' engages an inlet end of first member 1124', and the mouthpiece and the plunger are moved toward each other in opposing directions. As plunger 1175 moves toward first member 1124' and into second chamber 1150', the plunger punctures the second chamber and translates the first member relative to housing 1120', thereby removing the tight seal blocking opening 1111. Eventually cutting edge 1160' of first member 1124' punctures second chamber 1150', and inlet and outlet channels 1105', 1106' of the first member align with opening 1111 of first chamber 1101'. Plunger 1175 is then withdrawn from housing 1120', or if the plunger includes a passageway, the plunger may be kept in place. Device 1100' is in an opened position (FIG. 11F) in which first chamber 1101 is in fluid communication with first fluid path 1103', and the drug may be ready to be delivered. The user then inhales through mouthpiece 1140 (e.g., in passive embodiments), fluid enters first chamber 1101' through inlet channels 1105' to entrain the drug, the drug then exits the first chamber through outlet channels 1106', and the drug is delivered through first fluid path 1103'.

Figure 12A:
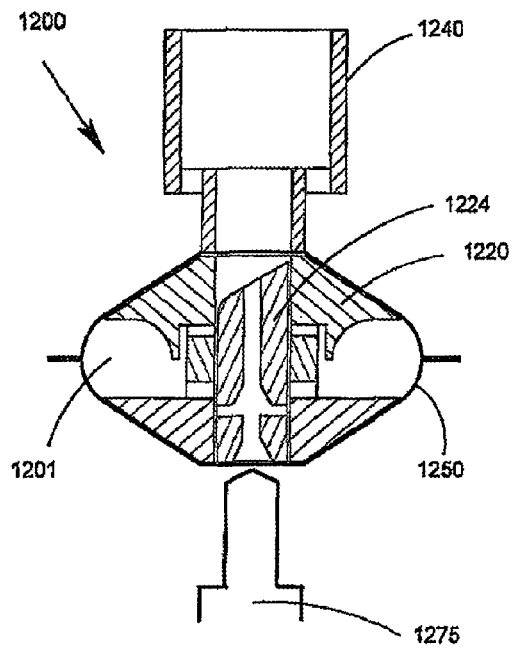
FIG. 12A is a cross-sectional schematic diagram of an embodiment of a drug delivery device in a closed position.

In other embodiments, a second chamber may define a portion of a first chamber, which stores a drug. FIG. 12A shows a device 1200 similar to device 1100 shown in FIG. 11 including a housing 1220, a first member 1224 received in the housing, a mouthpiece 1240, and a plunger 1275. Device 1200 further includes a second chamber 1250 that forms a wall that defines a portion of a first chamber 1201.

Figure 12B:
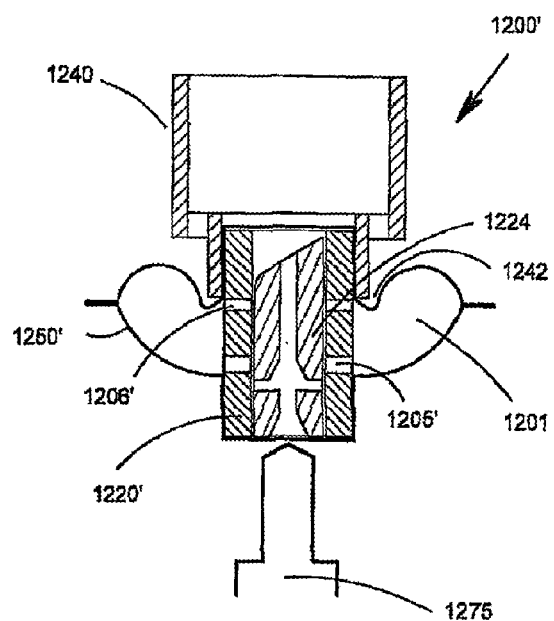
FIG. 12B is a cross-sectional schematic diagram of an embodiment of a drug delivery device in a closed position.

Still in other embodiments, a second chamber may define the entirety of a first chamber, which stores a drug. FIG. 12B shows a device 1200' similar to device 1100 shown in FIG. 11 including a first member 1224, a housing 1220', a mouthpiece 1240, and a plunger 1275. Device 1200' further includes a second chamber 1250' that forms a wall that defines a first chamber 1201'. Second chamber 1250' further includes a recess 1242 that engages with mouthpiece 1240 and that acts as an obstacle to enhance dispersion and metering of the drug.

Housing 1220' includes inlet channels 1205' and outlet channels 1206' that may align with first member 1224 as described above.

Figure 12C:
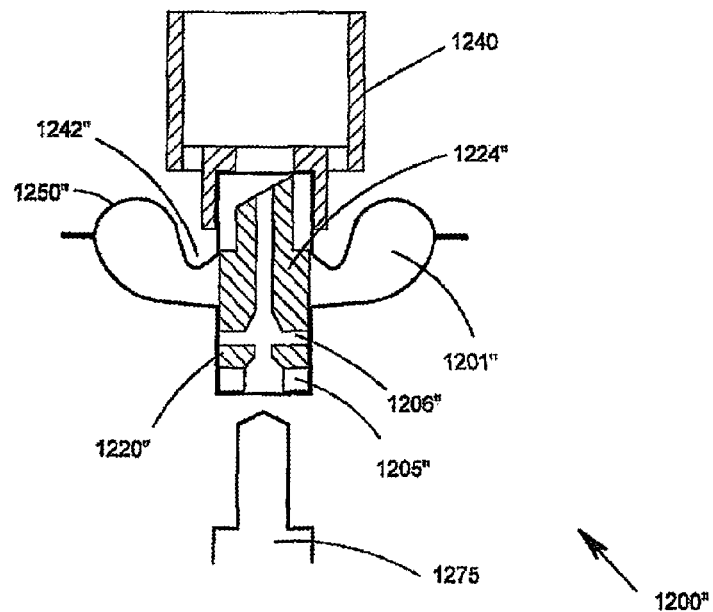
FIG. 12C is a cross-sectional schematic diagram of an embodiment of a drug delivery device in a closed position.

Referring now to FIG. 12C, a device 1200" is shown having a first member 1224" located in a second chamber 1250" with no housing between the first member and the second chamber. Device 1200" further includes a mouthpiece 1240 and a plunger 1275. As shown, first member 1124" includes inlet channels 1205" and outlet channels 1206" that are blocked by second chamber 1250" prior to use. Second chamber 1250" forms a wall that defines a first chamber 1201". Second chamber 1250" further includes a recess 1242" that engages with mouthpiece 1240 and that acts as an obstacle to enhance dispersion and metering of the drug in first chamber 1201". First chamber 1201" is blocked prior to use by a solid portion of first member 1224".

During use, plunger 1275 pushes first member 1224" to puncture second chamber 1250", to remove the seal on first chamber 1201", and to align inlet and outlet channels 1205", 1206" with the first chamber. The drug may be delivered from first chamber 1201" through mouthpiece 1240 as described herein.

Figure 12D:
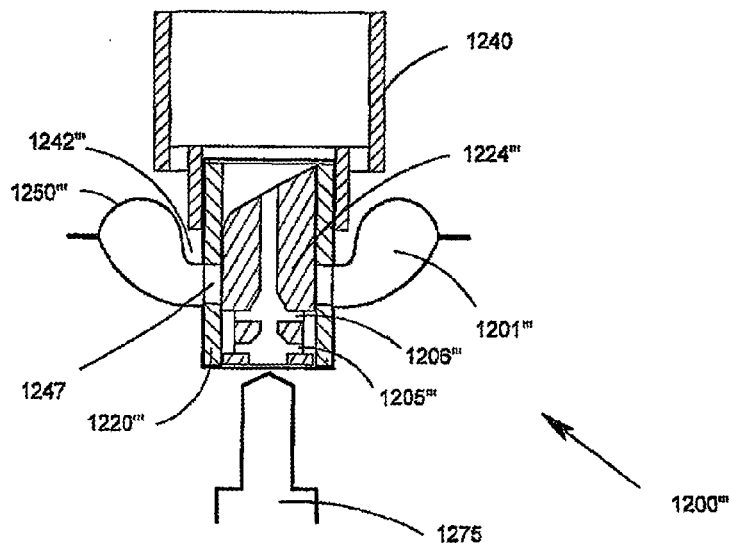
FIG. 12D is a cross-sectional schematic diagram of an embodiment of a drug delivery device in a closed position.

FIG. 12D shows a device 1200''' having a housing 1220''', a first member 1224''' slidably located in the housing, and a second chamber 1250''' enclosing the housing and the first member. Device 1200''' further includes a mouthpiece 1240 and a plunger 1275. As shown, housing 1220''' includes an opening 1247 that is in fluid communication with a first chamber 1201''' but blocked by a solid portion of first member 1224''' prior to use. First member 1224''' includes inlet channels 1205''' and outlet channels 1206''' that are blocked by housing 1220''' prior to use. Second chamber 1250''' forms a wall that defines first chamber 1201'''. Second chamber 1250''' further includes a recess 1242''' that engages with mouthpiece 1240 and that acts as an obstacle to enhance dispersion and metering of the drug in first chamber 1201'''. First chamber 1201''' may be blocked prior to use by a solid portion of first member 1224".

During use, plunger 1275 pushes first member 1224''' to puncture second chamber 1250''', to remove the seal on opening 1247, and to align inlet and outlet channels 1205''', 1206''' with the opening and the first chamber. The drug may be delivered from first chamber 1201''' through mouthpiece 1240 as described herein.

Figure 12E:
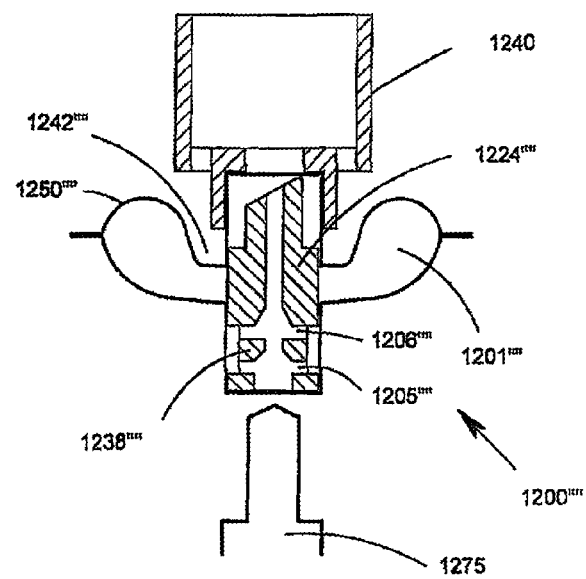
FIG. 12E is a cross-sectional schematic diagram of an embodiment of a drug delivery device in a closed position.
Figure 12F:
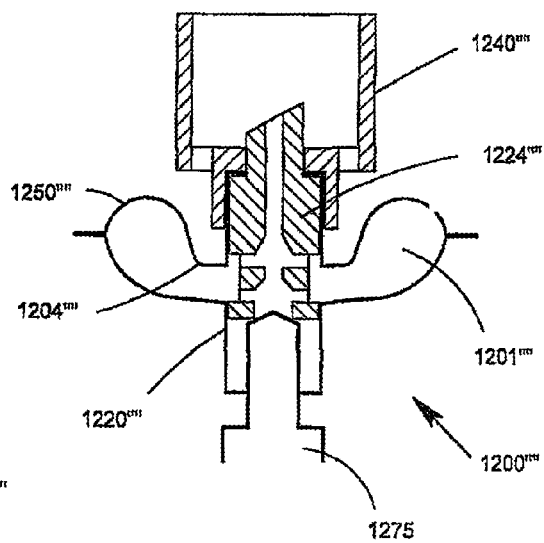
FIG. 12F is a cross-sectional schematic diagram of the device shown in FIG. 12E in an opened position.

FIG. 12E shows a device 1200"" in an closed position, and FIG. 12F shows the device in an opened position. Device 1200"" includes a housing 1220"", a first member 1224"" slidably located in the housing, and a second chamber 1250"" enclosing the housing and the first member. Device 1200"" further includes a mouthpiece 1240 and a plunger 1275. As shown, first member 1224"" includes inlet channels 1205"", outlet channels 1206"", and a volume 1238''' that are blocked by housing 1220''' prior to use. Second chamber 1250"" forms a wall that defines first chamber 1201"". Second chamber 1250"" further includes a recess 1242''' that engages with mouthpiece 1240 and that acts as an obstacle to enhance dispersion and metering of the drug in first chamber 1201'''. First chamber 1201"" may be blocked prior to use by a solid portion of first member 1224".

During use, plunger 1275 pushes first member 1224"" to puncture second chamber 1250"". Moving first member 1224"" also removes the seal to first chamber 1201"" and eventually aligns inlet and outlet channels 1205"", 1206" with first chamber (FIG. 12F). Plunger 1275 may be removed or kept in place if it includes a fluid passageway. The drug may be delivered from first chamber 1201"" through mouthpiece 1240 as described herein, with recess 1242"" (acting as an obstacle 1204"") and volume 1238"" providing drug metering and dispersion.

In other embodiments, a first chamber may be in fluid communication with an outlet air path when a drug delivery device is in its closed position. FIG. 13A shows a drug delivery device 1300 in a closed position, and FIG. 13B shows the device in an opened position.

Device 1300 includes a housing 1320, a first member 1324 secured in the housing, a mouthpiece 1340 configured to engage with the first member, and a plunger 1375 configured to move the first member. As shown, housing 1320 may be formed of two layers of a moisture impervious material, such as a plastic coated foil. The layers, which may be pre-formed to create housing 1320 when attached together, also form a first chamber 1301 that stores a drug. As shown, first chamber 1301 may assume a generally toroidal shape (FIG. 13B) and extends around first member 1324, but in other embodiments, the first chamber assumes other cross-sectional shapes and volumes. As shown, housing 1320 and first chamber 1301 are connected to mouthpiece 1340, but in other embodiments, the mouthpiece may be unconnected to the housing.

First member 1324 may be configured to provide fluid communication between mouthpiece 1340 and first chamber 1301 and to puncture housing 1320. First member 1324 includes a first fluid path 1303 in fluid communication with multiple outlet channels 1306, and a second fluid path 1303' in fluid communication with multiple inlet channels 1305. Inlet and outlet channels 1305, 1306 are in fluid communication with first chamber 1301. First member 1324 also includes a cutting edge 1360 configured to puncture housing 1320 and to engage with mouthpiece 1340.

Mouthpiece 1340 includes an outlet ring 1352 and a unitarily formed fluid bypasses 1341. Outlet ring 1352 may be configured to engage with and to be in fluid communication with first fluid path 1303 during use. Bypasses 1341 allow fluid to flow around the drug flowing through mouthpiece 1340. Varying the cross sectional area of bypasses 1341 may change the flow characteristics through mouthpiece 1340 and first chamber 1324.

Plunger 1375 may be configured to puncture housing 1320, to advance first member 1324, and to provide fluid communication into first chamber 1301 from an exterior of the housing. As shown, plunger 1375 includes a cutting edge 1376 and a fluid channel 1378 configured to engage with second fluid path 1303'. Fluid channel 1378 may be in fluid communication with an exterior environment.

Device 1300 may be provided in a closed position (FIG. 13A). A drug may be stored and sealed in first chamber 1301 of housing 1320. Mouthpiece 1340 may be attached to or spaced from housing 1320.

To use device 1300, plunger 1375 may be advanced toward first member 1324 to form two punctures. Cutting edge 1376 of plunger 1375 punctures housing 1320 to place fluid channel 1378 in fluid communication with first chamber 1301 via second fluid path 1303' and inlet channels 1305. Simultaneously or sequentially, cutting edge 1360 of first member 1324 punctures housing 1320 to place mouthpiece 1340 in fluid communication with first chamber 1301 via first fluid path 1303 and outlet channels 1306. Eventually, first member 1324 engages with mouthpiece 1340, and device 1300 is in an opened position (FIG. 13B). Housing 1320 is deformed, and first chamber 1301 assumes a substantially toroidal shape. Device 1300 may be ready for inhalation.

The user then inhales through mouthpiece 1340 (e.g., in passive embodiments), which causes the drug to be delivered from first chamber 1301 through the mouthpiece. More specifically, still referring to FIG. 13B, fluid moves through fluid channel 1378 of plunger 1375, through inlet channels 1305 and into first chamber 1301. Fluid flow then entrains the drug in first chamber 1301, which, similar to other first chambers described herein, may be designed to fluidize the drug and to prevent it from leaving device 1300 as large clump(s). The drug moves in a re-circulating path within first chamber 1301 and eventually exits through outlet channels 1306, through first fluid path 1303, and through mouthpiece 1340 to the user.

In other embodiments, referring to FIG. 13C, device 1300 includes a first restriction 1307 between inlet channels 1305 and outlet channels 1306.

FIGS. 14A and 14B show another device 1400 in which the material that makes up a second chamber forms a substantial portion (e.g., all) of a housing and/or a first chamber. FIG. 14A shows a drug delivery device 1400 in a closed position, and FIG. 14B shows the device in an opened position.

Device 1400 includes a housing 1420, a first member 1424 secured in the housing, a mouthpiece 1440 configured to engage with the first member, and a plunger 1475 configured to move the first member. As shown, housing 1420 may be formed of two layers of a moisture impervious material, such as a plastic coated foil. The layers, which may be pre-formed to create housing 1420 when attached together, also form a first chamber 1401 that stores a drug. As shown, first chamber 1401 may assume a generally toroidal shape (FIG. 14B) and extends around first member 1424, but in other embodiments, the first chamber assumes other cross-sectional shapes and volumes. As shown, housing 1420 and first chamber 1401 are connected to mouthpiece 1440, but in other embodiments, they are unconnected.

First member 1424 may be configured to provide fluid communication between mouthpiece 1440 and first chamber 1401 and to puncture housing 1420. First member 1424 includes a first fluid path 1403 in fluid communication with multiple outlet channels 1406, and multiple inlet channels 1405. Inlet and outlet channels 1405, 1406 are in fluid communication with first chamber 1401. First member 1424 also includes a cutting edge 1460 configured to puncture housing 1420 and to engage with mouthpiece 1440.

Mouthpiece 1440 includes a fluid channel 1480 and a unitarily formed fluid bypasses 1441. Fluid channel 1480 may be configured to engage with and to be in fluid communication with first fluid path 1403 during use. Bypasses 1441 allow fluid to flow around the drug flowing through mouthpiece 1440. Varying the cross sectional area of bypasses 1441 may change the flow characteristics through mouthpiece 1440 and first member 1424.

As shown, plunger 1475 has a blunt tip, but in other embodiments, the plunger has a sharp tip to puncture housing 1420. During use, the sharp-tipped plunger may puncture housing 1420 and be subsequently withdrawn. The deformation of housing 1420 caused by the puncture may act as a restriction along fluid flow path 1403 (see, e.g., FIGS. 15A and 15B below).

Device 1400 may be provided in a closed position (FIG. 14A). A drug may be stored and sealed in first chamber 1401 of housing 1420. Mouthpiece 1440 may be attached to or separate from housing 1420.

To use device 1400, plunger 1475 may be advanced toward first member 1424 to puncture housing 1420 with cutting edge 1460. In other embodiments, the user uses a finger to advance first member 1424 to puncture housing 1420. Eventually, first member 1424 contacts, engages with and seals fluid channel 1480, and device 1400 may be in an opened position. Mouthpiece 1440 may be in fluid communication with first chamber 1401 via fluid channel 1480, first fluid path 1403 and outlet channels 1406. Mouthpiece 1440 is also in fluid communication with first chamber 1401 via inlet channels 1405, which extend out of housing 1420. Housing 1420 may be deformed, and first chamber 1401 assumes a substantially toroidal shape. Device 1400 may be ready for inhalation.

The user then inhales through mouthpiece 1440 (e.g., in embodiments configured for passive use), which causes the drug to be delivered from first chamber 1401 through the mouthpiece. More specifically, referring also to FIG. 14C, fluid moves through inlet channels 1405 and into first chamber 1401. Fluid flow then entrains the drug in first chamber 1401, which, similar to other first chambers described herein, may be designed to fluidize the drug and to prevent it from leaving device 1400 as large clump(s). The drug moves in a re-circulating path within first chamber 1401 and eventually exits through outlet channels 1406 (FIG. 14D), through first fluid path 1403, through fluid channel 1480, and through mouthpiece 1440 to the user.

In other embodiments, fluid flow into a first chamber containing a drug may be created by puncturing the first chamber. FIG. 15A shows a drug delivery device 1500 in a closed position, and FIG. 15B shows the device in an opened position.

Device 1500 includes a housing 1520, a first member 1524 secured in the housing, a mouthpiece 1540 configured to engage with the first member, and a plunger 1575 having an optional sharp tip 1543 and configured to move the first member. As shown, housing 1520 may be formed of two layers of a moisture impervious material, such as a plastic coated foil. The layers, which may be pre-formed to create housing 1520 when attached together, also form a first chamber 1501 that stores a drug. As shown, first chamber 1501 may assume a generally toroidal shape (FIG. 15B) and extends around first member 1524, but in other embodiments, the first chamber assumes other cross-sectional shapes.

First member 1524 may be configured to provide fluid communication between mouthpiece 1540 and first chamber 1501 and to puncture housing 1520. First member 1524 includes a first fluid path 1503 in fluid communication with multiple outlet channels 1506, which are in fluid communication with first chamber 1501. First member 1524 also includes a cutting edge 1560 configured to puncture housing 1520 and to engage with mouthpiece 1540.

Mouthpiece 1540 includes a fluid channel 1580, unitarily formed fluid bypasses 1541, and one or more (as shown, two) puncturing elements 1582. Fluid channel 1580 may be configured to engage with and to be in fluid communication with first fluid path 1503 during use. Bypasses 1541 allow fluid to flow around the drug flowing through mouthpiece 1540. Varying the cross sectional area of bypasses 1541 may change the flow characteristics through mouthpiece 1540 and first member 1524. Referring also to FIG. 15E, puncturing elements 1582 are capable of puncturing housing 1520 to provide fluid flow into the housing and, more specifically, into first chamber 1501 to deliver the drug. Each puncturing elements 1582 has a generally triangular cross-section that may be defined by two walls that meet to form a curved and helical cutting edge 1574, and meet at a first end and diverge to a second end wider than the first end. The walls define a channel 1572 that extends the length of puncturing element 1585 and opens at the second wider end. Channel 1572 allows air to flow from an exterior of housing 1520 into first chamber 1501 during use. The top of puncturing elements 1582 (as shown in FIG. 15A) may be opened. The shape of puncturing elements 1582 makes openings on housing 1520 that have flared, curved shapes (FIG. 15C). More specifically, in slicing through housing 1520, puncturing elements 1582 form two flaps 1577 attached to the housing. Each flap 1577 has a width (W) that may be approximately half the width of puncturing element 1582. Each flap 1577 also has longitudinal curved edge 1555 that extends helically to the surface of housing 1520. It is believed that the aerodynamic helical shapes of puncturing elements 1582 and flaps 1577 help to direct and to circulate fluid flow in housing 1520 to enhance drug dispersion and metering. The aerodynamic helical shapes of puncturing elements 1582 and flaps 1577, particularly their orientation relative to air flow in housing 1520, also reduce the amount of drug that may get stuck on the puncturing elements and/or the flaps. In other embodiments, puncturing elements 1582 are separate from mouthpiece 1540, located on the plunger side, and/or mounted on the plunger Device 1500 may be provided in a closed position (FIG. 15A). A drug may be stored and sealed in first chamber 1501 of housing 1520. Puncturing elements 1582 are spaced from housing 1520.

To use device 1500, plunger 1575 and mouthpiece 1540 are advanced toward each other. As plunger 1575 may be advanced toward first member 1524, housing 1520 may be punctured with sharp tip 1543 and cutting edge 1560. In other embodiments, the user uses a finger to puncture housing 1520 with first member 1524. Sharp tip 1543 forms a first restriction 1507 (FIG. 15B) in housing 1520 between the exterior of the housing and outlet channels 1506. Simultaneously or sequentially, puncturing elements 1582 of mouthpiece 1540 puncture housing 1520 (FIG. 15C). Eventually, first member 1524 contacts, engages with and seals fluid channel 1580, and device 1500 may be in an opened position (FIG. 15B). Mouthpiece 1540 may be in fluid communication with first chamber 1501 via fluid channel 1580, first fluid path 1503 and outlet channels 1506. First chamber 1501 is also in fluid communication to an exterior of housing 1520 via channel 1572 of puncturing elements 1582. Housing 1520 may be deformed, and first chamber 1501 assumes a substantially toroidal shape. Device 1500 may be ready for inhalation.

The user then inhales through mouthpiece 1540 (e.g., in embodiments configured for passive use), which causes the drug to be delivered from first chamber 1501 through the mouthpiece. More specifically, referring to FIGS. 15B and 15C, fluid may be drawn through channel 1572 and into first chamber 1501. Fluid flow then entrains the drug in first chamber 1501, which, similar to other first chambers described herein, may be designed to fluidize the drug and to prevent it from leaving device 1500 as large clump(s). The drug moves in a re-circulating path within first chamber 1501 and eventually exits through outlet channels 1506 (FIG. 15D), through first fluid path 1503, through fluid channel 1580, and through mouthpiece 1540 to the user.

In some embodiments, housing 1520 may be punctured at other locations other than the top of the housing, as viewed in FIG. 15A. For example, housing 1520 may be punctured on the side(s) and/or on the bottom, as viewed in FIG. 15A. Device 1500 may be free of puncturing elements 1582, and housing 1520 may be punctured by any puncturing tool that may be subsequently withdrawn.

In other embodiments, a plunger provides all fluid communication to a first chamber containing a drug as well as the opening mechanisms to the first chamber. FIG. 16A shows a drug delivery device 1600 in a closed position, and FIG. 16B shows the device in an opened position.

Device 1600 includes a housing 1620, a mouthpiece 1640 configured to engage with the housing, and a plunger 1675 configured to puncture the housing and to provide fluid communication into and out of the housing. As shown, housing 1620 may be formed of two layers of a moisture impervious material, such as a plastic coated foil. The layers, which may be pre-formed to create housing 1620 when attached together, also form a first chamber 1601 that stores a drug. As shown, first chamber 1601 has a generally toroidal shape (FIG. 16B), but in other embodiments, the first chamber assumes other cross-sectional shapes. Housing 1620 also includes perforated supports 1602 that help provide the housing with its shape and define a passageway 1622 to receive plunger 1675. As shown, housing 1620 and first chamber 1601 are connected to mouthpiece 1640, but in other embodiments, the mouthpiece may be unconnected to the housing.

Plunger 1675 is configured to puncture housing 1620 and to provide fluid communication into and out of the housing, in particular, first chamber 1601. Similar to some previously described first members (e.g., first member 824 (FIG. 8A)), plunger 1675 includes a first fluid path 1603 in fluid communication with multiple inlet channels 1605 and multiple outlet channels 1606. First fluid path 1603 is in fluid communication with an exterior environment. Plunger 1675 further includes a cutting edge 1685 configured to puncture housing 1620 and to engage with mouthpiece 1640, and a stop 1689 configured to restrict movement of the plunger relative to the housing 1620 during use.

Mouthpiece 1640 includes a fluid channel 1680 and a unitarily formed fluid bypass 1641. Fluid channel 1680 is configured to engage with and to be in fluid communication with first fluid path 1603 during use. Bypass 1641 allows fluid to flow around the drug flowing through mouthpiece 1640 and may have varying cross-sectional shapes as described herein.

Device 1600 may be provided in a closed position (FIG. 16A). A drug is stored and sealed in first chamber 1601 of housing 1620. Mouthpiece 1640 may be attached to or separate from housing 1620.

To use device 1600, plunger 1675 is advanced toward housing 1620, in particular, through passageway 1622 defined by perforated supports 1602. As plunger 1475 is advanced, cutting edge 1685 punctures housing 1620 at two different portions. Eventually, plunger 1675 engages with mouthpiece 1640, and device 1600 may be in an opened position (FIG. 16B). First chamber 1601 may be in fluid communication with an exterior environment via inlet channels 1605 and first fluid path 1603. First chamber 1601 may be also in fluid communication with mouthpiece via outlet channels 1606 and first fluid path 1603. Plunger 1675 may be prevented from advancing any further by stop 1689. Device 1600 may be ready for inhalation.

The user then inhales through mouthpiece 1640 (e.g., in embodiments configured for passive use), which causes the drug to be delivered from first chamber 1601 through the mouthpiece. More specifically, still referring to FIG. 16B, fluid may be drawn through first fluid path 1603 of plunger 1675, through inlet channels 1605 and into first chamber 1601 (FIG. 16C). Fluid flow then entrains the drug in first chamber 1601, which, similar to other first chambers described herein, may be designed to fluidize the drug and to prevent it from leaving device 1600 as large clump(s). The drug moves in a re-circulating path within first chamber 1601 and eventually exits through outlet channels 1606, through first fluid path 1603 (FIG. 16D), and through mouthpiece 1640 to the user. Fluid also flows through directly through first flow path 1603 without entering first chamber 1601.

In other embodiments, mouthpiece 1640 and plunger 1675 are connected to form a unitary structure. FIG. 16E shows a device 1600' including housing 1620 as described above, and a mouthpiece 1640' connected an outlet end 1636 of a plunger 1675'. An inlet end 1637 of plunger 1675' may be configured to puncture housing 1620. Otherwise, mouthpiece 1640' and plunger 1675' are the same as mouthpiece 1640 and plunger 1675, respectively.

During use, plunger 1675' may be advanced toward housing 1620 to puncture the housing and to place the interior of mouthpiece 1640' in fluid communication with first chamber 1601 via inlet channels 1605 and outlet channels 1606. The drug in first chamber 1601 may be delivered to the user as described above.

FIGS. 22A, 22B, 22C, and 22D show another device 2200 in which a mouthpiece 2240 and a plunger 2275 are connected to form a unitary structure. Plunger 2275 includes inlet channels 2205, outlet channels 2206, and a first fluid path 2203. An interior of mouthpiece 2240 may be in fluid communication with first fluid path 2203. Housing 2220 may be generally the same as housing 1720 including a first chamber 2201, puncturable material 2287 and stiff material 2286.

During use, plunger 2275 may be advanced toward housing 2220 to puncture the housing at puncturable material 2287 and to place inlet and outlet channels 2205, 2206 in fluid communication with first chamber 2201 (FIG. 22B). The drug in first chamber 2201 may be delivered to the user as described above. Air may be drawn into first chamber 2201 through inlet channels 2205 and circulates with the first chamber. The air entrains the drug and delivers the drug through outlet channels 2206, through first fluid path 2203, and through mouthpiece 2240 to the user.

In other embodiments, referring to FIGS. 22E and 22F, a housing 2220' includes a first chamber 2201' that may be initially sealed by a protrusion 2234 and a space 2248 configured to receive the protrusion. Protrusion 2234 may be used to keep the drug within first chamber 2201'. Housing 2220', like housing 2220 includes puncturable material 2287' and stiff material 2286'. Housing 2220' may be used with mouthpiece 2240 and plunger 2275, for example.

Figure 17:
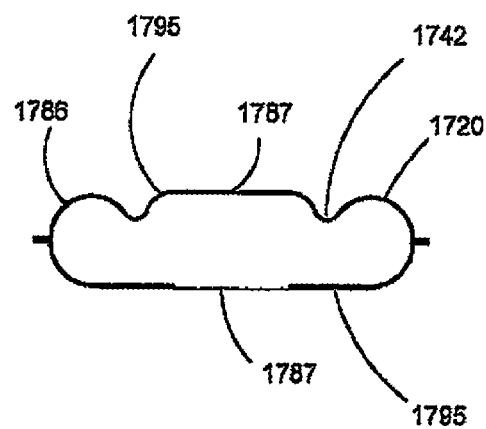
FIG. 17 is a cross-sectional schematic diagram of an embodiment of a housing.

During use, plunger 2275 may be advanced toward housing 2220' to puncture the housing at puncturable material 2287' and to place inlet and outlet channels 2205, 2206 in fluid communication with first chamber 2201' (FIG. 22F). As a result, protrusion 2234 may be moved to space 2248, and the seal between the protrusion and first chamber 2201' is removed. The drug in first chamber 2201' may be delivered to the user as described above. Air may be drawn into first chamber 2201' through inlet channels 2205 and circulates within the first chamber. The air entrains the drug and delivers the drug through outlet channels 2206, through first fluid path 2203, and through mouthpiece 2240 to the user. In other embodiments, housing 1620 may be free of internal supports. FIG. 17 shows a housing 1720 having no internal supports (e.g., perforated supports 1602). Housing 1720 includes (e.g., is formed of) a stiff material 1786 that provides the housing with its shape, and a puncturable material 1787 that forms the punctured areas of the housing. Stiff material 1786 and puncturable material 1787 may be joined together by overlapping the materials and sealing them together, e.g., with an adhesive, at overlapping portions 1795. Puncturable material 1787 may be, for example, the same as stiff material 1786 but thinner for easy puncturing or a foil. Housing 1720 further includes a recess 1742 that may serve as an obstacle for good drug dispersion and metering and that may engage with a mouthpiece, for example. Housing 1720 may be used with mouthpiece 1640 and plunger 1675 described above.

Figure 18A:
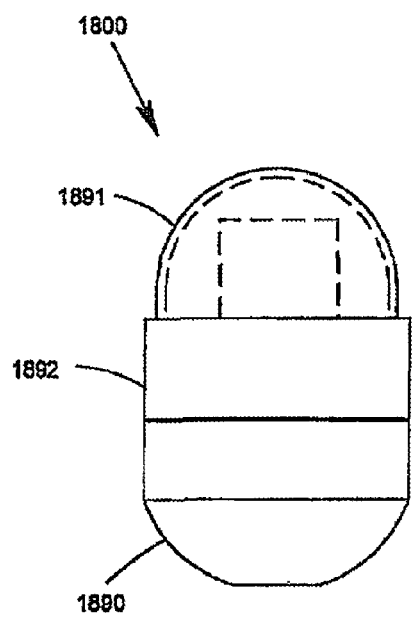
FIG. 18A is a perspective view of an embodiment of a drug delivery device.
Figure 18B:
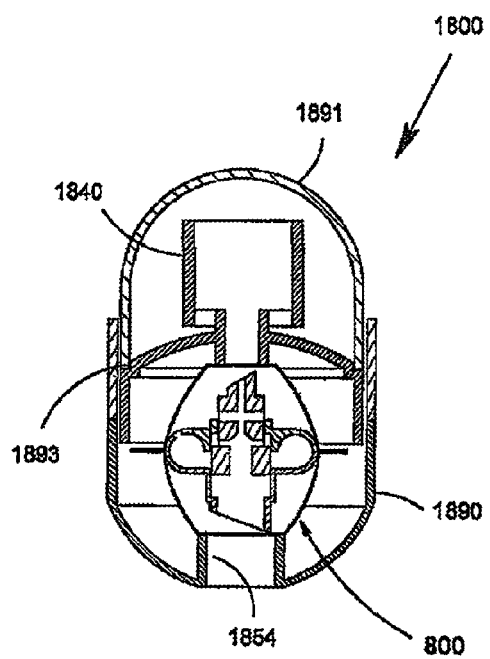
FIG. 18B is a cross-sectional schematic diagram of the device shown in FIG. 18A in a closed position.
Figure 18C:
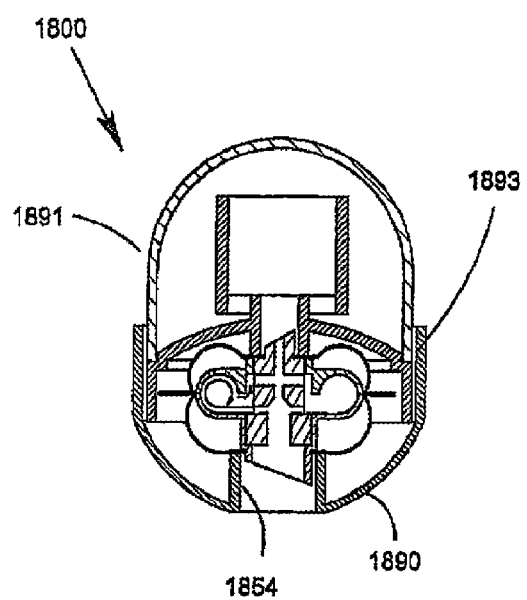
FIG. 18C is a cross-sectional schematic diagram of the device shown in FIG. 18B in an opened position.

The drug delivery devices described herein may be adapted for single-use delivery or multi-use delivery. For example, FIGS. 18A, 18B, 18C and 18D show drug delivery device 800 integrated into a single-use delivery system 1800. System 1800 includes device 800 and a mouthpiece 1840 contained within a back cover 1890 and a mouthpiece cover 1891. As shown, back cover 1890 includes a base 1854, similar to base 854 described above (FIGS. 8A and 8B). Mouthpiece cover 1891 and mouthpiece 1840 slide together and interlock by a plastic snap 1893. Mouthpiece cover 1891 and mouthpiece 1840 slide together with back cover 1890 to form an outer barrier for device 800, and these components are locked together in a closed position by a tamper seal 1892 (FIG. 18A). After tamper seal 1892 is removed during use, mouthpiece 1840 and back cover 1890 may slide toward each other.

Figure 18D:
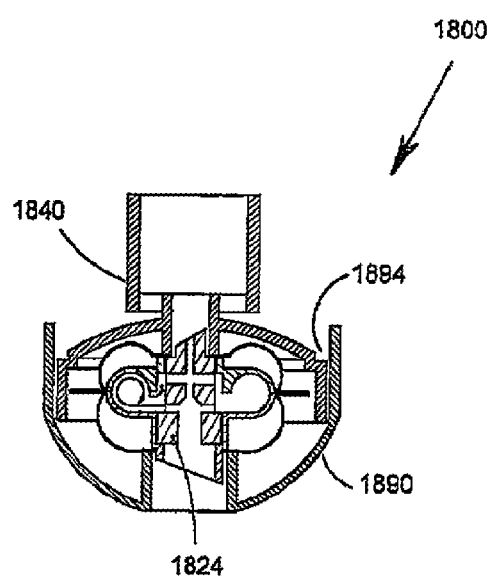
FIG. 18D is a cross-sectional schematic diagram of the device shown in FIG. 18C with a mouthpiece cover removed.

To use system 1800, the tamper seal 1892 may be removed and pressure applied to move mouthpiece cover 1891 and back cover 1890 toward each other. Removing seal 1892 releases the interlock between mouthpiece 1840 and back cover 1890. Moving mouthpiece cover 1891 and back cover 1890 toward each other opens device 800 as described above and shown in FIG. 18C, and deforms snap 1893, allowing the mouthpiece cover to be removed (FIG. 18D). The user then inhales through mouthpiece 1840 (e.g., in embodiments configured for passive activation), and the drug may be delivered as described above for device 800.

In some embodiments, system 1800 includes indicia that provide useful information about the device. For example, system 1800 may be color coded to help identify drug type and/or dose strength. System 1800 may include a dose readiness indicator 1894 that may be a color coded label that becomes visible to the user after mouthpiece cover 1891 may be removed. In addition, first member 1824 inside device 800 may be color coded for visibility. As each device 800 is opened, first member 1824 is exposed and may be made visible to the user by a window in mouthpiece 1840 and/or back cover 1890. Exposed color (e.g., green) may indicate that system 1800 may be ready for inhalation.

As another example, FIGS. 19A, 19B, 19C, and 19D show a system 1900 including a drug delivery device 1999 similar to device 800 but without cutting element 856. System 1900 includes a mouthpiece 1940, drug delivery device 1999, a base cover 1990 configured to receive the mouthpiece and the drug delivery device, and a spring 1998 located inside the base cover. Base cover 1990 includes a plunger 1975 for piercing drug delivery device 1999, and a support 1997 (as shown, a ring) configured to receive the drug delivery device.

Figure 19C:
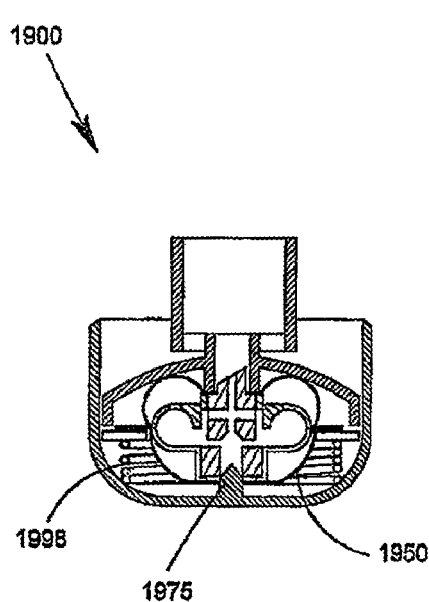
FIG. 19C is a cross-sectional schematic diagram of the device shown in FIG. 19B in a fully compressed position.
Figure 19D:
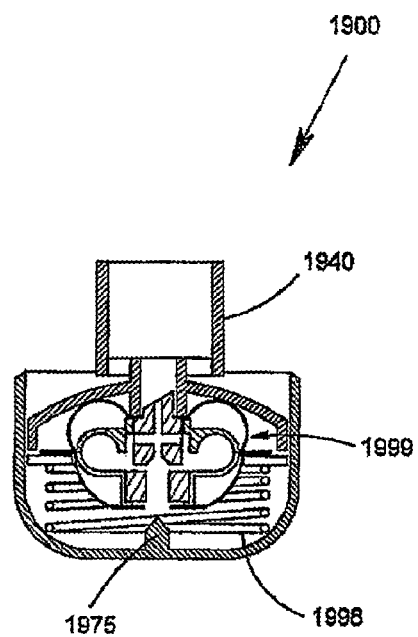
FIG. 19D is a cross-sectional schematic diagram of the device shown in FIG. 19B in an opened position.

To use device 1900, drug delivery device 1999 is placed inside support 1997, and applies pressure to move mouthpiece 1940 and base cover 1990 toward each other. This movement moves drug delivery device 1999 and plunger 1975 toward each other (which punctures the drug delivery device), deforms the drug delivery device, and punctures the drug delivery device when the cutting edge of the drug delivery device passes through second chamber 1950 (FIG. 19C). This movement also compresses spring 1998. Pressure on system 1900 is released and spring 1998 withdraws plunger 1975 from drug delivery device 1999 (FIG. 19D). The user may then inhale through mouthpiece 1940 to administer the drug, (e.g., when the device is configured for passive activation).

Figure 20:
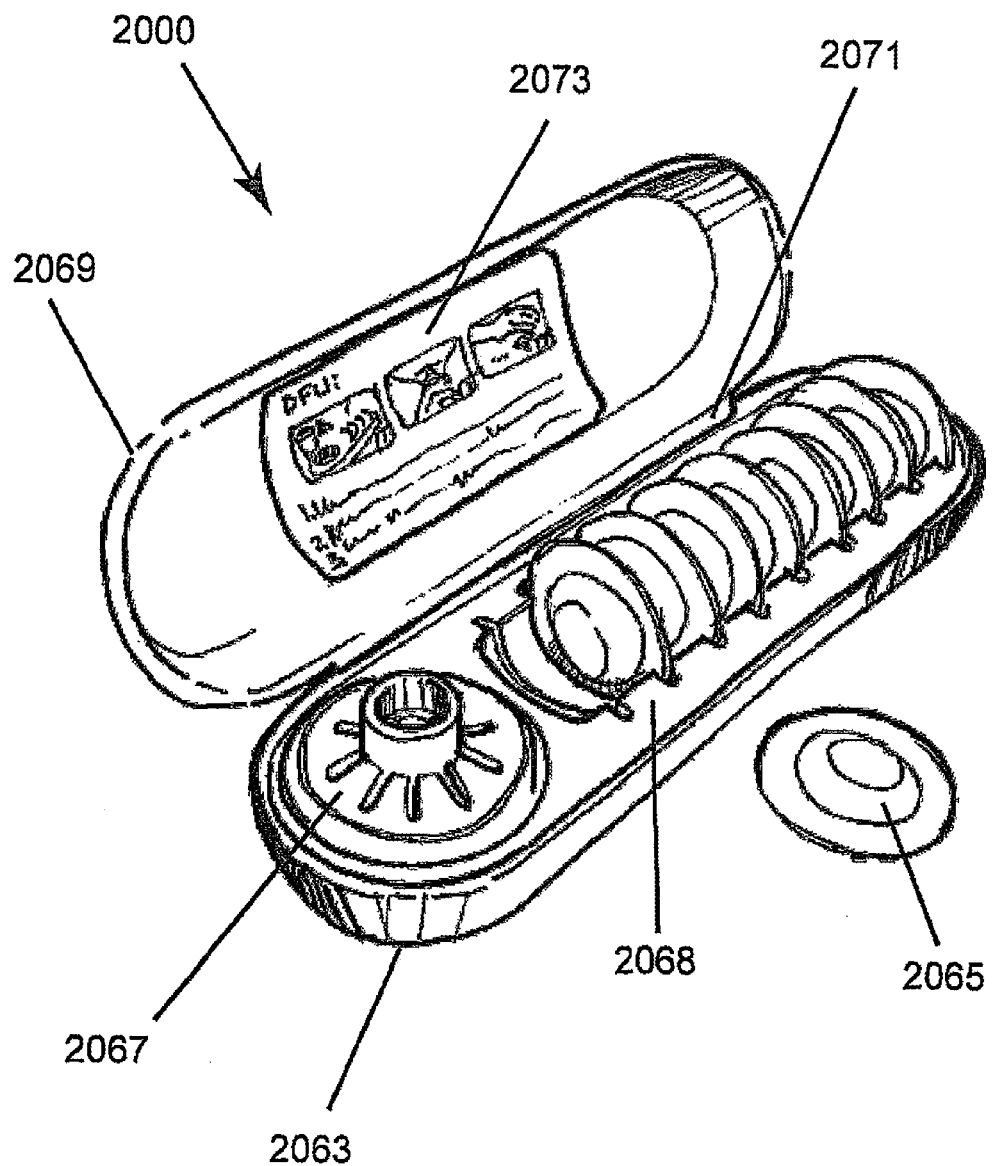
FIG. 20 is a perspective view of an embodiment of a multi-dose drug delivery system.

FIG. 20 illustrates a multi-dose drug delivery system 2000 that integrates the drug delivery devices described herein and serves as an organizational system to simplify the user experience. System 2000 includes a storage case 2063, multiple drug delivery devices 2065 (e.g., device 1300 and device 1999) and an opening mechanism 2067 (e.g., system 1800 and system 1900). As shown, storage case 2063 integrates a dose organizer 2068 that organizes and secures multiple drug delivery devices 2065 to a particular location. Storage case 2063 includes a case cover 2069 that may be attached by a hinge 2071. Case cover 2069 provides a location for directions for use 2073 that are visible to the user when the case cover is open. Drug delivery devices 2065 are designed to be replaceable in opening mechanism 2067, giving users with multi-dose therapies the ability to replace spent doses.

In some embodiments, a drug delivery system (such as systems 1800, 1900 and opening mechanism 2067) includes one or more keying or orientation features that allow the system to operate only when a drug delivery device may be positioned in a predetermined location and orientation. For example, referring to FIG. 19B, while device 1999 is shown as generally unsymmetrical along a horizontal axis, in other embodiments, the device may have a more unsymmetrical shape and/or other keying features such that the device will only fit and operate in base cover 1990 if the device is properly oriented. Device 1999 may include, for example, a projection that may be configured to engage with a slot in base cover 1990 or support 1997. As another example, second chamber 1950 may include a very small end at the bottom (as view in FIG. 19B), and support 1997 may include an opening that accepts the small end at the bottom but not a larger end at the top.

While a number of embodiments have been described, the invention is not limited to the arrangements particularly shown and described. For example, and without limitation, a second chamber of a drug delivery device may be used with other drug delivery devices. Structural features described for one or more devices or systems, such as inlet channels of a housing or a first member, outlet channels of a housing or a first member, first chambers, obstacles, first fluid paths, plungers, mouthpieces, second dispersion chambers, and restrictions, may be adapted for and used in other devices and systems.

While the first members, passageways, fluid paths and plungers have primarily been shown as having circular cross sections, these structures may have other cross sections, including but not limited to oval, elliptical, regular or irregular polygons having three, four, five, six, seven, eight or more sides.

In devices (such as devices 200, 300, 400, 500, 600, 700, 800, 900, 1000, 1100 and 1200) in which a first member may be translated in a housing, the devices may include one or more features that prevent the first member from rotating about its longitudinal axis as the first member may be translated, thereby possibly reducing fluid communication between a first chamber and a first fluid path. For example, the first member may have a non-round cross section that fits in a corresponding non-round passageway of the housing. The housing may include a longitudinal groove extending along the surface its passageway, and the first member may include a projection that tracks in the groove.

An active fluid flow source may be used with all of the embodiments described herein.

Figure 7D:
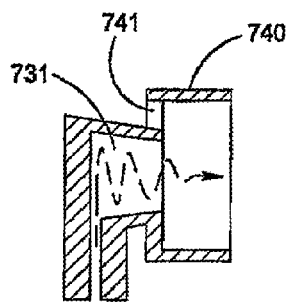
FIG. 7D is a cross-sectional schematic diagram of portion of an embodiment of a drug delivery device.

An access piece, such as a mouthpiece, may be provided with any of the embodiments described herein. The mouthpiece may further include one or more bypasses to control fluid flow into and through the mouthpiece. In some embodiments, the mouthpiece does not include a bypass. Any of the devices described herein may further include a second dispersion chamber upstream of the mouthpiece, as shown in FIGS. 7A and 7D, for example. The second dispersion chamber may include vents or not include vents. It is also to be appreciated that the access piece may include a nasal piece, a combination nasal/mouth piece, or a structure configured to mate with any other orifice of a body, whether natural or otherwise occurring.

In some embodiments, a drug delivery device or system does not include a mouthpiece. A user may inhale the drug by directly putting his/her mouth over a first member capable of providing fluid communication to a first chamber containing the drug.

A drug delivery device or system may include a spacer or a holding chamber between a mouthpiece and the mouth of a user. The spacer or holding chamber may be used to decrease air velocity (e.g., in active systems) upstream of the user's mouth.

While inlet and outlet channels are described as channels, in some embodiments, these inlets and outlets may be openings, without substantial longitudinal lengths.

The plungers described herein may include an air passageway or not include an air passageway. In some embodiments, a plunger not including an air passageway may need to be removed after plunging or puncturing to provide fluid communication into a first chamber.

Within a device, the inlet and outlet channels may be radially straight, radially curved, or a combination of curved and straight, as viewed along the longitudinal axis of the first member. The inlet and outlet channels may overlap each other, partially overlap each other, and/or not overlap each other, as viewed along the longitudinal axis of the first member. The curved inlet and outlet channels may curve in the same direction (e.g., clockwise-clockwise), in different directions (e.g., clockwise-counterclockwise), or a combination of same and different directions.

Figure 21:
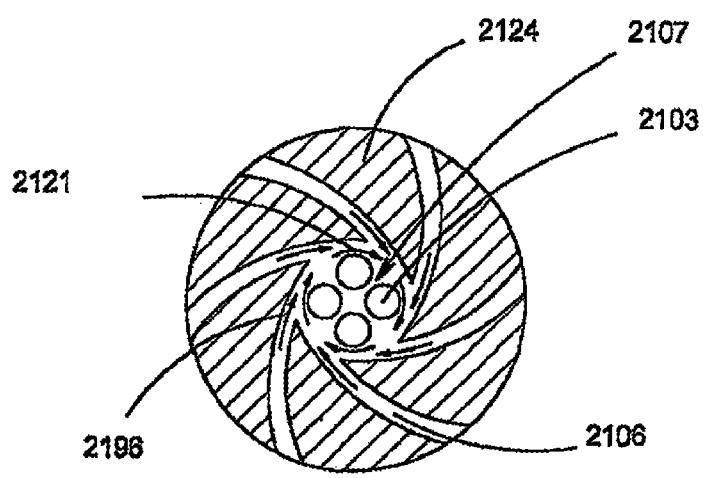
FIG. 21 is a cross-sectional view of a drug delivery system showing an embodiment of a restriction.
Figure 23A:
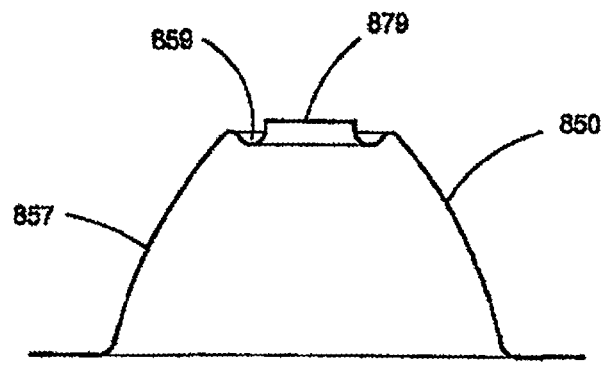
FIG. 23A is cross-sectional illustration of an embodiment of a second chamber in a first position.
Figure 23B:
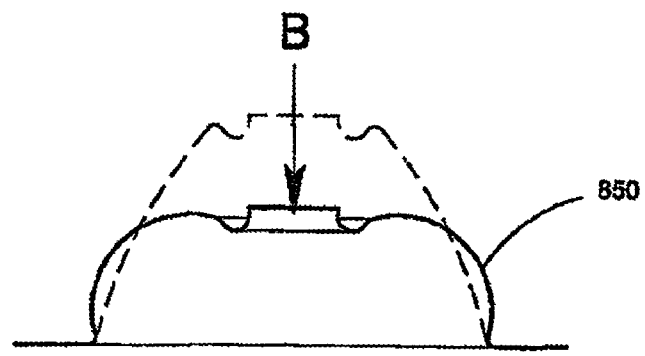
FIG. 23B is cross-sectional illustration of the second chamber of FIG. 23A in a second position.
Figure 23C:
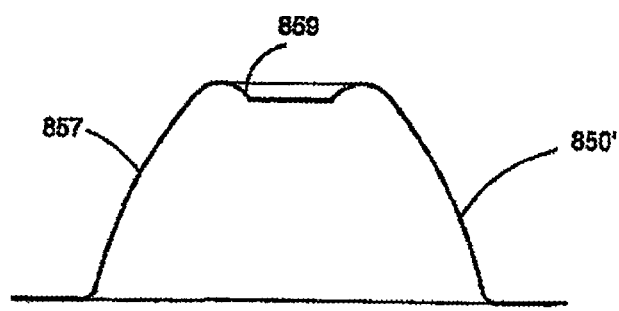
FIG. 23C is cross-sectional illustration of an embodiment of a second chamber in a first position.

While the first restriction is shown herein as being one opening, in other embodiments, the restriction may include multiple openings having smaller widths or diameters than the widths or diameters preceding or succeeding the restriction in a fluid stream. For example, the cross section of a restriction may include two openings side by side, or multiple (e.g., 3, 4, 5, 6 or more) openings arranged in a pattern (e.g., a circular pattern, a non-circular pattern (such as an oval or an ellipse), a plus sign, a star, and a polygon). The openings themselves may have cross sections that are non-circular, such as oval, elliptical, a plus sign, a star-like, and polygonal. The first restriction may be designed to divert or to direct fluid flow into and/or out of the first chamber to create more dispersion (e.g., swirling) along a first fluid path. As an example, FIG. 21 shows a restriction 2107 that includes four openings. As shown, a first member 2124 having curved outlet channels 2106 is introducing fluid flow generally tangential to a cross section of a first fluid path 2103 to provide circular fluid flow 2121 in the first fluid path.

Figure 24A:
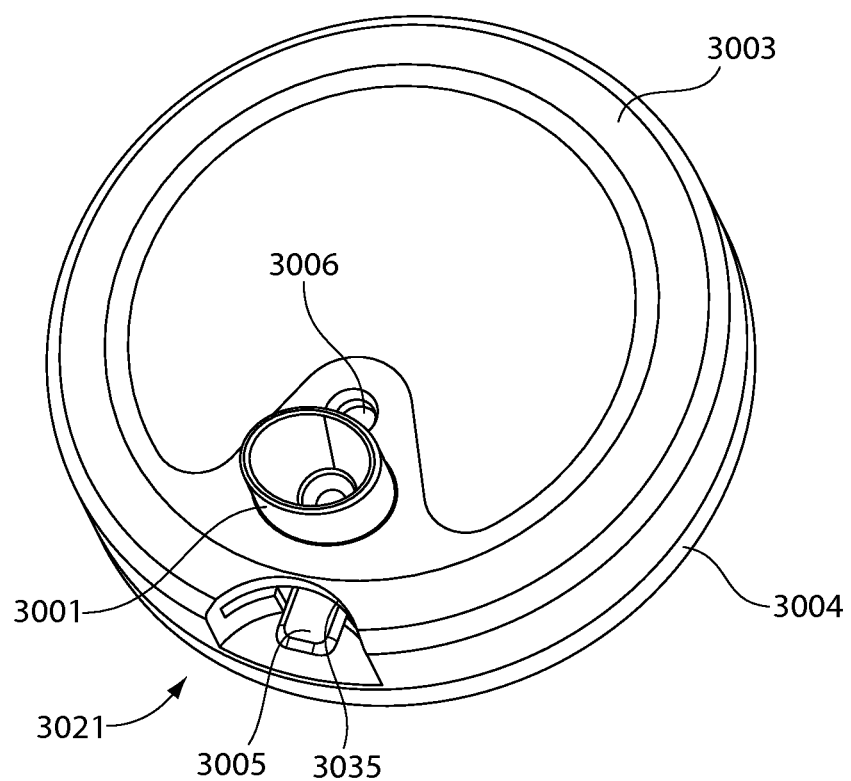
FIG. 24A shows a perspective view of one embodiment of a multi-dose device.
Figure 24B:
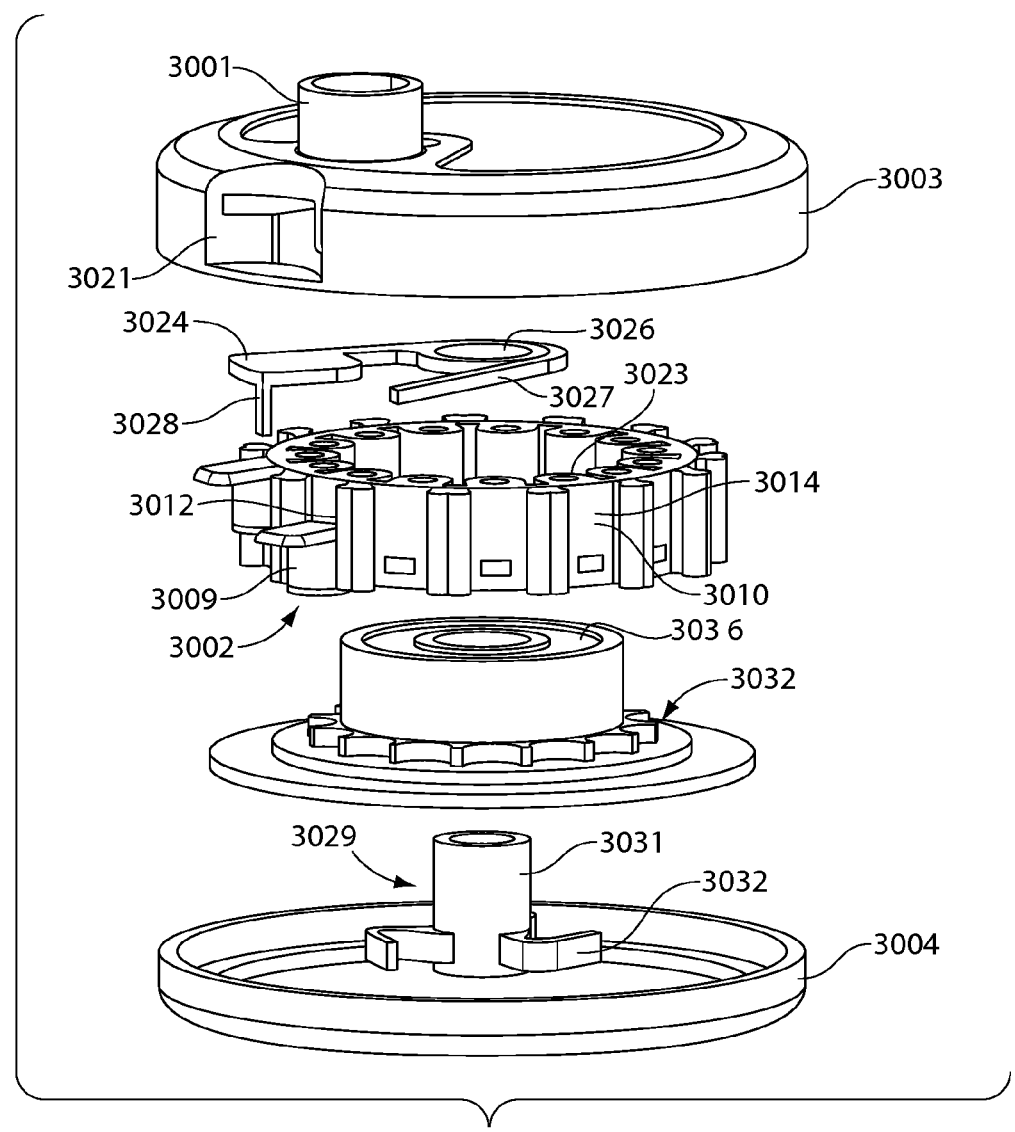
FIG. 24B shows an exploded assembly view of the multi-dose device embodiment of FIG. 24A.
Figure 24C:
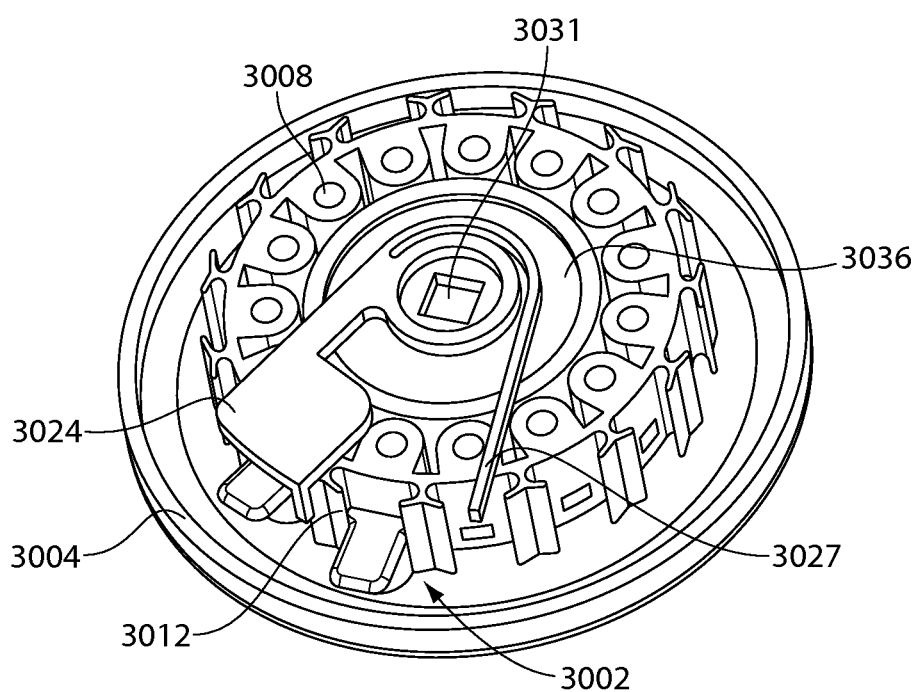
FIG. 24C shows a view of the multi-dose device of FIG. 24A, with the upper housing removed.

One embodiment of a multi-dose device is shown in FIGS. 24A-24c. As shown, the device includes a mouthpiece 3001 through which a subject may inhale to draw medicament from one of a plurality of dispersion engines 3002. The mouthpiece 3001 may be integrated into an upper housing 3003 that may rotate relative to a lower housing 3004 to bring the mouthpiece 3001 into registration, sequentially, with each of the plurality of dispersion engines 3002. A lever portion 3005 of each dose chamber extends through a port of the upper housing 3003 when the corresponding 3002 dispersion engine is in registration with the 3001 mouthpiece. Pressing on the lever portion 3005 may open fluid communication between the mouthpiece 3001 and a registered dispersion engine, thereby readying the dose to be dispensed. The multi-dose device, as shown, also includes an indicator 3006 that displays the number of doses remaining in the device or the number of doses that have been dispensed.

In the embodiment of FIGS. 24A-24C, each dispersion engine includes a dose chamber 3007 and a passageway 3008 that may be placed in fluid communication with the chamber. One embodiment of a dispersion engine that may be incorporated into a multi-dose device is shown in FIGS. 25A-25E, and is discussed herein for use with the multi-dose device shown in FIGS. 24A-24C. It is to be appreciated, however, that numerous other types of dispersion engines may alternately be used, and that the discussion of the dispersion engine of FIGS. 25A-25E in combination with the embodiment of FIGS. 24A-24C is merely exemplary.

Figure 25A:
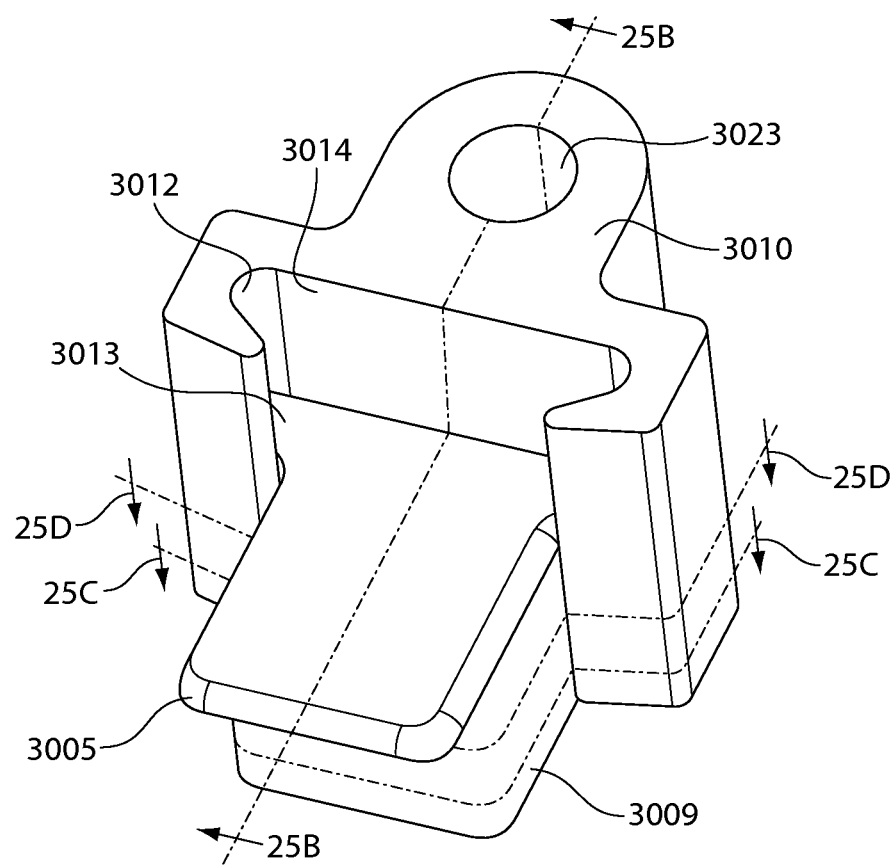
FIG. 25A shows a perspective view of one embodiment of a dispersion engine.

The dispersion engine shown in FIG. 25A has a dose chamber housing 3009 that includes a dose chamber 3007 and a passageway housing 3010 that includes a passageway 3008 and an air entryway 3011. A pair of bearing tracks 3012 is formed in the passageway housing and engages corresponding bearing structures 3013 of the dose chamber housing to hold mating faces 3014 of the dose chamber housing 3009 and the passageway housing 3010 in slidable engagement with one another, as shown in FIG. 25A. A lower portion of the mating face 3014 of the passageway housing includes an opening 3015 in fluid communication with the passageway 3008 and the air entryway 3011. The opening 3015 of the passageway housing may be placed in fluid communication with the corresponding opening in the dose chamber housing to, in turn, place the dose chamber in fluid communication with the passageway and air entryway. In the embodiment of FIG. 25A, this is accomplished by moving the dose chamber housing 3009 downward along the bearing tracks 3012 of the passageway housing. Conversely, moving the dose chamber housing upwardly along the bearing tracks may move the dose chamber out of fluid communication with the passageway. It is to be appreciated that different types of mechanisms and/or motions may also be used to provide fluid communication to a dose chamber. According to some embodiments, this is accomplished by moving a dose chamber housing up relative to stationary passageway housing. In other embodiments, the passageway housing may be moved relative to a stationary dose chamber housing to provide fluid communication to the dose chamber. Moreover, it is to be appreciated that the motion between the dose chamber housing and passageway housing may be rotational, instead of linear, as in the illustrated embodiment.

Figure 25B:
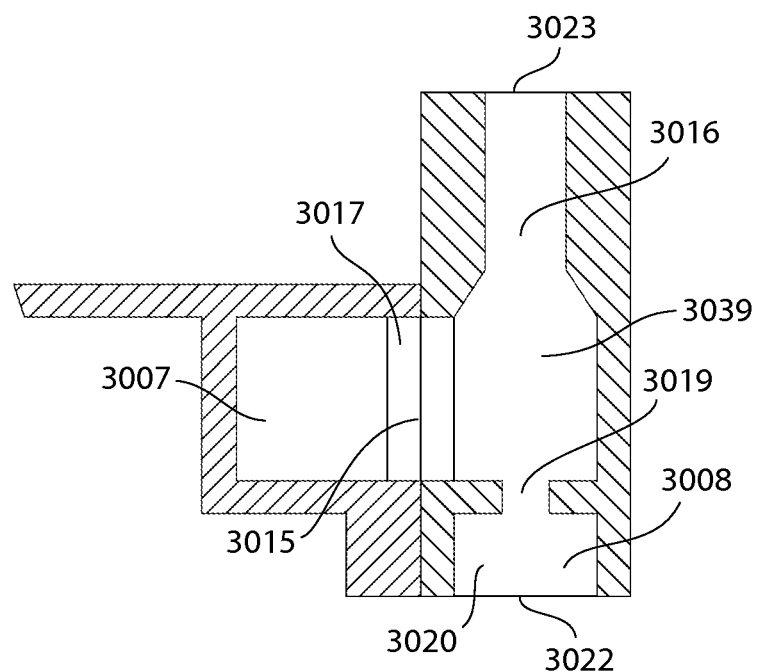
FIG. 25B shows a cross-sectional side view of the dispersion engine shown in FIG. 25A, taken along lines 25B-25B.
Figure 25C:
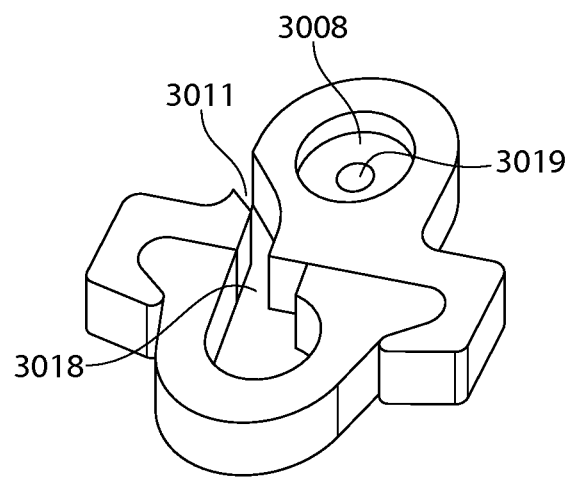
FIG. 25C shows a perspective, cross-sectional view of the dispersion engine shown in FIG. 2a, taken along lines 25C-25C.
Figure 25D:
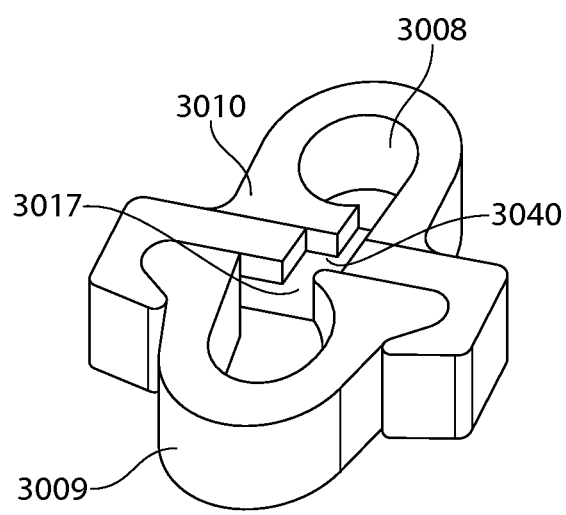
FIG. 25D shows a perspective, cross-sectional view of the dispersion engine shown in FIG. 25A, taken along lines 25D-25D.
Figure 25E:
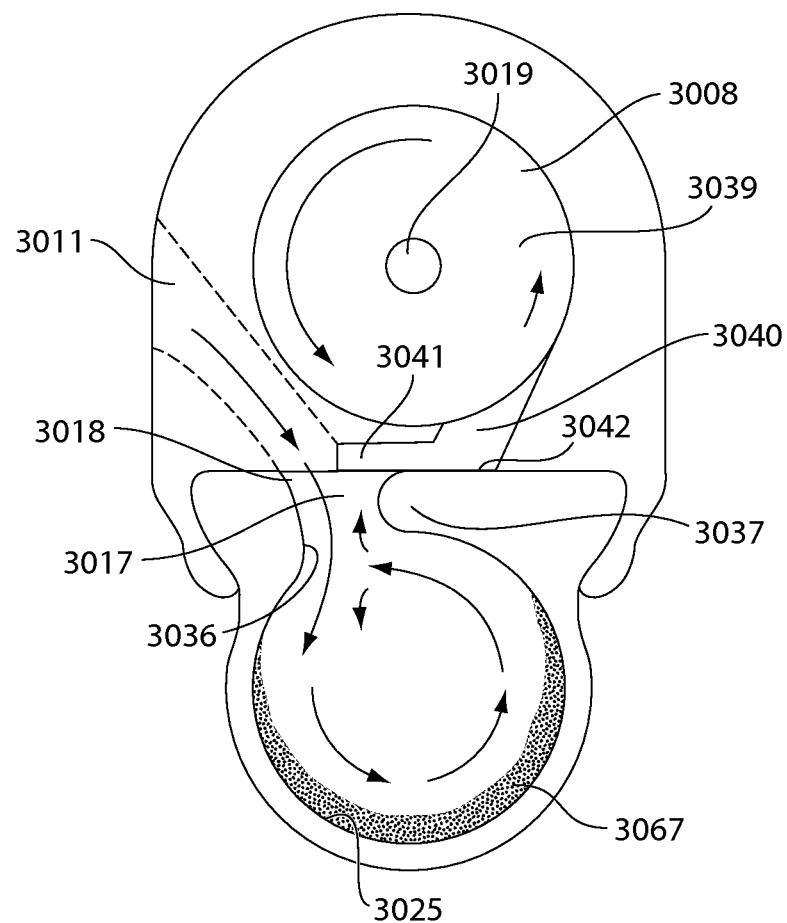
FIG. 25E shows a cross-sectional top view of the dispersion engine shown in FIG. 25A, taken along lines 25D-25D.

FIG. 25B shows a cross-sectional side view of the dispersion engine of FIG. 25A, taken along lines 25B-25B, and depicts a pathway along which air may flow to the upper portion 3016 of the passageway from the dose chamber 3007. As shown, an opening lies between the upper portion 3016 of the passageway and the dose chamber 3007. This opening includes a chamber outlet 3017, through which air may flow from the dose chamber to the passageway. The opening also includes an air inlet 3018 (see FIGS. 25C and 25E) that allows air to enter the dose chamber form an air entryway in the passageway housing. The passageway includes a restriction 3019 upstream of the chamber outlet 3017. The restriction 3019 allows some of the air that enters the upper portion 3016 of the passageway to come from the lower portion 3020 of the passageway and through the restriction 3019, but also promotes air flow to the upper portion 3016 of the passageway from through the dose chamber 3007 and air entryway 3011. FIGS. 25C and 25D, are perspective cross-sectional views taken along lines 25C-25C and 25D-25D, respectively that show additional views of the dose chamber, the passageway, the air entryway, and the interface therebetween. It is to be appreciated that the embodiment of FIG. 25B is but one possible arrangement. By way of example, in other embodiments, the air entryway may receive air from a lower portion of the passageway.

Figure 26A:
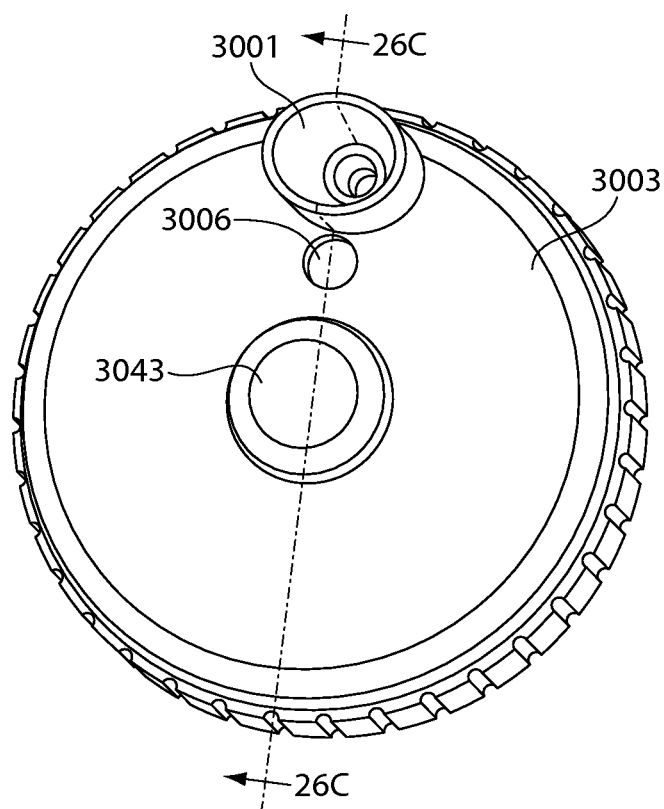
FIG. 26A shows a perspective view of another embodiment of a multi-dose device that includes a central button that may be depressed to ready a dispersion engine to deliver a dose of medicament.
Figure 27:
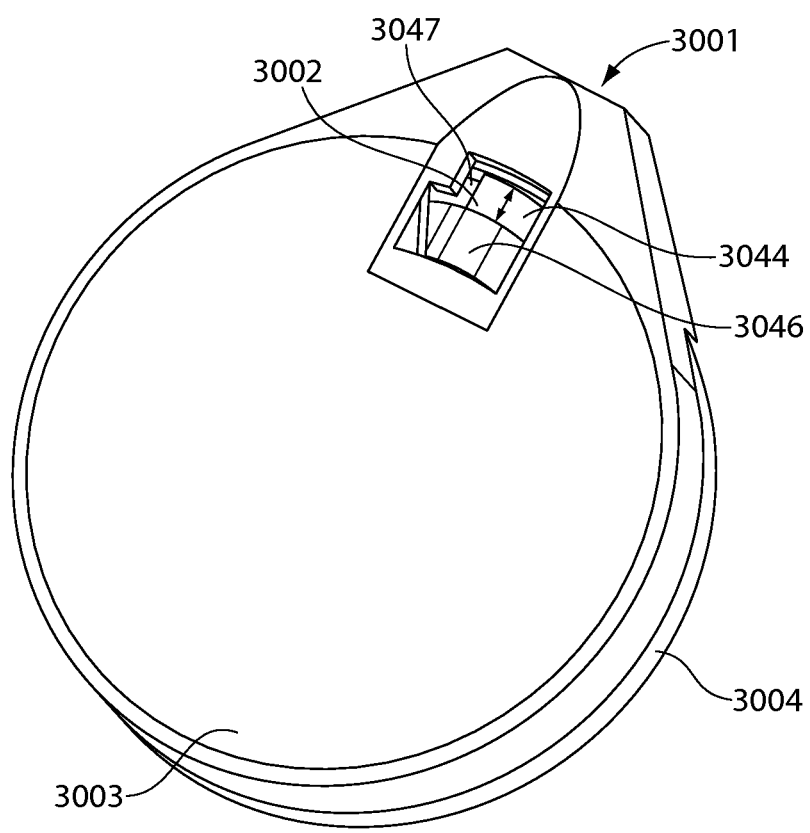
FIG. 27 shows a perspective view of another embodiment of a multi-dose device that includes a mouthpiece positioned on the periphery of the device.

As shown in FIG. 24B, which is an exploded assembly view of the embodiment of FIG. 24A, the plurality of dispersion engines 3002 may be configured in a circular pattern with the dose chamber housings positioned radially outward of the passageway housings. Each of the passageways 3008, in this embodiment, are oriented parallel to a central axis of the device. It is to be appreciated, however, that dispersion chambers may be incorporated into multi-dose devices in different configurations. By way of example, the plurality of dispersion engines may be arranged with the dose chambers positioned radially inward of the circular pattern and the passageways positioned outwardly, as in the embodiment of FIG. 26A, discussed in greater detail herein. Alternately, the dispersion engines may be configured in a circular pattern with the passageways extending along radial lines of the device, as shown in the embodiment of FIG. 27, also discussed in greater detail herein. Other configurations are also possible, including the embodiment of FIGS. 28A-28B, which is an embodiment having a plurality of dispersion engines arranged in a circular pattern about a single passageway. In this embodiment, the dispersion engines include a dose chambers that may be sequentially placed into fluid communication with the passageway to deliver a dose to a subject. Additionally, by way of non-limiting example, a plurality of dispersion engines may be incorporated into a multi-dose device in a U-shaped configuration, a linear array, a grid pattern, or in other types of patterns.

In use, a subject draws air from the mouthpiece of the multi-dose device. This creates a reduced pressure inside of the housing that, in turn, causes air to be drawn into the dose chamber 3007 to entrain medicament for delivery to the subject. Air may enter the multi-dose device through the housing port 3021, through the indicator window 3006, and/or through any other openings that lead into the housing. A portion of the air entering the device may flow directly to and through the mouthpiece 3001, bypassing the dispersion engine 3002 and meeting, in the mouthpiece, with air that has passed through the dispersion engine. Other portions of air entering the device flow toward and into the passageway inlet 3022 and the air entryway 3011. Air that enters the passageway inlet 3022 may flow directly through the passageway 3008, to the passageway outlet 3023 and exit the device through the mouthpiece. Air that flow to the dose chamber through the air entryway may entrain medicament, and then flows to the passageway before exiting the device through the mouthpiece 3001 to deliver the medicament to the subject.

The percentage of air that flows through various portions of the device may be controlled by the sizing and/or configuration of the various flow paths through the device. By way of example, the various air pathways between the housing port 3021 (or other air entryways to the device) and the mouthpiece 3001 may be made less restrictive to increase the percentage of air that flows through the mouthpiece 3001 without also flowing through a dispersion engine 3002. Similarly, making the flow pathway from the housing port 3021 to the passageway inlet 3022 and/or the air entryway 3011 more restrictive may increase the proportion of air that flows directly through the mouthpiece 3001 without also flowing through a dispersion engine 3022, while making such flow paths less restrictive will have the opposite effect. The proportion of air flow that enters the passageway 3008 through the passageway inlet 3022 and restriction 3019 versus the amount of air that flows through the air entryway and dose chamber may also be controlled by the sizing of the restriction 3019 in the passageway 3008 and/or the sizing of the air entryway 3011.

The embodiment shown in FIGS. 24A-24C includes a passageway cover 3024 that selectively prevents access to the passageway 3008 of a dispersion engine 3002 that is in registration with the mouthpiece 3001, prior to the mouthpiece being readied to dispense a dose of medicament 3025. In this regard, the passageway cover may prevent debris from entering the passageway. The passageway cover, as shown, is incorporated into a mechanism that pivots about the central axis of the multi-dose device. The mechanism includes the passageway cover 3024, a pivot 3026, a spring loading device 3027 and a leg 3028 that engages a portion of the dose chamber (the lever portion, in the illustrated embodiment) to hold the passageway cover 3024 in position over a passageway 3008. Prior to readying a dose for delivery, the passageway cover 3024 is positioned between the outlet 3023 of the passageway and an inlet to the mouthpiece when a dispersion engine is in registration with the mouthpiece to block access to the passageway. In this position, the leg 3028 of the mechanism is engaged with the lever portion 3005 of the registered dispersion engine, which holds the spring loading device 3027 in a compressed state against a mating feature in the upper housing 3003. As the dose chamber housing 3009 is moved downward to ready a dose for delivery, the lever portion 3005 moves out of engagement with the leg 3028. This allows the spring loading device 3027 to urge the passageway cover 3024 out from between the passageway outlet 3023 and an inlet to the mouthpiece 3001, thereby opening fluid communication therebetween. It is to be appreciated that the above described mechanism is but one type of mechanism that may be used to open fluid communication between a mouthpiece and passageway and that other embodiments may incorporate different mechanisms, or may lack such a feature altogether.

Embodiments of the multi-dose device may include mechanisms to prevent the mouthpiece 3001 from moving into registration with a dispersion engine that no longer contains a dose, at least until each dose in the device has been delivered. The embodiment shown in FIGS. 24A-24C includes a ratcheting mechanism 3029 and an abutment 3030 on the housing port 3021 to accomplish this. The ratcheting mechanism 3029 is mounted on a spindle that lies on the central axis of the multi-dose device. The spindle 3031 engages the upper housing 3003, when the multi-dose device is assembled, in a manner that may prevent rotation between the upper housing 3003 and ratcheting mechanism 3029. One or more curved, flexible fingers 3032 extend from the spindle 3031 and engage teeth in a ring like structure 3032 that supports the dispersion engines and the lower housing 3004. When the upper housing 3003 rotates in the clockwise direction (as viewed from above the upper housing), relative to the lower housing 3004, the flexible fingers 3032 may index into different sets of the plurality of teeth. Rotation in the opposite direction is prevented, however, by the engagement between the flexible fingers 3032 and the teeth. Additionally, engagement between the lever portion of a dose chamber housing and the abutment of the housing port, when the lever portion 3005 of the dose chamber housing 3009 is depressed, may prevent movement of the dose chamber in an incorrect direction. It is to be appreciated that the ratcheting mechanism and abutment described with respect to the embodiment of FIGS. 24A-24C are but two types of features that may prevent a mouthpiece from registering with dispersion chambers that no longer contain a dose, and that others are also possible.

Embodiments of the multi-dose device may also include features to alert a subject when the dispersion engine and mouthpiece are in registration with one another. In the embodiment of FIGS. 24A-24C, the port 3021 in the upper housing 3003 includes a registration stop 3035 that engages the lever portion 3005 of a dose chamber to prevent inadvertent rotation beyond a position where the dispersion engine and mouthpiece are in registration. Depressing the lever portion 3005 to ready the dose chamber 3007 for dispensing a dose also moves the lever portion 3005 to a position below the registration stop 3035 to allow further rotation, such as after the dose has been delivered. As noted above, the same motion may position the lever portion 3005 in line with an abutment of the housing port 3021 to prevent the dispersion engine 3002 from rotating in the opposite direction, relative to the mouthpiece 3001. It is to be appreciated that the registration stop shown in FIGS. 24A and 24B is but one type of feature that may be used to alert a user when a dispersion engine is registered, and that other configurations of positive stops are also possible. Additionally and/or alternately, various embodiments may include visual and/or audible indicators that are activated when a dispersion engine is in position.

Indicators may be incorporated in multi-dose devices, according to some embodiments, to display the number of doses remaining or the number of doses that have been used. In the embodiment of FIGS. 24A-24C numbers corresponding to the number of doses are positioned on an indicator band 3036, and are visible through the indicator window 3006 of the upper housing 3003. After a dose has been delivered from a dispersion engine 3002, and the mouthpiece 3001 is indexed to the next dispersion engine in the device, the indicator window 3006 moves relative to the indicator band 3036 and displays a new number. According to some embodiments, other types of indicators may be used. By way of example, in some embodiments, the indicator may include color, such as red to indicate that there are no more doses in a device, or that very few doses remain in the device, yellow to indicate caution regarding the number of doses remaining, and green to indicate that numerous doses remain. It is also to be appreciated that other embodiments may include different types of indicators or no indicators at all.

Various actions occur within the multi-dose chamber of FIGS. 24A-24C when a dispersion engine 3002 is moved into registration with the mouthpiece 3001. As the upper housing 3003 is rotated clockwise (as viewed from above the upper housing) relative to the lower housing 3004, a dispersion engine 3002 moves into the housing port 3021 and into registration with the mouthpiece 3001. The leg 3028 of the passageway cover 3024 engages the lever portion 3005 of the dose chamber housing 3009 to cause the passageway cover 3024 to move with the dispersion engine 3002 and to compress the loading device of the mechanism against a feature in the upper housing 3003. The lever portion 3005 of the dose chamber housing, in its upper position, engages a registration stop 3035 in the port 3021 of the upper housing 3003 when the dispersion engine 3002 is registered with the mouthpiece 3001. Additionally, the ratcheting mechanism 3029 indexes to prevent the mouthpiece from moving out of registration with the dispersion chamber in the opposite direction.

A dose in the registered dispersion engine of the multi-dose device shown FIGS. 24A-24C, may be readied for delivery by depressing the lever portion 3005 of the dose chamber that extends through the housing port 3021. Depressing the lever portion 3005 moves the dose chamber housing 3009 downward, relative to a passageway housing of the same dispersion engine. This motion positions the opening of the dose chamber housing 3009 in line with the opening of the passageway housing 3010, thus opening fluid communication between the passageway 3008 and the dose chamber 3007, where the dose resides. Depressing the lever portion 3005 also moves the lever below the leg 3028 of the passageway cover 3024, which allows the spring loading element 3027 to expand, moving the passageway cover 3024 from between the mouthpiece 3001 and the passageway 3008 and providing fluid communication therebetween. A subject may then inhale through the mouthpiece 3001 to draw medicament from the dispersion engine.

Depressing the lever portion 3005 also moves the lever out of engagement with the registration stop 3035, which allows the mouthpiece to be moved out of registration with the dispersion engine, after a dose has been delivered.

Dispersion engines may include features to prevent the ingress of air, moisture, and the like into the dose chamber, which may help preserve medicament in the dose chamber when the chamber is closed. By way of example, in the embodiment of FIGS. 25A-25E, engagement between the bearing track 3012 of the passageway housing 3010 and the corresponding features of the chamber housing 3009 urge mating faces 3014 of the passageway housing and dose chamber housing into a sealed connection with one another. The mating faces may comprise a relatively soft material, like plastic, that may allow the surfaces to conform to one another to provide a good seal. Additional sealing material may be incorporated into the dispersion engine to help seal the dose chamber prior to the dispersion chamber being configured to deliver a dose. By way of example, according to some embodiments, sealing material such as wax, rubber, and/or foil, may be positioned about the dose chamber housing to prevent the ingress of air to the dose chamber. Adhesives, heat seals, ultrasonic welds, and the like may also be used to provide a seal for dose chambers. Movement of the dose chamber into fluid communication with the passageway may break the seal provided by the sealing material when the dose is ready to be dispensed.

As discussed above, different configurations of dispersion engines may be incorporated into multi-dose devices. FIGS. 25A-25E, show but one embodiment of such a dispersion engine. The dispersion engine of FIGS. 25A-25E includes a substantially cylindrical dose chamber that is oriented with a longitudinal axis that lies parallel to the longitudinal axis of the passageway. The opening of the dose chamber provides both a pathway for air to enter the dose chamber and to exit the dose chamber. The chamber, as illustrated in FIG. 25E, includes an obstacle 3037 that may direct air circulating through the chamber 3007 back toward air that is entering the chamber 3007. This may promote recirculation of air flowing through the dose chamber, an even metering of medicament from the dose chamber, and/or the break up of any agglomerated particles that may be in the dose chamber.

Flow enters the opening of the dose chamber 3007 along an entryway wall 3036 of the dose chamber interior wall, as illustrated in FIG. 25E. The flow of air generally follows the interior wall 3038 about the cylindrical dose chamber 3007, and is eventually directed back toward the entryway wall 3036 of the dose chamber by an obstacle 3037, or trailing portion of the interior wall 3038. A portion of the air that is directed back toward the entryway wall of the dose chamber may be recirculated through the dose chamber and a portion may flow out of the dose chamber through the opening.

The flow of air through the dose chamber causes medicament therein to be pushed outwardly against the interior wall of the dose chamber and may spread the medicament evenly about the interior wall. Air then flows across the surface of the medicament, entraining particles of the medicament as the flow progresses about the dose chamber. Entrained particles may tumble about the chamber and be broken down in to smaller particles for improved delivery. Additionally, larger particles entrained within the flow may have too much momentum to turn back toward the opening, as the flow of air turns toward the opening to exit the chamber. These larger particles may continue on a path toward the entryway wall of the dose chamber and become entrained in the flow of air that is entering the chamber. In this respect, the larger particles may be recirculated back through the chamber to be de-agglomerated into smaller particles or may remain indefinitely within the chamber.

Air that exits the dose chamber flows out of the opening, through a tortuous pathway 3040 and toward a swirl chamber 3039. The tortuous passageway 3040 may, as shown, includes a right angle bend 3041 that directs the flow of air in a first direction and then another right angle bend 3042 that directs the flow of air in another direction, toward the swirl chamber 3039. Particles entrained in air may impact walls of the tortuous pathway 3040 as they pass therethrough, which may cause particles therein to tumble, breaking the particles apart and/or further dispersing the particles about the flow. Additionally or alternately, features in the pathway may cause turbulence in air flowing there through, further dispersing medicament about the flow. Although the pathway shown in FIG. 25E has a pair of right angle bends, it is to be appreciated that any number of bends of any degree may be positioned in tortuous pathways of other embodiments. Additionally or alternately, pathways may include baffles or other features positioned within the pathway to create turbulence and/or tumbling of particles to further disperse medicament about the flow path. Other embodiments may, however, lack a tortuous pathway altogether, with flow being directed through the chamber outlet and to the passageway without intentionally creating additional turbulence or tumbling.

The passageway may include a swirl chamber 3039 that creates further turbulence in air received from the chamber outlet 3017. As shown in FIGS. 25B and 25E, the swirl chamber 3039 may be positioned downstream of the restriction 3019 in the passageway 3008, and may have a wider cross-sectional area about the passageway axis than the restriction 3019. In this respect, the restriction 3019 may create a Venturi, such that air passing through the restriction accelerates as it enters into the swirl chamber 3039. The swirl chamber may receive air tangentially from the tortuous passageway 3040 and/or chamber outlet 3017, as shown in FIG. 25E. This may cause air entrained with medicament, as received from the dose chamber, to swirl in a vortex about air that enters the swirl chamber from the restriction. The turbulence created by such a vortex may promote further dispersion of the medicament about the passageway, and mixing between air received from the restriction and air received from the dose chamber. The walls of the swirl chamber, as shown in FIG. 25B, are tapered together at points closer to the passageway outlet, which further promotes mixing of the flows that enter the swirl chamber through the dose chamber outlet and through the restriction. Additionally, the higher velocity flow of air created by the Venturi may also help clear any residual powder from the swirl chamber.

As mentioned above, the embodiment shown in FIGS. 24A-24C represents but one way in which a multi-dose device may be configured. One alternate arrangement is shown in FIG. 26A, where the dispersion engines 3002 are arranged in a circular pattern, with the passageway housings 3010 positioned radially outward of the dose chamber housings 3009. A mouthpiece 3001 is integrated into an upper housing 3003 that is rotatable relative to the plurality of dispersion engines, as in the embodiment of FIGS. 24A-24C. The multi-dose device includes a single, central button 3043 that may be depressed to ready a dose for delivery from a dispersion engine 3002 that is in registration with the mouthpiece 3001. The embodiment of FIG. 26 may include other features similar to those described with respect to the embodiment of FIGS. 24A-24C, such as mechanisms to help position a dispersion engine in registration 3045, mechanisms to cover a passageway of a dispersion engine prior to a dose being readied for delivery, and/or features to provide an indication of the number of doses that remain in the device.

The embodiment of FIG. 27 shows yet another way in which a multi-dose device may be configured. As shown, a mouthpiece 3001 is positioned on the perimeter of the upper housing 3003 and is oriented to deliver air and medicament radially outward 3044 of the device. A plurality of dispersion engines 3002 are arranged within the device in a circular pattern, with the passageways 3008 of each dispersion engine 3002 also oriented along radial lines of the device. Like in the embodiments of FIGS. 24A-24C, dispersion engines may be brought into registration 3045 with the mouthpiece 3001 by rotating the upper housing 3003 relative to a lower housing 3004 that is connected to the plurality of dispersion engines. Once registered, a tab 3046 of a dispersion engine is exposed in a window 3047 on the upper housing 3003, and may be moved to ready a dose to be dispensed from the registered dispersion engine 3045. In the illustrated embodiment, this is accomplished by urging the tab 3046 radially inward of the multi-dose device. Moving the tab 3046 may ready a dose for delivery in a manner similar to moving the lever portion 3005 of the embodiment shown in FIGS. 24A-24C. By way of example, moving the tab 3046 may place the dose chamber in fluid communication with the passageway of the registered dispersion engine 3045 and may allow a passageway cover 3024 to move, thereby opening fluid communication between the mouthpiece and passageway. Moving the tab 3046 inwardly may also allow the registered dispersion chamber 3045 to be moved out of registration with the mouthpiece, such as after a dose has been dispensed.

It is to be appreciated that the embodiments shown in FIGS. 24A-24C, FIGS. 26A-26C, and FIG. 27 illustrate but a few of the features, and variations thereof that may be incorporated into a multi-dose device. For example, in other embodiments configured generally like those of FIGS. 24A-24B and FIG. 26A-26C, the mouthpiece may include a right angle bend such the mouthpiece outlet is directed in a radial direction of the device. In other embodiments, the mouthpiece may be configured to fold into the envelope of the device when not in use. Including foldable mouthpiece, in this manner, may allow the overall size of the device to be reduced, which may promote portability and allow a subject to more easily place the device into a pocket. The unfolding of the mouthpiece may also be used to open fluid communication between a dose chamber and passageway, such as through a linkage or camming action, according to some embodiments.

Figure 28A:
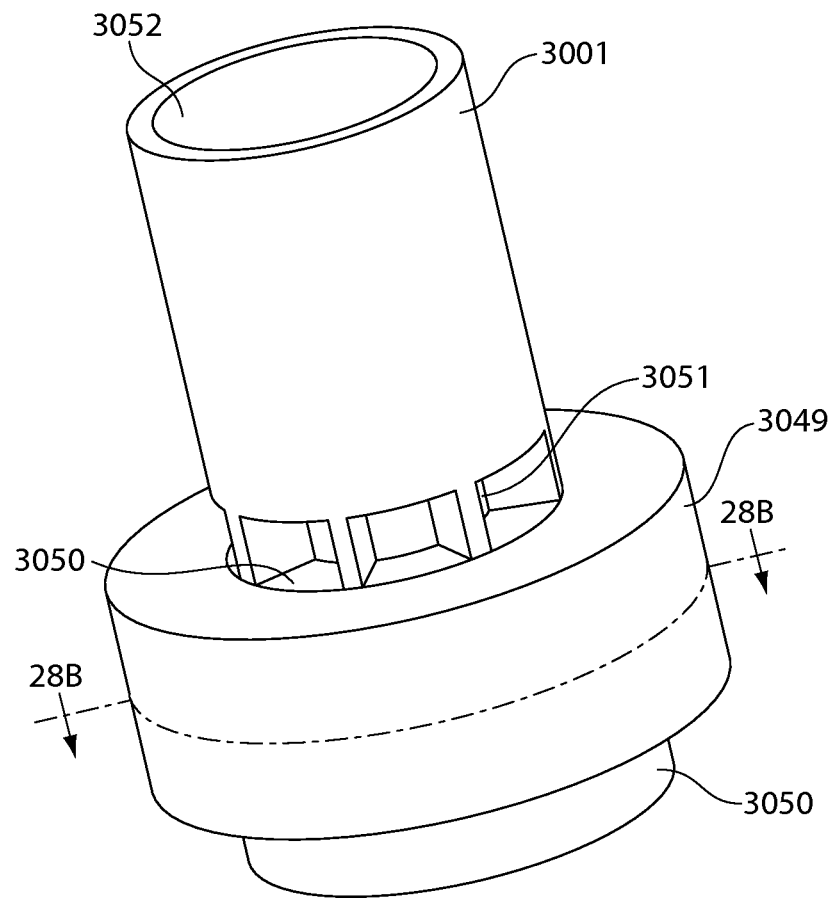
FIG. 28A shows a perspective view of another embodiment of a multi-dose device that includes a common passageway that may be placed in fluid communication with each of a plurality of dose chamber housings.
Figure 28B:
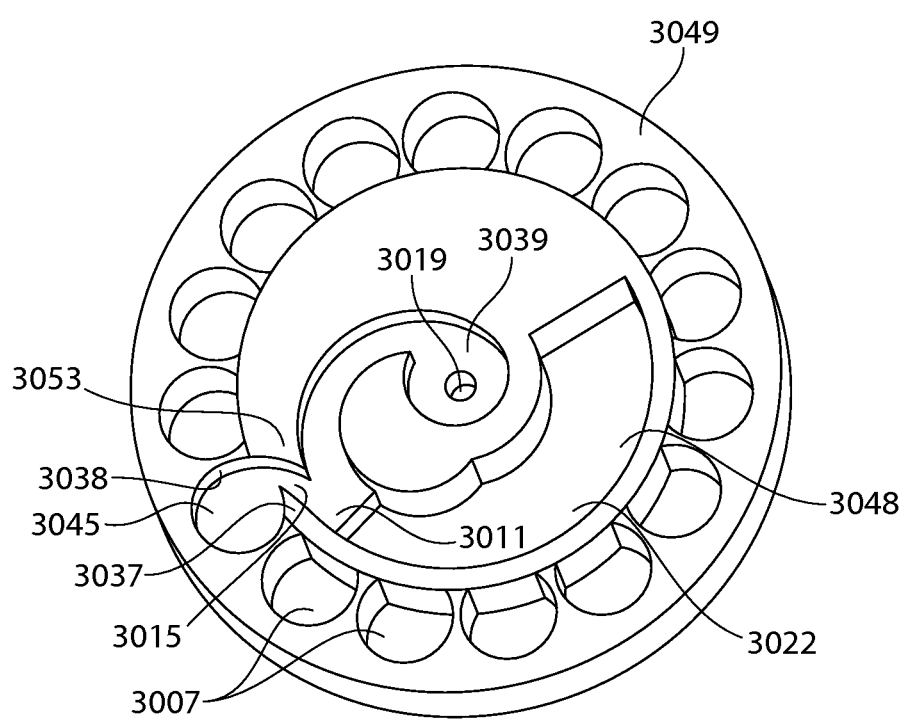
FIG. 28B shows a perspective, cross-sectional view of the embodiment of FIG. 28A, taken along lines 28B-28B.

FIGS. 28A and 28B illustrate another embodiment of a multi-dose device with a plurality of dispersion engines that share a common passageway 3048. As illustrated, a plurality of dose chambers 3007 is arranged in a circular pattern of an outer housing 3049. The outer housing is rotatably mounted on an inner housing 3050 that includes a common passageway 3048 and mouthpiece 3001. In use, a subject draws air from the mouthpiece 3001, which causes air to enter the registered dose chamber 3045, where medicament may be entrained for delivery to the subject. The outer housing 3049 may then be rotated relative to the inner housing 3050 to bring another dose chamber into registration to ready a dose for delivery.

When a subject draws air from the mouthpiece 3001, air enters through the passageway inlet 3022 and bypasses 3051 of the device shown in FIGS. 28A-28B. Air entering through the bypass 3051 travels directly to the mouthpiece outlet 3052 without also moving through a dose chamber 3007. A first portion of air that enters through the passageway inlet 3022 travels through the restriction/Venturi 3019, where the air accelerates and enters a swirl chamber 3039 before moving down stream to the mouthpiece outlet 3052. A second portion of air that enters through the passageway moves into an air entryway 3011. Air that enters the air entryway 3011 either moves directly toward the swirl chamber 3039 or is diverted to a registered dose chamber 3045 by a scoop-like structure 3053 that extends into the air entryway 3011. Air that enters the dose chamber travels about an interior wall 3038 of the chamber, entraining medicament, before returning to the air entryway and moving downstream to the swirl chamber.

Restrictions may be incorporated into a device in different ways than those depicted in the above described embodiments. Restriction may also be positioned to direct air flow at the chamber outlet air flow, such as by being positioned at the junction of the chamber outlet and the swirl chamber. Additionally, restrictions may be integrated into the swirl chamber wall instead of the floor and may be configured to direct air flow along the wall of the swirl chamber to promote swirling, according to some embodiments.

Figure 26B:
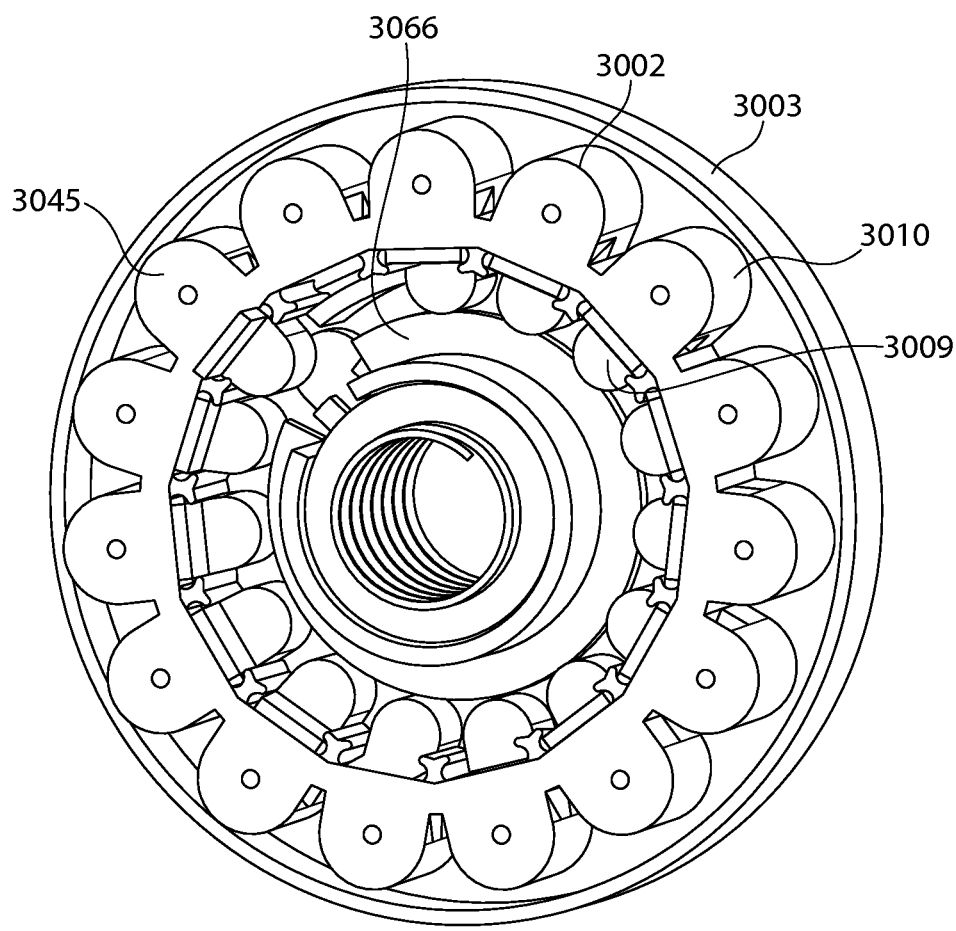
FIG. 26B shows a perspective bottom view of the embodiment of FIG. 26A, with the lower housing removed to provide a view of internal features.
Figure 26C:
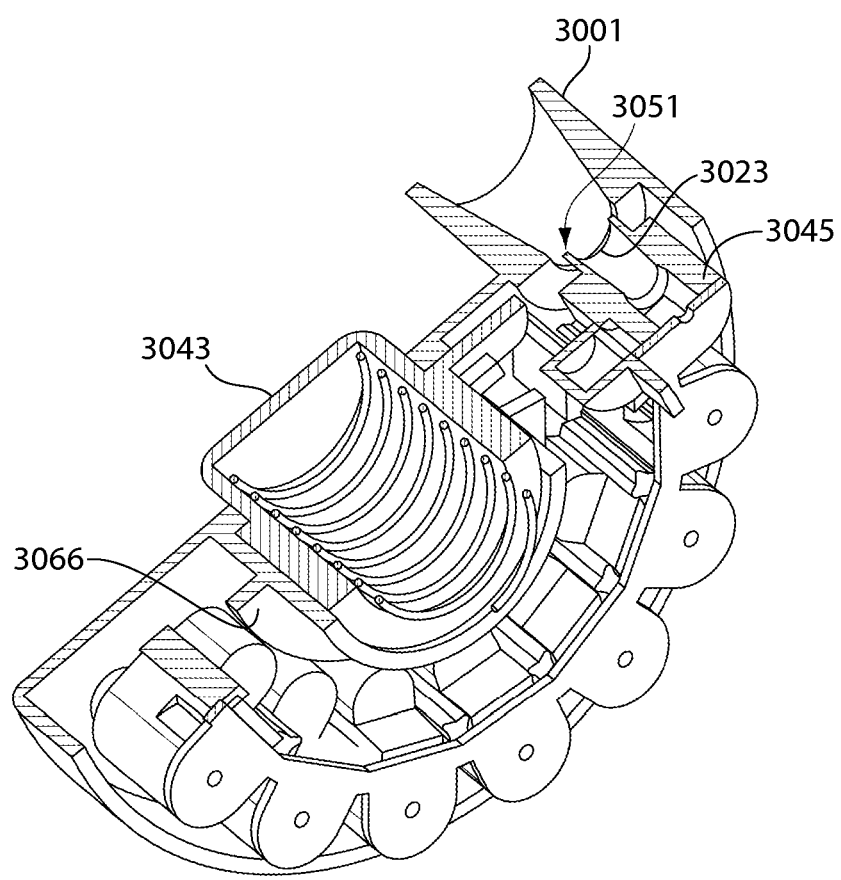
FIG. 26C shows a cross-section view of the embodiment of FIG. 26A, taken along lines 26C-26C.

Bypasses, according to some embodiments, may be configured to provide flow to the mouthpiece 3001 in a direction parallel to air entering the mouthpiece from the passageway 3008 of a device, such as is shown in FIG. 26C. According to some embodiments, a camming mechanism may be used to cause the mouth piece to move up and then seat on top of a passageway outlet, when indexed to help accomplish this.

As described with the embodiments of FIGS. 25A-25E, some air may re-circulate in the dose chamber 3007 to break up larger and/or agglomerated particles. As discussed above, one or more obstacles 3037 may be arranged in or proximate the dose chamber 3007 to facilitate this recirculation of the larger and/or agglomerated particles to break the particles down before being administered to the recipient. However, in some embodiments, the dose chamber 3007 may not include an obstacle in the air flow path. In particular, Applicant has appreciated that the geometry of the chamber itself may be sufficient to satisfactorily deliver the medicament without using an obstacle to assist in recirculation.

Figure 29:
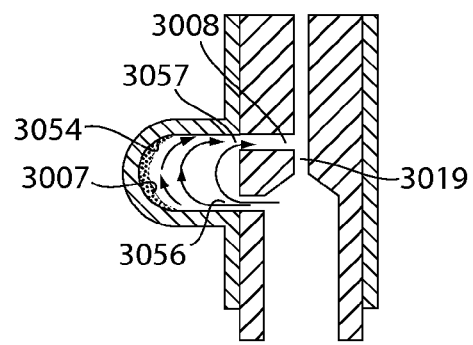
FIG. 29 shows a cross-section view of an embodiment that includes a chamber without an obstacle.

For example, FIG. 29 illustrates a portion of an inhaler device having a dose chamber 3007 adapted to deliver medicament without the provision of an obstacle in the dose chamber. The generally curved construction of dose chamber 3007 provides a natural shape for air to flow throughout the dose chamber to reduce pockets or dead spots where medicament might otherwise tend to collect in dose chambers having cornered, angular or other non-curved geometry. As air flows through the dose chamber 3007, medicament (e.g., medicament in powdered form) will spread across the internal surface 3054 of the chamber. As the air circulates, the medicament is entrained from the surface and delivered to the air passageway 3008 with minimal residual medicament left behind in the dose chamber 3007 after actuation of the inhaler. The centrifugal forces and peeling effect of the circular geometry of the dose chamber may be sufficient to satisfactorily administer medicament without the need for an obstacle. FIGS. 6A, 6D and 6E illustrates further embodiments of suitable dose chamber geometries that may be employed without requiring an obstacle.

As further shown in the embodiment of FIG. 29, the inlet 3056 and outlet 3057 may be aligned with the dose chamber 3007 to create a natural air flow path around the dose chamber, providing additional force to entrain the medicament that has been spread across the internal surface 3054 of the dose chamber. That is, the arrangement of the inlet/outlet with respect to the dose chamber forces the medicament against the curved surface where it may be optimally entrained as the air circulates around the chamber. While the inlet 3056 and outlet 3057 in FIG. 29 are arranged such they provide openings and exits, respectively, that are generally perpendicular to the passageway and which lie substantially parallel to the flow of air entering/exiting the dose chamber, the inlets and outlets may also be angled and/or configured in other ways. Other inlet/outlet arrangements that facilitate air flow throughout the dose chamber may be used, as the aspects of the invention are not limited in this respect.

As discussed above, some embodiments of an inhaler device are actuated passively, i.e., by the patient's respiration alone. However, some embodiments include one or more active air sources to facilitate the administration of a medicament. Inhaler devices having active air sources may be particularly suitable for pediatric or geriatric use or in other situations in which the individual receiving the medicament may have limited capability to administer the medicament themselves and/or have poor or undeveloped lung function. Active air sources allow a parent or other assistant to correctly administer the medicament. Active air sources may also facilitate the administration of relatively small quantities of medicament as active air sources may be configured to provide relatively high volume jets that may prove useful for entraining medicament in low flow applications, such as pediatric and geriatric applications.

Figure 30:
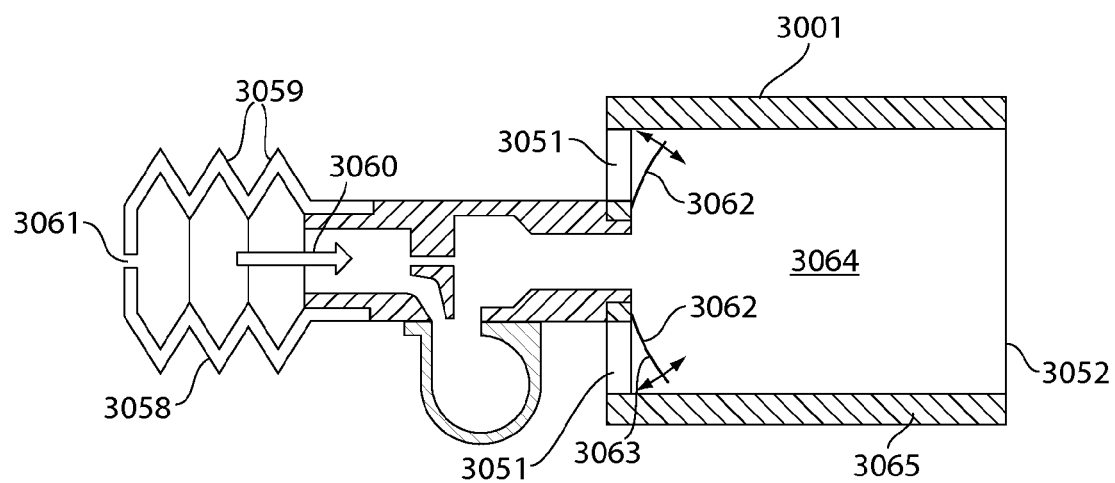
FIG. 30 shows a cross-section view of an embodiment that includes a bellows as an active air source and a mouthpiece that includes air flow indicators.

FIG. 30 illustrates an inhaler device having an active air source 3058 formed by bellows 3059. When compressed, bellows 3059 forces air through the passageway 3008 in the direction of arrow 3060. The bellows 3059 also includes a hole 3061 to prevent a back flow of air when the bellows 3059 is released. To operate the bellows, the bellows 3059 is compressed while simultaneously placing a thumb or other obstruction over the hole 3061 to force air through the passageway 3008 to the recipient of the medicament. Upon release of the bellows, the obstruction is removed from the hole, or pressure over the hole is lessened to allow leakage so that air returns to the inhaler device (e.g., the bellows is expanded) through the hole. Allowing air to enter through the hole 3061 may prevent the creation of a back flow that could prevent some of the medicament from being administered and/or that may generate suction causing the expansion air to flow from the direction of the recipient.

The hole 3061 in the bellows 3059 may eliminate the need for a check valve which may complicate the construction and adds cost to the manufacturing of an inhaler device. However, check valves may also be used in combination with the release hole in the bellows, as the aspects of the invention are not limited in this respect. In some embodiments, the bellows may be constructed from relatively inexpensive blow molded plastic to further reduce the cost and complexity of the inhaler device. However, other materials may be used to construct the bellows, as the aspects of the invention are not limited in this respect. The active air source may include other mechanisms, either alone or in combination with the bellows, such as high velocity jets, low volumetric flow sources, existing ventilator devices, etc.

As discussed above, a generally desirable inhaler may provide accurate, efficient, reliable and/or relatively simple administration of a medicament. As the final portion of the inhaler prior to administration of the medicament, the mouthpiece 3001 may be an important component in realizing one or more of the above desirable aspects of an inhaler. Accordingly, Applicant has identified a number of mouthpiece features that facilitate relatively simple and reliable administration of a medicament. Many of the features may particularly assist in the proper administration of medicament in the pediatric or geriatric context or other circumstances wherein simplicity and foolproof measures may be particularly attractive. However, the various mouthpiece features described herein may be included in any type of inhaler for administration of medicament to any type of individual, as the aspects of the invention are not limited in this respect.

Inhaler devices with active air sources are often administered by someone other than the recipient of a medicament. The familiar example is a parent administering a medicament to a child or an assistant to the elderly. Accordingly, to more effectively administer the medicament it may be beneficial for the administrator to be able to perceive the inhalation/exhalation patterns of the recipient. Applicant has appreciated that an air flow indicator 3062 disposed in or proximate to the mouthpiece 3001 may assist the administrator in properly timing the actuation of the inhaler with the inhalation of the recipient.

According to some embodiments, an indicator 3062 formed from a relatively thin film 3063 is positioned within the flow path of the mouthpiece 3001, such as is shown in the embodiment of FIG. 30. As air flow results from the breathing of the recipient, the thin film 3063 will perceptibly bend in the direction of the air flow to indicate when the recipient is inhaling and when the recipient is exhaling. The thin film 3063 may also include a relatively large surface area to ensure that movement is perceptible even in circumstances where the flow rates are relatively slow (e.g., in context wherein a recipient may have shallow or relatively weak breathing and/or lung capacity may be otherwise compromised). The indicator 3062 may be formed from any material, or may include any mechanism that provides a perceptible indication of air flow direction (e.g., so that breathing patterns may be perceived), as the aspects of the invention are not limited in this respect.

Applicant has further appreciated that the geometry of the mouthpiece may be constructed so as to facilitate optimal delivery of a medicament. As discussed above (and particularly in the context of pediatrics or geriatrics), it may be advantageous to provide an inhaler that is very simple to use and includes some level of fool-proofing so that a medicament may be reliably administered by and to unsophisticated users.

In some embodiments, the mouthpiece is shaped to bypass the teeth and tongue so that the medicament is delivered to the recipient's air passage rather than being blocked partially or completely by structures in the mouth. For example, the mouthpiece may include an elongated portion that extends out so that, when inserted in the mouth, the elongated portion bypasses the teeth and/or is naturally positioned over the tongue so that administered medicament has relatively unobstructed access to the air passages of the recipient.

Mouthpieces on many conventional inhalers are usually constructed to fit into the oral cavity in a generally perpendicular orientation with respect to the airway and/or the plane of the opening of the oral cavity. This geometry tends to administer a portion of the medicament to the back of the throat instead of down the airway. Applicant has appreciated that by shaping the mouthpiece appropriately, the air flow from the opening in the mouthpiece may be more effectively directed down the airway instead of towards the back of the throat. For example, the mouthpiece may be shaped to have a gentle downward curve to facilitate more efficient administration of the medicament into the airway of recipient.

Applicant has further appreciated that the geometry of the mouthpiece may be shaped to ensure correct and/or consistent orientation of the inhaler device during use. In some embodiments, the mouthpiece includes obstructions that interfere with the recipient's facial structures when inserted at the wrong orientation to indicate to the recipient that the inhaler device is being inserted incorrectly. For example, protrusions and or concavities may be included on the mouthpiece so that correct orientation of the inhaler device results in relatively comfortable and intuitive insertion and the incorrect orientation results in awkward or unintuitive insertion of the mouthpiece. Also, the shape of the mouthpiece may provide an intuitive indication of the correct orientation of the mouthpiece, either with or without actual physical impediments to incorrect orientation, as the aspects of the invention are not limited in this respect.

The mouthpiece geometry may also be constructed to include a dispersion cavity to accept and further disperse medicament prior to inhalation. For example, a spacer chamber 3064 may be arranged between the end of the passageway 3008 of the inhaler and the exit end 3065 of the mouthpiece 3001, or the chamber may be constructed as part of or integral to the mouthpiece. The dispersion chamber receives the medicament in the air flow from the inhaler and contains it momentarily before inhalation to improve dispersion and increase the amount of the medicament that is delivered to the recipient's lungs upon inhalation, thus improving the efficiency of the administration.

Applicant has appreciated that medicament deposition within the mouthpiece and/or within the recipient's mouth may be reduced by providing an air flow bypass 3051 on the mouthpiece 3001. The air flow bypass provides a flow path for air independent of the passageway of the inhaler up until the flow paths meet or merge in the mouthpiece. FIG. 28A illustrates one embodiment of a mouth piece having an air flow bypass. The passage way of the inhaler includes a flow path essentially along the axis of the substantially cylindrical outer housing and mouthpiece. At the base of the cylindrical mouth piece a plurality of air flow bypasses are provided to provide a flow path into the mouthpiece independent of the passageway through the inhaler (i.e., from the dose chamber).

The configuration of bypass 3051 around the circumference of the mouthpiece 3001 may be particularly advantageous as this configuration provides a cushion of medicament free air surrounding the medicament to reduce the amount of drug deposition in the periphery of the mouthpiece and the patient's mouth. That is, the general circular barrier of non-medicated air may prevent the medicament from adhering to portions of the mouthpiece and the internal structures of the recipient's mouth, thus delivering more medicament to the recipient. However, other configurations and placements of air flow bypasses may be used, as the aspects of the invention are not limited in this respect.

The addition of the bypass may also slow the flow or air to the recipient's throat, thereby preventing air laden with medicament from impinging the back of a recipient's throat, which otherwise might prevent delivery of medicament to the recipient's lungs.

In some embodiments, the air flow indicators 3062 described above may be advantageously integrated with the air flow bypass 3051 to indicate the inhale/exhale patterns of the recipient as air moves in both directions through the bypass in rhythm with the recipient's breathing. Additionally, it is to be appreciated that exhalation could go through the bypass and/or back down the passageway, and/or through a subject's nose.

In some embodiments, the mouthpiece may include one or more check valves to prevent air (e.g., exhalation air flow) from flowing through the mouthpiece 3001 and/or passageway 3008 of the inhaler in the wrong direction. The check valves may be implemented as any type of check valve including, but not limited to, flapper valves, umbrella valves, duckbill valves, ball in cavity, etc.

In some embodiments, one or more check valves may be integrated in a mouthpiece air flow bypass 3051 (e.g., the air flow bypass described in connection with FIG. 28A). That is, one or more check valves could be positioned such that air is allowed to enter the mouthpiece 3001 through the air flow bypass 3051 but is prevented from exiting the air flow bypass 3051 in the opposite direction. Check valves integrated in the air flow bypass may prevent medicament delivered from the passageway of the inhaler from incorrectly being forced out the bypass instead of out the exit of the mouthpiece positioned in the oral cavity of the recipient. Check valves integrated within air flow bypass may also be employed as an air flow indicator. For example, if the valve check is visible to an administrator of the medicament, the opening and closing of the valve check provides indication of the recipients breathing patterns to facilitate correct timing of the actuation of the inhaler.

As discussed above, a substantially airtight seal on the dose chamber may facilitate a longer shelf life for the enclosed medicament, and may assist in preserving the integrity of the medicament by preventing contaminants from entering the dose chambers. This may be particularly important in the context of multi-dose inhalers wherein all doses are not used immediately and maintaining the integrity of the medicament over time intervals, sometimes substantial time intervals, may be important. Applicant has appreciated that plastic on plastic seals may be vulnerable to creep and relaxation that may overtime admit contaminants into the dose chambers. As a result, Applicant has developed a number of measures to ensure the integrity of the dose chamber seals.

In some embodiments, to improve sealing, a removable circular band may be positioned to urge mating faces of the plurality of dose chamber housings against the corresponding mating faces passageway housings. In one embodiment, the circular band may include a 'C' shaped metal clip, although other configurations are also possible. This band may be adjustable in tightness so that it provides substantial pressure to provide a tight seal at the mating faces of the dose chamber housings and passageway housings. This band may be applied during long term storage to provide additional sealing force and later removed when the inhaler is to be used.

In an alternative embodiment, a non-moving, non-flexible geometry may be incorporated into a device to create additional sealing force. For instance, as shown in FIGS. 26B and 26C, a band 3066 is incorporated into upper housing 3003 to urge dose chamber housings 3009 radially outward, toward corresponding passageway housings 3010. Here, the band 3066 provides an outward pressure on the dose chambers, increasing the sealing force between the dose chambers and the corresponding mating faces of the circular housing.

Embodiments of the band may include a gap that rotates with an upper housing such that pressure will not be applied to a dispersion engine that is in registration with a mouthpiece. Therefore, when a particular dispersion engine is rotated into registration with the housing port 3021, the dose chamber 3007 will be relieved of the pressure of the geometry due to the gap. As a result, the dose chamber may be transitioned to an open position more easily to ready a dose to be administered. The reduced sealing force resulting when a dose chamber is rotated into alignment with the housing port should not be problematic as the administration of the medicament in the open dose chamber is likely imminent and the integrity of the medicament will not likely be compromised in this relatively short time frame.

Embodiments of inhalation devices may be manufactured as disposable and/or reusable devices. According to some embodiments, some components may be disposable while others are reusable. By way of example, in some multi-dose embodiments, like that of FIGS. 26A-26C, the dispersion engines 3002 may comprise a sub-assembly that may be replaced by a user when medicament has been dispensed from each chamber, while the upper housing 3003 and mouthpiece 3001 of this embodiment may be reusable. For such a configuration, the sealing band 3066 may be moved to the lower housing to provide improved sealing prior to the dispersion engines being engaged with the upper housing.

Embodiments may also be manufactured with or without secondary packaging. Lacking secondary packaging may additionally or alternatively reduce the overall bulk of the devices and systems and reduce the complexity of manufacturing. The devices and systems may be manufactured from stable materials with long shelf lives. For example, the devices and systems may be manufactured from materials that do not become brittle over time, or materials having biological origin that may contain microbiological organisms, which may contaminate the drug.

In further embodiments, additional material may be positioned between the dose chambers and the mating faces to provide a seal when the chamber is in the closed position, for example, an elastomer or a deformable plastic to produce an improved seal. In addition, labyrinth seals may be used between the dose chambers and the mating faces of the circular housing to prevent moisture from entering the dose chambers and compromising the integrity of the medicament.

Dose chambers in the context of multi-dose devices may also be sealed by providing a foil layer (e.g., a blister seal) over the opening of each dose chamber. When each dose chamber is rotated into position, one of numerous mechanisms may be employed to puncture the blister seal to provide access to the medicament. In particular, Applicant has developed numerous methods in the context of single dose inhalers for the external and internal puncture of blister seals. For example, various methods of puncturing blister seals are described in U.S. Patent Publication No. 2007/0151562, filed Jul. 20, 2006, which is herein incorporated by reference in its entirety. In addition, additional internal and external puncture methods are illustrated in FIGS. 11, 12 and 13, and described in the associated text herein.

These methods may be extended to multi-dose inhalers. For example, the single dose devices described with respect to FIGS. 11A-11F, 12A-12F, 13A-13C, and others, may be configured for use as multi-dose devices. By way of example, the mouthpiece 1140 and plunger 1175, as described with respect to the embodiment of FIGS. 11A-11F, may be configured to be used with a plurality of dispersion engines enclosed within a blister package (i.e., the second housing 1150 shown in FIG. 11A). Sheets forming the blister package may separately enclose a plurality of dispersion engines that may be accessed individually with the plunger and mouthpiece to ready a dose to be dispensed. According to some embodiments, the plurality of dispersion engines/blisters are arranged in a grid-like manner, while other embodiments may comprise a linear or circular array of dispersion engines disposed in individual blisters.

Having thus described several aspects of at least one embodiment of this invention, it is to be appreciated various alterations, modifications, and improvements will readily occur to those skilled in the art. By way of non-limiting example, each of the embodiments described for use with dispensing powdered medicament may also be used to dispense other materials, such as powdered foods or even liquids. Such alterations, modifications, and improvements are intended to be part of this disclosure, and are intended to be within the spirit and scope of the invention. Accordingly, the foregoing description and drawings are by way of example only.

The invention claimed is:

1. A device, comprising:
a first chamber having a toroidal shape, an inlet, and an outlet and being arranged to disperse dose in a fluid delivered to the first chamber via the inlet, the inlet being arranged at a radially inner side of the toroidally-shaped first chamber, the outlet being arranged for fluid coupling to an air flow path of a housing to provide dose entrained air to the air flow path, fluid entering the first chamber via the first chamber inlet being arranged in an inlet direction that is radially outward relative to the toroidally-shaped first chamber, and wherein the first chamber, the first chamber inlet and the first chamber outlet are arranged such that fluid flowing in an outlet direction out of the first chamber to the first chamber outlet is transverse to, and crosses, fluid flowing in the inlet direction.

2. A dose delivery device according to claim 1, comprising:

a housing defining the first chamber and having an inlet, an outlet, and an air flow path extending between the inlet and the outlet, the air flow path including a venturi feature between the inlet and the outlet; and the first chamber defines a dose chamber that holds a dose in a closed space that is selectively openable and is fluidly couplable to the air path to deliver dose to the air flow path near the venturi feature, the first chamber being arranged to disperse the dose into an air flow in the dose chamber prior to delivering the dose to the air flow path.

3. The device of claim 1, wherein the air flow path extends along an axis between the inlet and the outlet, and the fluid coupling between the first chamber and the air flow path is arranged to deliver dose to the air flow path in a direction transverse to the axis.

4. The device of claim 2, wherein the venturi feature is formed by a restriction in the air flow path.

5. The device of claim 1, wherein the first chamber inlet includes a plurality of channels that direct air to move into the first chamber.

6. The device of claim 5, wherein the plurality of channels are curved to direct fluid into the first chamber radially outward along a curved path into the first chamber.

7. The device of claim 1, wherein the first chamber outlet is arranged at the radially inner side of the toroidally shaped first chamber such that fluid flowing in an outlet direction to the first chamber outlet is transverse to, and crosses, fluid flowing in the inlet direction.

8. The device of claim 1, further comprising a second chamber having an inlet to receive dose entrained air from the first chamber, the second chamber being arranged to disperse the dose and fluidly coupled to provide dose entrained air to the housing air flow path.

9. The device of claim 8, wherein the second chamber is toroidal and defines a space arranged around, but not including, an axis.

10. The device of claim 8, wherein the second chamber is fluidly coupled to the housing air flow path by a plurality of outlet channels.

11. A dose delivery device comprising:

a housing having an air flow path;

a dose chamber arranged to hold a dose and to provide dose entrained air from the dose chamber;

a second chamber having an inlet to receive dose entrained air from the dose chamber, and being fluidly coupled to provide dose entrained air to the housing air flow path, the second chamber defining a space arranged around, but not including, an axis, the space having an inner side nearer the axis than an outer side of the space; and an inlet opening at the inner side of the second chamber space, the inlet opening being arranged to direct dose-free air into the second chamber, wherein the second chamber and the inlet opening are arranged so that air flow entering the second chamber via the inlet opening causes swirling flow in the second chamber about the axis to disperse dose in the second chamber, and wherein the dose chamber defines a space to hold the dose that is positioned radially away from the axis such that the axis does not pass through the dose chamber.

12. The device of claim 11, wherein the dose chamber has a toroidal shape and is arranged to receive air into the dose chamber in a radially outward direction into the dose chamber.

13. The device of claim 12, wherein the dose chamber is arranged to receive air from the inlet opening.

14. The device of claim 11, wherein the inlet opening includes a plurality of channels arranged to carry air flow in a direction away from the axis.

15. The device of claim 11, wherein the second chamber inlet is fluidly coupled to the air flow path via the inlet opening.

16. The device of claim 11, wherein the second chamber has a toroidal shape.

17. The device of claim 16, wherein an outlet of the dose chamber and the inlet opening are fluidly coupled to the second chamber inlet.

18. The device of claim 11, wherein the air flow path of the housing is arranged in a direction along the axis.

19. The device of claim 11, wherein the dose chamber is selectively openable to admit air into the dose chamber.

20. A dose delivery device, comprising:
a housing that defines a fluid flow path from an inlet to an outlet;
a first chamber having a toroidal shape arranged to disperse dose within the first chamber and to deliver dose entrained air to an outlet from the first chamber, the first chamber having an inlet at a radially inner side of the first chamber; and
a second chamber having a toroidal shape and arranged to receive dose entrained air from the first chamber and to further disperse the dose and deliver dose entrained air to the fluid flow path of the housing;
wherein the first chamber is larger than the second chamber.

21. The device of claim 20, further comprising a dose contained in the first chamber.

22. The device of claim 20, wherein the first chamber is sealed from fluid communication with an environment external to the first chamber, and the first chamber is selectively openable for fluid communication with the fluid flow path.

23. The device of claim 20, further comprising a mouthpiece in fluid communication with the fluid flow path to deliver dose entrained air to a user.

24. The device of claim 20, wherein the first chamber has a larger volume than the second chamber.

25. The device of claim 20, wherein the inlet of the first chamber includes a plurality of outlet channels.

26. The device of claim 25, wherein the plurality of channels are curved to direct fluid into the first chamber radially outward along a curved path into the first chamber.

27. The device of claim 20, wherein the second chamber is fluidly coupled to the fluid flow path by a plurality of outlet channels.

28. The device of claim 27, wherein the plurality of outlet channels direct flow radially inwardly from the second chamber toward the fluid flow path.

29. The device of claim 28, wherein the plurality of outlet channels are curved.

30. A drug delivery device, comprising:
a housing that defines a fluid flow path from an inlet to an outlet;
a first chamber having a toroidal shape arranged to isolate a drug in a sealed space, the first chamber being arranged for fluid communication with the fluid flow path and to disperse the drug within the first chamber when the sealed space is in fluid communication with the fluid flow path and air moves through the first chamber; and
a drug contained in the sealed space in the first chamber,
wherein the fluid flow path includes a restriction located at a radially inner side of the toroidally-shaped first chamber that permits flow to bypass the first chamber, the restriction including a plurality of channels.

31. The device of claim 30, wherein at least some flow from the plurality of channels enters the first chamber.

32. The device of claim 31, further comprising a second chamber having an inlet to receive dose entrained air from the first chamber, the second chamber being arranged to disperse the dose and being fluidly coupled to provide dose entrained air to the fluid flow path.

33. The device of claim 32, wherein flow that bypasses the first chamber enters the second chamber.

34. The device of claim 33, wherein the second chamber has a toroidal shape.

* * * * *